United States Patent [19]

Uchida et al.

[11] Patent Number: 4,963,566
[45] Date of Patent: Oct. 16, 1990

[54] BENZIMIDAZOLYL-SULFINYL-TETRAHYDROQUINOLINES

[75] Inventors: Minoru Uchida, Komatsusima; Seiji Morita, Tokushima; Masatoshi Chihiro, Naruto, all of Japan

[73] Assignee: Otsuka Pharmaceutical Co., Ltd., Tokyo, Japan

[21] Appl. No.: 31,037

[22] Filed: Mar. 27, 1987

[30] Foreign Application Priority Data

| Mar. 28, 1986 | [JP] | Japan | 61-72322 |
| Jun. 4, 1986 | [JP] | Japan | 61-129567 |
| Aug. 1, 1986 | [JP] | Japan | 61-182377 |
| Sep. 24, 1986 | [JP] | Japan | 61-225137 |
| Dec. 24, 1986 | [JP] | Japan | 61-313662 |

[51] Int. Cl.$^5$ .................... A61K 31/47; C07D 401/12
[52] U.S. Cl. .................. 514/312; 514/313; 514/314; 544/89; 544/92; 544/128; 546/14; 546/152; 546/153; 546/156; 546/157; 546/158; 546/159; 546/165; 546/166; 546/168; 546/169; 546/172; 546/174; 546/176; 546/180; 556/488
[58] Field of Search ................ 514/312, 313, 314; 546/14, 153, 155, 156, 157, 158, 159, 165, 168, 170, 171, 172, 176, 166, 169, 174

[56] References Cited

U.S. PATENT DOCUMENTS

| 4,045,563 | 8/1977 | Berntsson et al. | 546/172 |
| 4,372,953 | 2/1983 | Uchida et al. | 546/172 |
| 4,725,691 | 2/1988 | Brändström et al. | 546/172 |
| 4,738,970 | 4/1988 | Uchida et al. | 546/153 |
| 4,873,337 | 10/1989 | Sih et al. | |

FOREIGN PATENT DOCUMENTS

| 0130729 | 1/1985 | European Pat. Off. |
| 0174717 | 3/1986 | European Pat. Off. |
| 0176308 | 4/1986 | European Pat. Off. |
| 213474 | 3/1987 | European Pat. Off. |
| 220053 | 4/1987 | European Pat. Off. |
| 2554772 | 6/1976 | Fed. Rep. of Germany |
| 240677 | 10/1987 | Japan |
| 1207771 | 10/1970 | United Kingdom |
| 1334705 | 10/1973 | United Kingdom |
| 2161160 | 1/1986 | United Kingdom |
| 2171995 | 9/1986 | United Kingdom |

OTHER PUBLICATIONS

Evans et al, Br. J. Pharmac (1987), 91, 531–537.
Perkins et al., Chemical Abstracts, vol. 99, No. 206826 (1983).
Mutschler, "Arzneimittelwirkungen" (5th Ed.), pp. 556–556 (1986).

*Primary Examiner*—Mukund J. Shah
*Assistant Examiner*—E. Bernhardt
*Attorney, Agent, or Firm*—Finnegan, Henderson, Farabow, Garrett & Dunner

[57] ABSTRACT

A hydroquinoline compound of the formula (1):

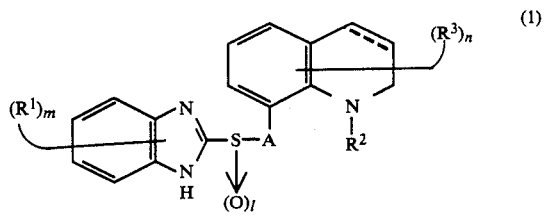

wherein $R^1$, $R^2$, $R^3$, A, l, m and n are as defined or its pharmaceutically acceptable salt, composition containing the compound and processes for preparing same are disclosed. The compound is useful as an antiulcer agent.

20 Claims, No Drawings

BENZIMIDAZOLYL-SULFINYL-TETRAHYDROQUINOLINES

FIELD OF THE INVENTION

This invention relates to new hydroquinoline compounds and pharmaceutically acceptable salts thereof which are useful as anti-ulcer agents, processes for preparing the same, and pharmaceutical compositions containing the hydroquinoline compounds or salts thereof.

BACKGROUND OF THE INVENTION

Various hydroquinoline compounds are known which have gastric acid secretion inhibitory activity as described in European Patent Publication Nos. 0,174,717 and 0,176,308.

However, the hydroquinoline compounds of this invention are structurally different from the conventional hydroquinoline compounds.

SUMMARY OF THE INVENTION

One object of this invention is to provide hydroquinoline compounds having an anti-ulcer activity.

Another object of this invention is to provide a pharmaceutical composition, containing the hydroquinoline compound in a therapeutically effective amount.

A further object of this invention is to provide a process for preparing the hydroquinoline compounds and pharmaceutically acceptable salts thereof.

As a result of extensive research this invention has been accomplished which, in one aspect, provides a hydroquinoline compound of the following formula (1) and pharmaceutically acceptable salts thereof:

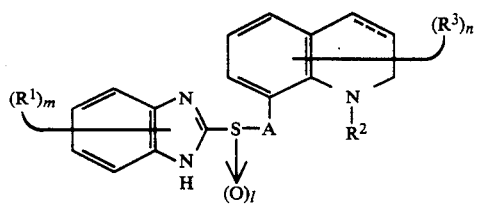

wherein A is a lower alkylene group; $R^1$ is a hydrogen atom, a lower alkyl group which may have 1 to 3 halogen atoms, a lower alkoxy group which may have 1 to 3 halogen atoms, a halogen atom, a lower alkanoyl group, a lower alkoxycarbonyl group or a cycloalkylcarbonyl group; $R^2$ is a hydrogen atom, a lower alkyl group which may have 1 to 3 halogen atoms, an amino-lower alkyl group which may have a lower alkyl group, a lower alkenyl group, a lower alkynyl group which may have a tri-lower alkylsilyl group, a phenyl-lower alkyl group which may have 1 to 3 groups selected from the group consisting of a halogen atom and an amino group which may have a lower alkyl group as a substituent on the phenyl ring thereof, a lower alkanoyl group or a cycloalkyl-lower alkyl group; $R^3$ is a hydrogen atom, a lower alkyl group which may have 1 to 3 halogen atoms, a lower alkoxy group, a halogen atom, an oxo group, a hydroxy group, a lower alkenyloxy group, a lower alkylenedioxy group, a phenyl group, a hydroxyimino group, a lower alkylimino group, a lower alkylidene group, a hydroxy-substituted lower alkyl group, a carboxy group, a lower alkoxycarbonyl group, a lower alkanoyloxy-lower alkyl group, a lower alkoxy-lower alkoxy group or a group of the formula:

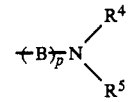

(wherein B is a lower alkylene group or a carbonyl group; p is an integer of 0 or 1; $R^4$ and $R^5$ are, the same or different, a hydrogen atom, a lower alkyl group which may have 1 to 3 groups selected from the group consisting of a halogen atom and a lower alkoxy group, a hydroxy-substituted lower alkyl group, a cycloalkyl group, a cycloalkyl-lower alkyl group, a cycloalkylcarbonyl group, a lower alkenyl group, a lower alkanoyl group which may have 1 to 3 halogen atoms or a phenyl lower alkyl group which may have a lower alkoxy group as a substituent on the phenyl ring thereof; and $R^4$ and $R^5$ together with the bonding nitrogen atom may form a saturated 5- or 6-membered heterocyclic group which may contain hetero atom(s) consisting of an oxygen atom, a sulfur atom and a nitrogen atom); m and n are integers of 1 to 3; l is an integer of 0 or 1; and the bond between the 3- and 4-positions of the quinoline skeleton is a single bond or a double bond; provided that the oxo group for $R^3$ is not substituted at the 2-position of the quinoline skeleton.

In another aspect, this invention provides an anti-ulcer composition containing the compound of the formula (1) or a pharmaceutically acceptable salt thereof in an therapeutically effective amount.

In a further aspect, this invention provides a process for preparing the compounds of the formula (1) and pharmaceutically acceptable salts thereof.

The hydroquinoline derivatives represented by the above formula (1) of this invention has an anti-ulcer action and is useful as a drug for the treatment of gastrointestinal ulcers such as gastric ulcer and duodenal ulcer.

The hydrochloric acid production at the gastric mucosa is regulated by many pharmacological factors, and the biochemical mechanism of [H+] ion production finally, is the rate-determining step. The ATPase that has a nature of being activated by H+ and K+ in gastric wall cells has been found in recent years to control the acid production. This enzyme exists specifically in gastric wall cells and plays the role of a proton pump key enzyme. An inhibitor of this enzyme can be a useful for acid secretion suppressant. The compounds of this invention particularly have both acid secretion suppressing action and cyto-protective action, suppresses ulcer factors in both respects of aggressive factors and protective factors and, moreover, is characterized by low toxicity and a long duration of acid secretion suppressing action.

DETAILED DESCRIPTION OF THE INVENTION

The groups given in terms of symbols in the above general formula (1) are respectively described in more detail in the following.

The term "lower alkylene" as used herein refers to a straight or branched chain alkylene group having 1 to 6 carbon atoms, such as methylene, ethylene, trimethylene, methylmethylene, ethylmethylene, 2-methyltrimetnylene, 2,2-dimethyltrimethylene, 1-methyltrimethylene, tetramethylene, pentamethylene, hexamethylene and the like.

The term "lower alkyl" as used herein refers to a straight or branched chain alkyl group having 1 to 6 carbon atoms, such as methyl, ethyl, propyl, isopropyl, butyl, isobutyl, pentyl, hexyl and the like.

The term "lower alkoxy" as used herein refers to a straight or branched chain alkoxy group having 1 to 6 carbon atoms, such as methoxy, ethoxy, propoxy, isopropoxy, butoxy, isobutoxy, pentyloxy, hexyloxy and the like.

The term "halogen atom" as used herein refers to fluorine, chlorine, bromine and iodine.

The term "lower alkyl group which may have 1 to 3 halogen atoms" as used herein refers to, in addition to the above-mentioned alkyl group having 1 to 6 carbon atoms, a straight or branched chain alkyl group having 1 to 6 carbon atoms which may have 1 to 3 halogen atoms, such as iodomethyl, trifluoromethyl, 2,2-difluoroethyl, 1,1-dichloroethyl, dichloromethyl, trichloromethyl, tribromomethyl, 2,2,2-trifluoroethyl, 2,2,2-trichloroethyl, 2-fluoroethyl, 2-chloroethyl, 1-fluoroethyl, 1,2-dichloroethyl, 3,3,3-trichloropropyl, 3-fluoropropyl, 4-chlorobutyl, 3-chloro-2-methylethyl and the like.

The term "lower alkoxy group which may have 1 to 3 halogen atoms" as used herein refers to, in addition to the above-mentioned alkoxy group having 1 to 6 carbon atoms, a straight or branched chain alkoxy group having 1 to 6 carbon atoms which may have 1 to 3 halogen atoms, such as iodomethoxy, trifluoromethoxy, 2,2-difluoroethoxy, 1,1-dichloroethoxy, trichloromethoxy, dichloromethoxy, tribromomethoxy, 2,2,2-trifluoroethoxy, 2,2,2-trichloroethoxy, 2-fluoroethoxy, 2-chloroethoxy, 1-fluoroethoxy, 1,2-dichloroethoxy, 3,3,3-trichloropropoxy, 3-fluoropropoxy, 4-chlorobutoxy, 3-chloro-2-methylethoxy and the like.

The term "lower alkanoyl" as used herein refers to a straight or branched chain alkanoyl group having 1 to 6 carbon atoms such as formyl, acetyl, propionyl, butyryl, isobutyryl, pentanoyl, hexanoyl and the like.

The term "lower alkoxycarbonyl" as used herein refers to a straight or branched chain alkoxycarbonyl group having 1 to 6 carbon atoms such as methoxycarbonyl, ethoxycarbonyl, propoxycarbonyl, isopropoxycarbonyl, butoxycarbonyl, isobutoxycarbonyl, pentyloxycarbonyl, hexyloxycarbonyl and the like.

The term "cycloalkyl" as used herein refers to a cycloalkyl group having 3 to 8 carbon atoms such as cyclopropyl, cyclobutyl, cyclopentyl, cyclohexyl, cycloheptyl, cyclooctyl and the like.

The term "cycloalkylcarbonyl" as used herein refers to a cycloalkylcarbonyl group having 3 to 8 carbon atoms such as cyclopropylcarbonyl, cyclobutylcarbonyl, cyclopentylcarbonyl, cyclohexylcarbonyl, cycloheptylcarbonyl, cyclooctylcarbonyl and the like.

The term "amino-lower alkyl group which may have a lower alkyl group" as used herein refers to a straight or branched chain alkyl group having 1 to 6 carbon atoms substituted with an amino group which may have 1 to 2 straight or branched chain alkyl groups having 1 to 6 carbon atoms, such as aminomethyl, 2-aminoethyl, 1-aminoethyl, 3-aminopropyl, 4-aminobutyl, 1,1-dimethyl-2-aminoethyl, 5-aminopentyl, 6-aminohexyl, 2-methyl-3-aminopropyl, methylaminomethyl, 2-ethylaminoethyl, 1-propylaminoethyl, 3-(n-butylamino)propyl, 4-pentylaminobutyl, 1,1-dimethyl-2-pentylaminoethyl, 5-hexylaminopentyl, 2-dimethylaminoethyl, 6-dimethylaminohexyl, 2-methyl-3-diethylaminopropyl, dipropylaminomethyl, 2-dipentylaminoethyl, 1-dihexylaminoethyl, 3-(N-methyl-N-propylamino)propyl, 4-(N-methyl-N-tertiary-butylamino)butyl, 2-(N-ethyl-N-pentylamino)ethyl and the like.

The term "lower alkenyl" as used herein refers to a straight or branched chain alkenyl group having 2 to 6 carbon atoms such as vinyl, allyl, 2-butenyl, 3-butenyl, 1-methylallyl, 2-pentenyl, 2-hexenyl and the like.

The term "lower alkynyl" as used herein refers to a straight or branched chain alkynyl group having 2 to 6 carbon atoms such as ethynyl, 2-propynyl, 2-butynyl, 3-butynyl, 1-methyl-2-propynyl, 2-pentynyl, 2-hexynyl and the like.

The term "lower alkynyl group which may have a trilower alkylsilyl group" as used herein refers to, in addition to the above-mentioned lower alkynyl group having 2 to 6 carbon atoms, a straight or branched chain alkynyl group having 2 to 6 carbon atoms which may have a tri(straight or branched chain alkyl)silyl group whose alkyl moieties have 1 to 6 carbon atoms, such as trimethylsilylethynyl, 3-trimethylsilyl-2-propynyl, 4-triethylsilyl-3-butynyl, 4-tripropylsilyl-3-butynyl, 3-tributylsilyl-1-methyl-2-propynyl, 5-tripentylsilyl-4-pentynyl, 6-trihexylsilyl-5-hexynyl, 3-diethylmethylsilyl-2-propynyl, 3-dimethylpropylsilyl-2-propynyl and the like.

The term "amino group which may have a lower alkyl group" as used herein refers to an amino group which may have 1 to 2 of straight or branched chain alkyl groups having 1 to 6 carbon atoms, such as amino, methylamino, ethylamino, propylamino, n-butylamino, pentylamino, hexylamino, dimethylamino, diethylamino, dipropylamino, dipentylamino, dihexylamino, N-methyl-N-propylamino, N-methyl-N-tertiary-butylamino, N-ethyl-N-pentylamino and the like.

The term "phenyl-lower alkyl" as used herein refers to a phenylalkyl group with a straight or branched chain alkyl group having 1 to 6 carbon atoms in the alkyl moiety such as benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl and the like.

Therefore, the term "phenyl-lower alkyl group which may have 1 to 3 groups selected from the group consisting of a halogen atom and an amino group which may have a lower alkyl group as a substituent on the phenyl ring thereof" as used herein refers to, in addition to the above-mentioned phenyl-lower alkyl group, a phenylalkyl group which have a straight or branched chain alkyl group having 1 to 6 carbon atoms, and which may have 1 to 3 groups selected from the groups consisting of a halogen atom and an amino group which may have 1 to 2 of a straight or branched chain alkyl group having 1 to 6 carbon atoms as substituents on the phenyl ring thereof, such as 4-chlorobenzyl, 3-fluorobenzyl, 2-bromobenzyl, 4-iodobenzyl, 2-(2-fluorophenyl)ethyl, 1-(3-bromophenyl)ethyl, 3-(4-chlorophenyl)propyl, 4-(2,3-dichlorophenyl)butyl, 5-(2,3,4-trichlorophenyl)penthyl, 6-(3,4-dibromophenyl)hexyl, 4-aminobenzyl, 3-methylaminobenzyl, 2-ethylaminobenzyl, 2-(2-propylaminophenyl)ethyl, 3-(3-butylaminophenyl)propyl, 4-(4-pentylaminophenyl)butyl, 5-(2-hexylaminophenyl)pentyl, 6-(4-dimethylaminophenyl)hexyl, 4-dimethylaminobenzyl, 3-diethylaminobenzyl, 2-dipropylaminobenzyl, 2-[4-(N-methyl-N-butylamino)phenyl]ethyl, 1-[3-(N-ethyl-N-pentylamino)phenyl]ethyl, 3-[2-(N-methyl-N-hexylamino)- phenyl]propyl, 2-fluoro-4-dimethylaminobenzyl, 2,4-diaminobenzyl, 2,4,6-triaminobenzyl and the like.

The term "cycloalkyl-lower alkyl" as used herein refers to a cycloalkylalkyl group which have 3 to 8 carbon atoms in the cycloalkyl moiety and a straight or branched chain alkyl group having 1 to 6 carbon atoms in the alkyl moiety such as cyclopropylmethyl, cyclobutylmethyl, cyclopentylmethyl, cyclohexylmethyl, cycloheptylmethyl, cyclooctylmethyl, 2-cyclopropylethyl, 1-cyclobutylethyl, 3-cyclopentylpropyl, 4-cyclohexylbutyl, 5-cycloheptylpentyl, 6-cyclooctylhexyl, 1,1-dimethyl-2-cyclohexylethyl, 1-cyclohexylethyl, 2-cyclopropylethyl, 3-cyclohexylpropyl and the like.

The term "lower alkenyloxy" as used herein refers to a straight or branched chain alkenyloxy group having 2 to 6 carbon atoms such as vinyloxy, allyloxy, 2-butenyloxy, 3-butenyloxy, trimethylallyloxy, 2-pentenyloxy, 2-hexenyloxy and the like.

The term "lower alkylenedioxy" as used herein refers to an alkylenedioxy group having 1 to 4 carbon atoms such as methylenedioxy, ethylenedioxy, trimethylenedioxy, tetramethylenedioxy and the like.

The term "lower alkylimino" as used herein refers to a straight or branched chain alkylimino group having 1 to 6 carbon atoms such as methylimino, ethylimino, propylimino, isopropylimino, butylimino, isobutylimino, pentylimino, hexylimino and the like.

The term "lower alkylidene" as used herein refers to a straight or branched chain alkylidene group having 1 to 6 carbon atoms such as methylene, ethylidene, propylidene, isopropylidene, butylidene, isobutylidene, pentylidene, hexylidene and the like.

The term "hydroxy-substituted lower alkyl" as used herein refers to a hydroxy-substituted alkyl group having a straight or branched chain alkyl group of 1 to 6 carbon atoms in the alkyl moiety such as hydroxymethyl, 2-hydroxyethyl, 1-hydroxyethyl, 3-hydroxypropyl, 4-hydroxybutyl, 1,1-dimethyl-2-hydroxyethyl, 5-hydroxypentyl, 6-hydroxyhexyl, 2-methyl-3-hydroxypropyl and the like.

The term "lower alkanoyloxy lower alkyl" as used herein refers to an alkanoyloxyalkyl group which have a straight or branched chain alkanoyloxy group having 1 to 6 carbon atoms in the alkanoyloxy moiety and a straight or branched chain alkyl group having 1 to 6 carbon atoms in the alkyl moiety, such as formyloxymethyl, acetyloxymethyl, 1-acetyloxyethyl, 2-acetyloxyethyl, 3-propionyloxypropyl, 4-butyryloxybutyl, 5-pentanoyloxypentyl, 6-hexanoyloxyhexyl, 1,1-dimethyl-2-acetyloxyethyl, 2-methyl-3-acetyloxypropyl and the like.

The term "lower alkoxy-lower alkoxy" as used herein refers to an alkoxyalkoxy group which have a straight or branched chain alkoxy group having 1 to 6 carbon atoms in the alkoxy moieties such as methoxymethoxy, 2-methoxyethoxy, 1-ethoxyethoxy, 3-propoxypropoxy, 4-butoxybutoxy, 5-pentyloxypentyloxy, 6-hexyloxyhexyloxy, 1,1-dimethyl-2-methoxyethoxy, 2-methyl-3-methoxypropoxy and the like.

The term "lower alkyl group which may have 1 to 3 groups selected from the group consisting of a halogen atom and a lower alkoxy group" as used herein refers to, in addition to the above-mentioned lower alkyl group which may have 1 to 3 halogen atoms, a straight or branched chain alkyl group having to 6 carbon atoms which may have 1 to 3 groups selected from the group consisting of a halogen atom and a straight or branched chain alkoxy group having 1 to 6 carbon atoms, such as methoxymethyl, 2-methoxyethyl, 1-ethoxyethyl, 3-propoxypropyl, 4-buthoxybuthyl, 5-pentyloxypentyl, 6-hexyloxyhexyl, 1,1-dimethyl-2-methoxyethyl, 2-methyl-3-methoxypropyl, 2,2,2-trifluoro-1-ethoxyethyl, 2,2-dichloro-1-methoxy-ethyl and the like.

The term "lower alkanoyl group which may have 1 to 3 halogen atoms" as used herein refers to, in addition to the above-mentioned lower alkanoyl group, a straight or branched chain alkanoyl group having 1 to 6 carbon atoms which may have 1 to 3 halogen atoms, such as 2-iodoacetyl, 2,2,2-trifluoroacetyl, 2,2-dichloroacetyl, 2,2,2-trichloroacetyl, 2,2,2-tribromoacetyl, 2-fluoropropionyl, 3-fluoropropionyl, 3-chloropropionyl, 2,2-dichloropropionyl, 2,3-dichloropropionyl, 3,3-difluoropropionyl, 3,3,3-trifluoropropionyl, 3,3,3-trichloropropionyl, 2,2,3-trichlorobutyryl, 2-fluorobutyryl, 5-chloropentanoyl, 6-chlorohexanoyl and the like.

The term "phenyl-lower alkyl group which may have a lower alkoxy group as a substituent on the phenyl ring thereof" as used herein refers to, in addition to the above-mentioned phenyl-lower alkyl group, a phenylalkyl group which have a straight or branched chain alkyl group having 1 to 6 carbon atoms in the alkyl moiety, and which may have 1 to 3 of a straight or branched chain alkoxy group having 1 to 6 carbon atoms as substituents on the phenyl ring thereof, such as 3-methoxybenzyl, 2-ethoxybenzyl, 2-(2-propoxyphenyl)ethyl, 3-(3-butoxyphenyl)propyl, 4-(4-pentyloxyphenyl)butyl, 5-(2-hexyloxyphenyl)pentyl, 6-(2,6-dimethoxyphenyl)hexyl, 2,3-dimethoxybenzyl, 3,4-dimethoxybenzyl, 2-(3,4-dimethoxyphenyl)ethyl, 3,4,5-trimethoxybenzyl and the like.

The term "saturated 5- or 6-membered heterocyclic group formed by $R^4$ and $R^5$ together with the binding nitrogen atom, and optionally containing hetero atom(s) consisting of an oxygen atom, a sulfur atom and a nitrogen atom" as used herein refers to pyrrolidinyl, piperazinyl, piperidino, morpholino, thiomorpholino and the like.

In the formula (1), group $R^1$ can also substitute at the 1-position of the benzimidazole ring and, when it substitutes at the 1-position thereof, the hydrogen atom is not at the 1-position.

The compounds of this invention can be produced by various procedures such as, for example, those shown in the following reaction schemes:

[Reaction Scheme-1]

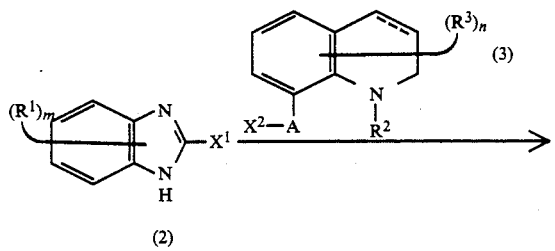

-continued
[Reaction Scheme-1]

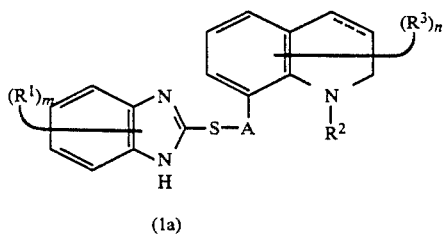

(1a)

wherein, $R^1$, $R^2, R^3$, A, m, n and the bond between the 3- and 4-positions of the quinoline skeleton have the same meanings as defined above, and $X^1$ and $X^2$ are respectively a mercapto group, a halogen atom, a lower alkanesulfonyloxy group, an arylsulfonyloxy group or an aralkylsulfonyloxy group, provided that when $X^1$ is a mercapto group, $X^2$ is a halogen atom, a lower alkanesulfonyloxy group, an arylsulfonyloxy group or an aralkylsulfonyloxy group and, when $X^2$ is a mercapto group, $X^1$ is a halogen atom, a lower alkanesulfonyloxy group, an arylsulfonyloxy group or an aralkylsulfonyloxy group.

In the formulas (2) and (3), the halogen atom represented by $X^1$ and/or $X^2$ has the same meaning as defined above; examples of the lower alkanesulfonyloxy group include methanesulfonyloxy, ethanesulfonyloxy, isopropanesulfonyloxy, propanesulfonyloxy, butanesulfonyloxy, tert-butanesulfonyloxy, pentanesulfonyloxy, hexanesulfonyloxy and the like; examples of the arylsulfonyloxy group include a substituted or unsubstituted arylsulfonyloxy group such as phenylsulfonyloxy, 4-methylphenylsulfonyloxy, 2-methylphenylsulfonyloxy, 4-nitrophenylsulfonyloxy, 4-methoxyphenylsulfonyloxy, 3-chlorophenylsulfonyloxy, α-naphthylsulfonyloxy and the like; and examples of the aralkylsulfonyloxy group include a substituted or unsubstituted aralkylsulfonyloxy group such as benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methoxybenzylsulfonyloxy, 3-chlorobenzylsulfonyloxy, α-naphthylmethylsulfonyloxy and the like.

The reaction between the compound of the formula (2) and the compound of the formula (3) can be carried out in a suitable solvent in the presence of a basic compound. Any solvent which does not adversely influence the reaction can be used. Examples of the solvent include water; alcohols such as methanol, ethanol, isopropanol, etc.; aromatic hydrocarbons such as benzene, toluene, xylene, etc.; ethers such as diethyl ether, tetrahydrofuran, dioxane, monoglyme, diglyme, etc.; ketones such as acetone, etc.; esters such as methyl acetate, ethyl acetate, etc.; aprotic polar solvents such as N,N-dimethyl formamide(DMF), dimethylsulfoxide(DMSO), hexamethyl phosphoric triamide (HMPA), etc.; or a mixed solvent thereof. Examples of the basic compound which can be used include inorganic bases such as sodium hydride, sodium hydroxide, potassium hydroxide, sodium carbonate, potassium carbonate, sodium hydrogencarbonate, potassium hydrogencarbonate, silver carbonate, etc.; alkali metals such as sodium, potassium, etc.; alcoholates such as sodium methylate, sodium ethylate, etc.; and organic bases such as triethylamine, pyridine, N,N-dimethylaminopyridine, N-methylmorpholine, 1,5-diazabicyclo[4.3.0]nonene-5(DBN), 1,8-diazabicyclo[5.4.0]undecen-7(DBU), 1,4-diazabicyclo-[2.2.2]octane(DABC), etc. The reaction proceeds advantageously with the addition of a crown ether such as 18-crown-6(i.e. 1,4,7,10,13,16-hexaoxacyclooctadecane), 15-crown-5(i.e. 1,4,7,10,13-pentaoxacyclopentadecane), 12-crown-4(i.e. 1,4,7,10-tetraoxacyclododecane) and so on.

The reaction is carried out usually at 0° C. to 150° C., preferably at about 0° C. to 100° C., and completed in about 1 to 24 hours. In the above reaction, the suitable amount of the compound of the formula (3) to be used is usually at least equimolar amount, preferably equimolar to 2 mols, of the compound of the formula (3) per mol of the compound of the formula (2).

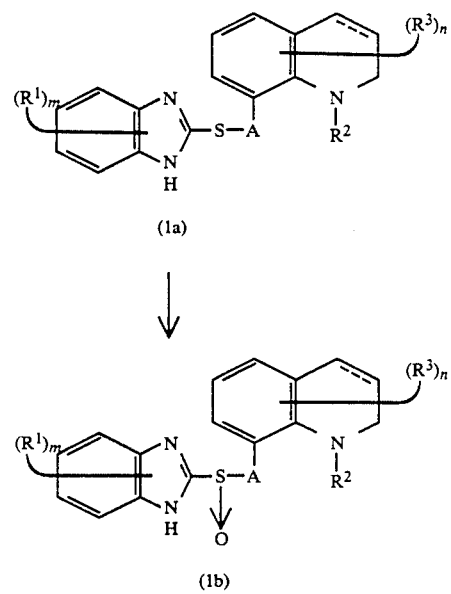

wherein $R^1$, $R^2, R^3$, A, m, n and the bond between the 3- and 4-positions of the quinoline skeleton have the same meanings as defined above.

The oxidation reaction of the compound of the formula (1a) can be carried out in a suitable solvent in the presence of an oxidizing agent. As for the solvent, any solvent which does not adversely influence the reaction can be used. Examples of the solvent include water; organic acids such as formic acid, acetic acid, trifluoroacetic acid, etc.; alcohols such as methanol, ethanol, isopropanol, etc.; and halogenated hydrocarbons such as chloroform, dichloromethane, dichloroethane and so on. Any oxidizing agent that usually oxidize a sulfide group to a sulfoxide group can be used. Examples of the oxidizing agent include peroxy acids such as performic acid, peracetic acid, trifluoroperacetic acid, perbenzoic acid, m-chloroperbenzoic acid, o-carboxyperbenzoic acid, etc.; hydrogen peroxide; chromates such as chromic acid, sodium chromate, potassium chromate, etc.; permanganates such as permanganic acid, sodium permanganate, potassium permanganate, etc.; iodates such as metasodium periodate, etc.; and selenic compounds such as selenium dioxide, etc. The suitable amount of the oxidizing agent to be used is at least equimolar amount, preferably equimolar to 1.5 mols, of the oxidizing agent per mol of the compound of the formula (1a). The reaction is carried out usually at $-70°$ C. to 40° C., preferably at about −70° C. to room temperature, and completed in about 5 minutes to 3 hours.

[Reaction Scheme-3]

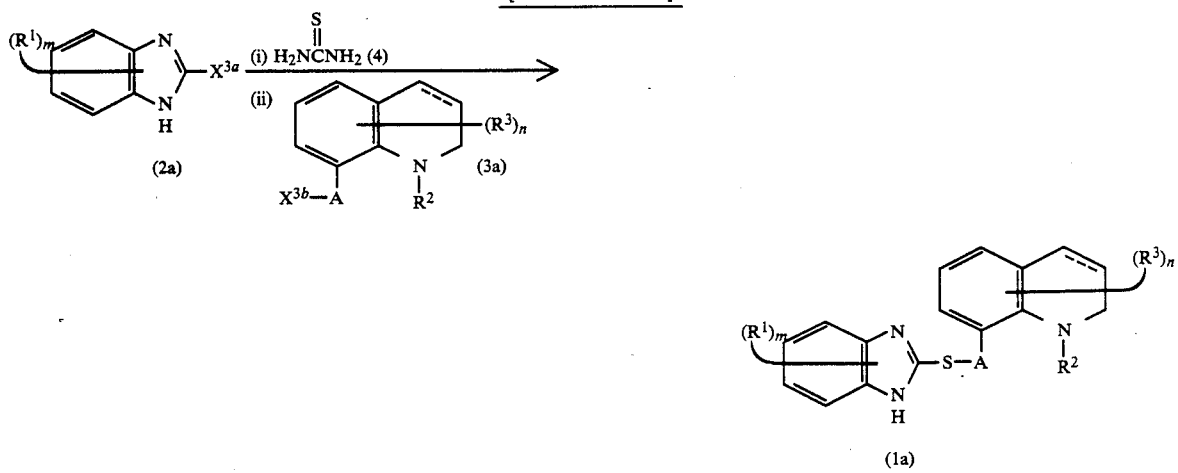

wherein $R^1$, $R^2$, $R^3$, A, m, n and the bond between the 3- and 4-positions of the quinoline skeleton have the same meanings as defined above, and $X^{3a}$ and $X^{3b}$, the same or different, represent a halogen atom respectively.

The halogen atom represented by $X^{3a}$ and $X^{3b}$ has the same meaning as defined above.

The reaction between the compound of the formula (2a) and thiourea (4) can be carried out in the presence or absence of a solvent. Examples of the solvent which can be used include alcohols such as methanol, ethanol, propanol, etc.; ethers such as diethyl ether, tetrahydrofuran, dioxane, ethyleneglycol monomethyl ether, etc.; aromatic hydrocarbons such as benzene, toluene, xylene, etc.; ketones such as acetone, methylethylketone, etc.; and DMF, DMSO, HMPA, etc. In the above reaction, the suitable amount of thiourea (4) to be used is usually at least 1 mol amount, preferably 1 to 2 mols, of thiourea (4) per mol of the compound of the formula (2a). The reaction usually is carried out at room temperature to 200° C., preferably room temperature to about 150° C., and completed in about 1 to 5 hours.

The reaction between the intermediate obtained in the above-mentioned reaction and the compound of the formula (3a) can be carried out usually in the presence of a condensing agent. In the above reaction, a basic compound usually is used as the condensing agent. Various known basic compounds can be used. Examples of the basic compound include inorganic bases such as sodium hydroxide, potassium hydroxide, sodium carbonate, potassium carbonate, sodium hydrogencarbonate, potassium hydrogencarbonate, silver carbonate and the like; alkali metals such as sodium, potassium and the like; alcoholates such as sodium methylate, sodium ethylate and the like; and organic bases such as triethylamine, pyridine, N,N-dimethylaniline, N-methylmorpholine, 4-dimethylaminopyridine, DBN, DBU, DABCO and the like. The reaction can be carried out in the absence or presence of a solvent. Any inert solvent which does not adversely influence the reaction can be used. Examples of the solvent include water; alcohols such as methanol, ethanol, propanol, butanol, ethyleneglycol, etc.; ethers such as diethyl ether, tetrahydrofuran, dioxane, monoglyme, diglyme, etc.; ketones such as acetone, methylethylketone, etc.; aromatic hydrocarbons such as benzene, toluene, xylene, etc.; esters such as methyl acetate, ethyl acetate, etc.; aprotic polar solvents such as DMF, DMSO, HMPA, etc.; or a mixed solvent thereof. The reaction is carried out advantageously in the presence of a metal iodide such as sodium iodide, potassium iodide and the like. The ratio of the compound of the formula (3a) to the compound of the formula (2a) in the above-mentioned process is not limited particularly but can be varied widely. The suitable amount of the compound of the formula (3a) is usually 0.5 to 5 mols, preferably 0.5 to 2 mols, of the compound of the formula (3a) per mol of the compound of the formula (2a). The reaction temperature also is not limited particularly, but is usually −30° C. to about 200° C., preferably 0° C. to 160° C. The reaction is completed usually in about 1 to 30 hours.

[Reaction Scheme-4]

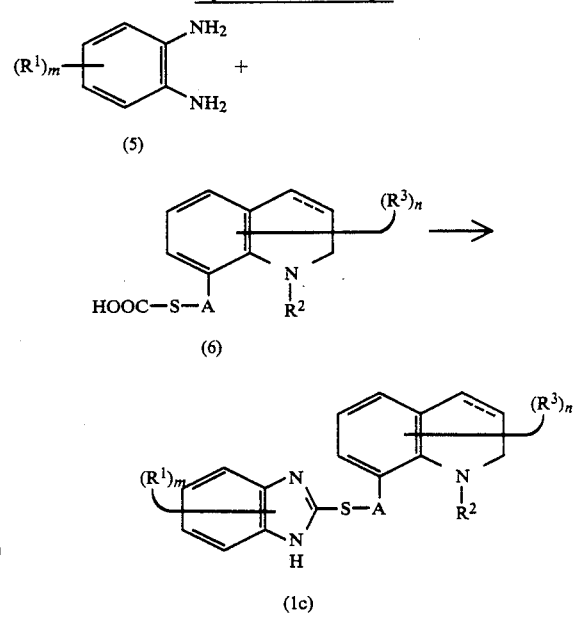

wherein $R^1$, $R^2$, $R^3$, A, m, n and the bond between the 3- and 4-positions of the quinoline skeleton have the same meanings as defined above.

The reaction between the compound of the formula (5) and the compound of the formula (6) can be carried out in the presence of a suitable acid in the absence or presence of a suitable solvent.

Examples of the solvent which can be used include the solvents used in the reaction between the compound of the formula (3a) and the compound formed in the reaction between the compound of the formula (2a) and the compound of the formula (4) in the above-mentioned Reaction Scheme-3.

Examples of the acid which can be used include mineral acids such as hydrochloric acid, sulfuric acid, hydrobromic acid and the like; and organic acids such as benzenesulfonic acid, p-toluenesulfonic acid, methanesulfonic acid and the like.

The suitable amount of the compound of the formula (6) to be used is usually at least equimolar, preferably equimolar to 1.5 mols, of the compound of the formula (6) per mol of the compound of the formula (5). The reaction usually is carried out at room temperature to 150° C., preferably about 50° C. to 120° C., and completed in about 10 minutes to 5 hours.

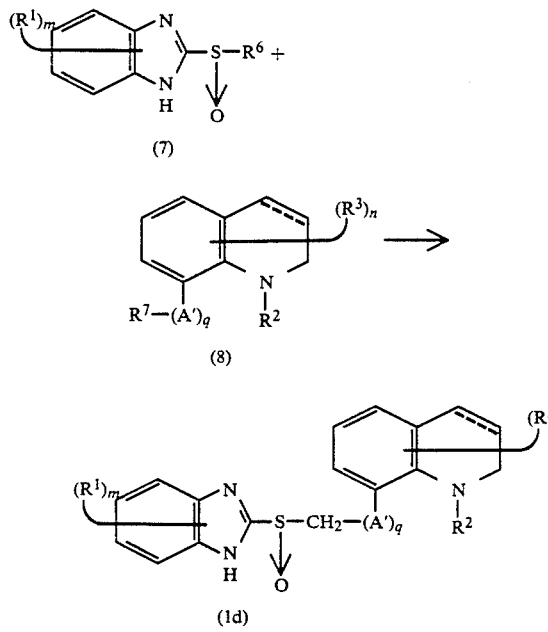

wherein $R^1$, $R^2$, $R^3$, m, n and the bond between the 3- and 4-positions of the quinoline skeleton have the same meanings as defined above, A' is a lower alkylene group and q is an integer of 0 or 1, $R^6$ and $R^7$ represent a halogen atom or a group: —$CH_2$—M (wherein, M is an alkali metal), provided that when $R^6$ is a group: —$CH_2$—M, $R^7$ is a halogen atom, and when $R^6$ is a halogen atom, $R^7$ is a group: —$CH_2$—M, and the group —$CH_2$—(A')$_q$- does not exceed 6 in carbon number.

The alkali metals represented by M in the abovementioned scheme, for example, are sodium, potassium, lithium, etc.

The compound of this invention represented by the formula (1d) can be obtained by allowing the compound of the formula (7) to react with the compound of the formula (8) in a suitable solvent.

Examples of the solvent which can be used include aromatic hydrocarbons such as benzene, toluene, xylene and the like; ethers such as diethyl ether, tetrahydrofuran, dioxane, monoglyme, diglyme and the like; or a mixed solvent thereof.

The suitable amount of the compound of the formula (8) to be used is usually at least equimolar, preferably equimolar to 1.5 mols, of the compound of the formula (8) per mol of the compound of the formula (7). The reaction is carried out usually at room temperature to 150° C., preferably room temperature to about 120° C., and completed in about 1 to 5 hours.

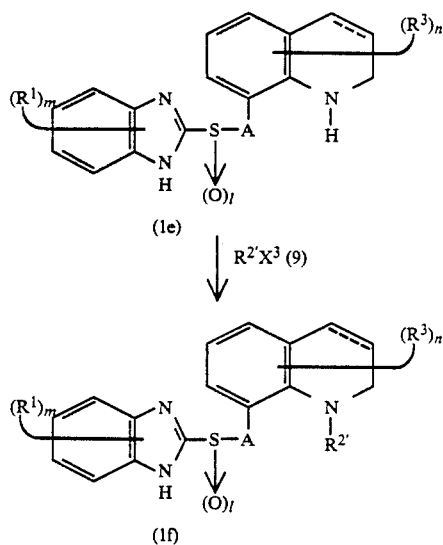

wherein $R^1$, $R^3$, A, l, m, n and the bond between the 3- and 4-positions of the quinoline skeleton, have the same meanings as defined above, $R^{2'}$ represents $R^2$ excluding hydrogen atom, and $X^3$ represents a halogen atom.

The reaction between the compound of the formula (1e) and the compound of the formula (9) can be carried out in the presence of a basic compound in a suitable solvent. Examples of the basic compound which can be used include sodium hydride, potassium hydride, sodium, potassium, sodium amide, potassium amide, sodium hydroxide, potassium hydroxide, sodium carbonate, potassium carbonate, sodium hydrogencarbonate, potassium hydrogencarbonate, alkyl lithiums such as n-butyllithium, etc.; DBN, DBU, DABCO, etc. Examples of the solvent which can be used include ethers such as diethyl ether, tetrahydrofuran, dioxane, ethyleneglycol monomethyl ether, diethyleneglycol dimethyl ether, etc.; aromatic hydrocarbons such as benzene, toluene, xylene, chlorobenzene, etc.; DMF, DMSO, HMPA, aqueous ammonia, etc. or a mixed solvent thereof.

The amount of the compound of the formula (9) is not limited particularly, and usually is at least equimolar, preferably equimolar to 2 mols, of the compound of the formula (9) per mol of the compound of the formula (1e). The reaction is carried out usually at −40° C. to about 150° C., preferably at −40° C. to about 100° C., and generally completed in 30 minutes to about 24 hours. In this reaction, the compound of the formula (9) sometimes reacts with the alkylene group at the α-position from the —S→(O)$_l$ group or with the imidazole ring at 1- or 3-position. These compounds, however, can be easily separated.

[Reaction Scheme-7]

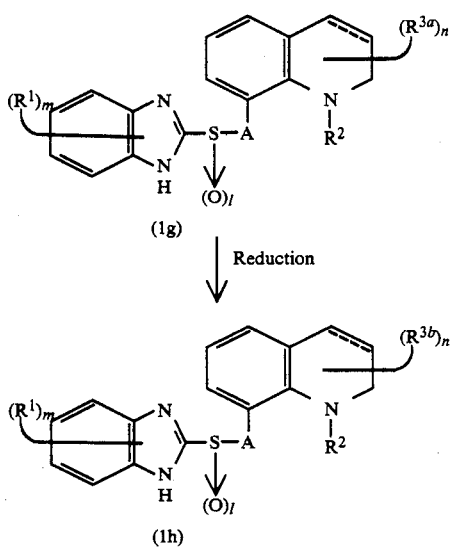

wherein $R^1$, $R^2$, l, m, n, A and the bond between the 3- and 4-positions of the quinoline skeleton have the same meanings as defined above, $R^{3a}$ is an oxo group and $R^{3b}$ is a hydroxy group.

The compound of the formula (1h) can be obtained by subjecting the compound of the formula (1g) to a reduction reaction. The reduction reaction of the compound of the formula (1g) is carried out in a suitable solvent in the presence of a hydride reducing agent. Example of the reducing agent which can be used include sodium borohydride, lithium aluminum hydride, diborane, etc. In the above reaction, the suitable amount of the reducing agent to be used is at least equimolar, preferably equimolar to 10 mols, of the reducing agent per mol of the compound of the formula (1g). Examples of the solvent which can be used include water, lower alcohols such as methanol, ethanol, isopropanol, etc.; and ethers such as tetrahydrofuran, diethyl ether, diglyme, etc. The reaction is carried out usually at $-60°$ C. to 50° C., preferably $-30°$ C. to about room temperature and completed in about 10 minutes to 5 hours. An anhydrous solvent of diethyl ether, tetrahydrofuran, diglyme and the like is used desirably when lithium aluminum hydride or diborane is used as the reducing agent.

[Reaction Scheme-8]

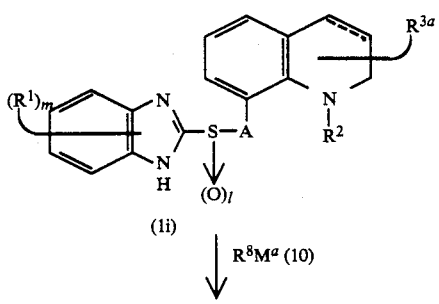

-continued
[Reaction Scheme-8]

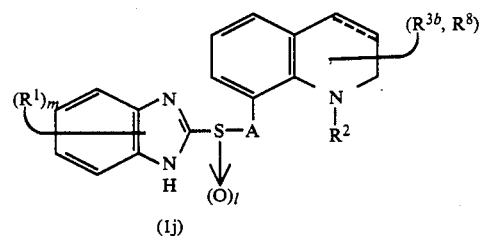

wherein $R^1$, $R^2$, $R^{3a}$, $R^{3b}$, l, m, A and the bond between the 3-and 4-positions of the quinoline skeleton have the same meanings as defined above, $R^8$ is a lower alkyl group, and $M^a$ is lithium or $MgX^3$, where $X^3$ represents a halogen atom. ($R^{3b}$, $R^8$) means that $R^{3b}$ and $R^8$ are attached to the same position of the quinoline skeleton as follows:

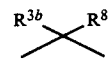

The compound of the formula (1j) can be prepared by allowing the compound of the formula (1i) to react with the compound of the formula (10) in a suitable solvent. The reaction is carried out usually at $-60°$ C. to 50° C., preferably at about $-30°$ C. to room temperature, and completed in about 10 minutes to 5 hours.

In the above reaction, the suitable amount of the compound of the formula (10) which is used is at least equimolar, preferably equimolar to 3 mols, of the compound of the formula (10) per mol of the compound of the formula (1i).

Examples of the solvent which can be used include ethers such as tetrahydrofuran, diethyl ether, diglyme and the like.

The compound of the formula (1i), where the carbonyl group is converted to a lower alkylenedioxy group, can be prepared by allowing the carbonyl group of the quinoline skeleton to react with a lower alkyleneglycol such as ethyleneglycol, trimethyleneglycol, etc. in the presence of a mineral acid such as hydrochloric acid, sulfuric acid, hydrobromic acid, etc., an organic acid such as p-toluenesulfonic acid and in a suitable solvent.

Examples of the solvent which can be used include ethers such as diethyl ether, dioxane, tetrahydrofuran, monoglyme, diglyme and the like; alcohols such as methanol, ethanol, isopropanol and the like; aromatic hydrocarbons such as benzene, toluene, xylene and the like; aliphatic hydrocarbons such as n-hexane, heptane, cyclohexane, ligroin and the like; amines such as pyridine, N,N-dimethylaniline and the like; halogenated hydrocarbons such as chloroform, dichloromethane, carbon tetrachloride and the like; aprotic polar solvents such as DMF, DMSO, HMPA and the like; or a mixed solvent thereof. The reaction is carried out usually at room temperature to 170° C., preferably at room temperature to about 150° C., and completed in about 1 to 7 hours.

The lower alkylenedioxy group-substituted compound obtained in the above reaction can be led to the carbonyl group-substituted compound by subjecting the former to a hydrolysis reaction. The hydrolysis reaction is carried out usually at room temperature to 150° C., preferably at room temperature to 100° C., and completed in about 1 to 24 hours, in the presence of a mineral acid such as hydrogen halides (e.g. hydrochloric acid, hydrobromic acid, etc.), sulfuric acid, phosphoric acid and the like, and in water or in a mixed solvent of water and lower alcohols such as methanol, ethanol, propanol and the like.
[Reaction Scheme-9]
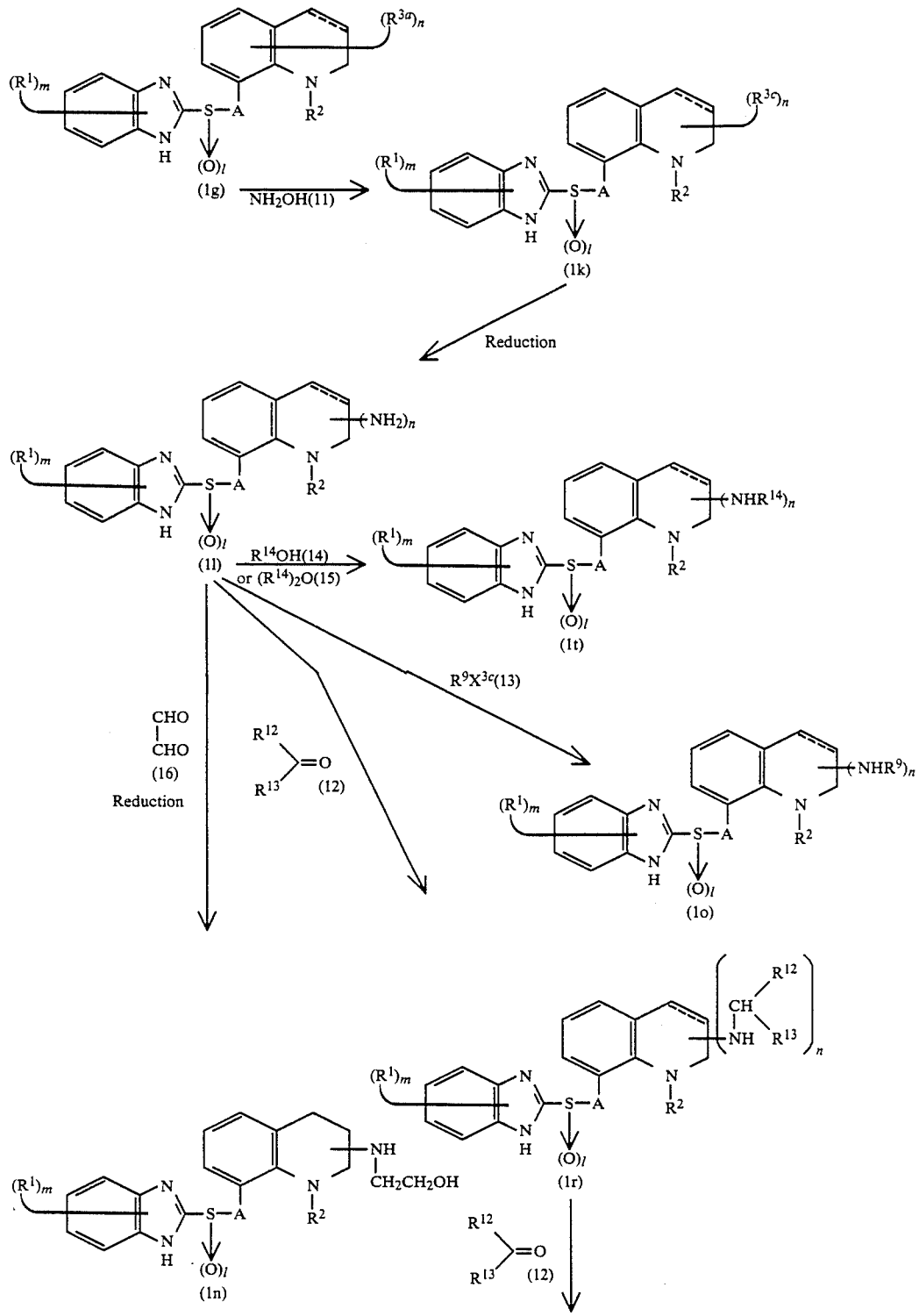

-continued
[Reaction Scheme-9]
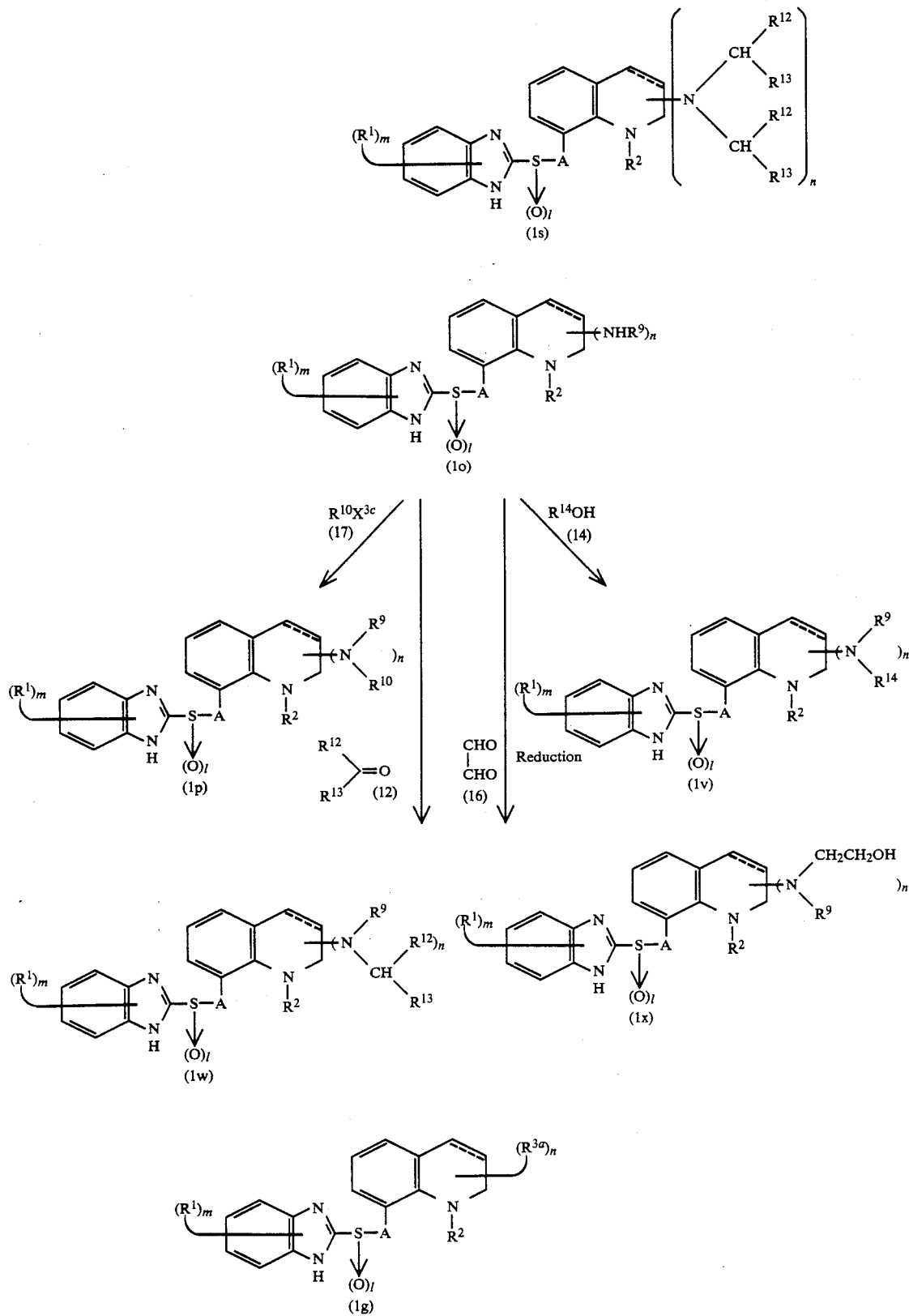

-continued
[Reaction Scheme-9]

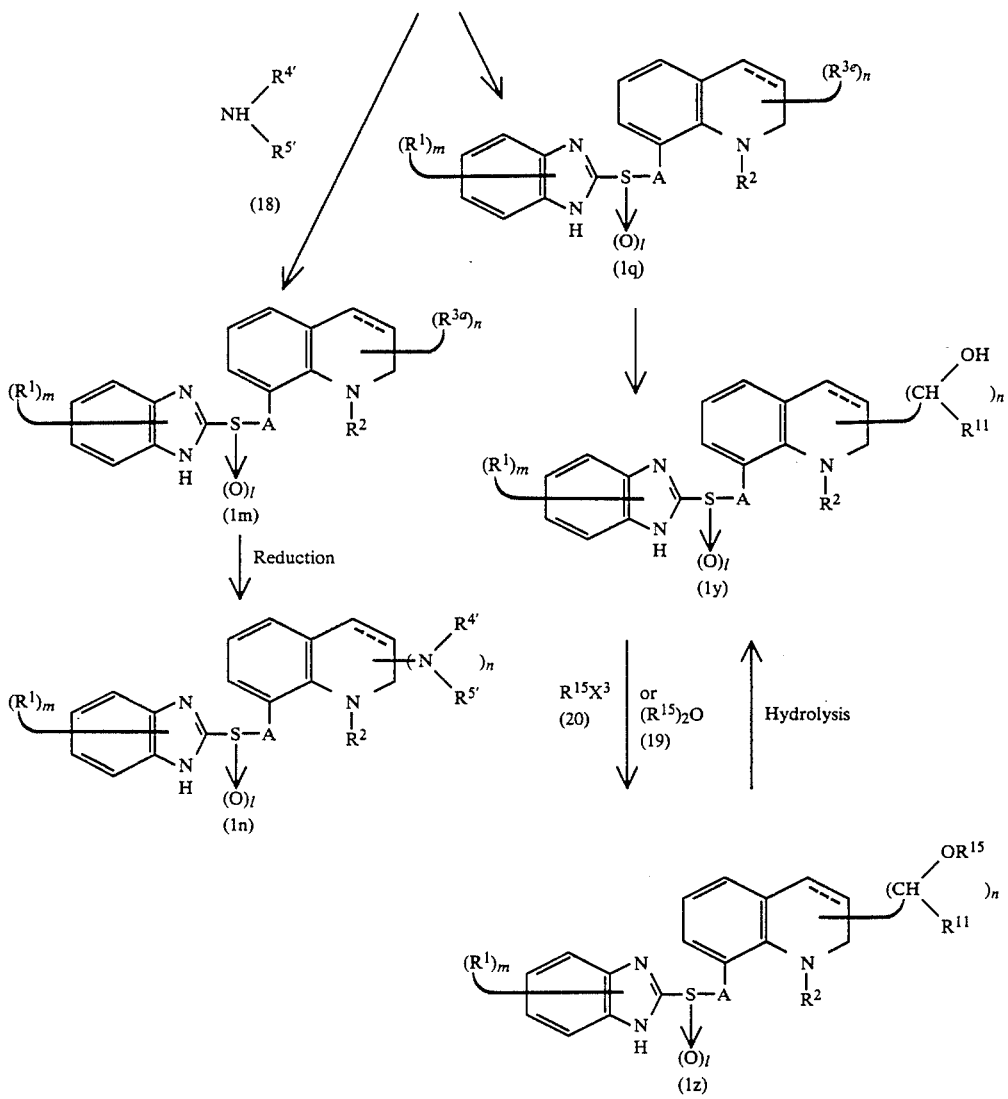

wherein $R^1$, $R^2$, $R^{3a}$, l, m, n, A and the bond between the 3- and 4-positions of the quinoline skeleton have the same meanings as defined above, $X^{3c}$ represents a hydroxy group or a halogen atom, and $R^{4'}$ and $R^{5'}$ represent, the same or different, a hydrogen atom, a lower alkyl group which may have 1 to 3 groups selected from the group consisting of a halogen atom and a lower alkoxy group, a hydroxysubstituted lower alkyl group, a cycloalkyl group, a cycloalkyl lower alkyl group, a lower alkenyl group or a phenyl-lower alkyl group which may have a lower alkoxy group, and $R^{4'}$ and $R^{5'}$ together with the bonding nitrogen atom may form a saturated 5- or 6-membered heterocyclic group which may contain hetero atom(s) consisting of an oxygen atom, a sulfur atom and a nitrogen atom, $R^9$ and $R^{10}$ represent a lower alkyl group which may have 1 to 3 groups selected from the group consisting of a halogen atom and a lower alkoxy group, a hydroxy-substituted lower alkyl group, a cycloalkyl group, a cycloalkyl lower alkyl group, a lower alkenyl group or a phenyl lower alkyl group which may have a lower alkoxy group, $R^{12}$ and $R^{13}$ represent a hydrogen atom or a lower alkyl group, $R^{14}$ represents a cycloalkylcarbonyl group or a lower alkanoyl group, $R^{15}$ represents a lower alkanoyl group, $R^{3c}$ represents a hydroxyimino group, $R^{3d}$ represents the group:

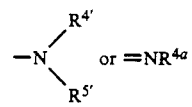

wherein $R^{4'}$ and $R^{5'}$ have the same meanings as defined above, while $R^{4a}$ represents a lower alkyl group which may have 1 to 3 groups selected from the group consisting of a halogen atom and a lower alkoxy group, a hydroxy-substituted lower alkyl group, a cycloalkyl group, a cycloalkyl lower alkyl group, a lower alkenyl group or a phenyl-lower alkyl group which may have a lower alkoxy group, and $R^{3e}$ represents the group: =—$R^{11}$, wherein $R^{11}$ is a lower alkyl group.

The reaction between the compound of the formula (1g) and the compound of the formula (11) can be carried out in a suitable inert solvent and in the presence or absence of a basic compound. Examples of the basic compound which can be used in the reaction include inorganic basic compounds such as sodium hydroxide, potassium hydroxide, sodium carbonate, potassium carbonate, etc.; lower alkanoic acid alkali metal salts such as sodium acetate, etc.; and organic bases such as piperidine, pyridine, triethylamine, DBN, DBU, DABCO, etc. Any inert solvent which does not adversely influence the reaction can be used, for example, water, lower alcohols such as methanol, ethanol, isopropanol, etc.; ethers such as dioxane, tetrahydrofuran, diethyl ether, ethyleneglycol monomethyl ether, etc.; aromatic hydrocarbons such as benzene, toluene, xylene, etc.; halogenated hydrocarbons such as dichloromethane, dichloroethane, chloroform, carbon tetrachloride, etc.; aprotic polar solvents such as DMF, DMSO, HMPA, etc.; or a mixed solvent thereof. The suitable amount of hydroxylamine (11) is usually at least equimolar, preferably equimolar to 5 mols, of hydroxylamine (11) per mol of the compound of the formula (1g). The reaction temperature usually is desirable to be room temperature to 200° C., preferably 50° C. to 150° C., and the reaction is generally completed in about 1 to 10 hours.

The method using a hydride reducing agent can be applied to the reduction of the compound of the formula (1k), preferably, the reduction can be carried out by subjecting to a catalytic hydrogenation in a suitable solvent in the presence of a catalyst. Examples of the solvent which can be used include water; acetic acid; alcohols such as methanol, ethanol, isopropanol, etc.; hydrocarbons such as hexane, cyclohexane, etc.; ethers such as diethyleneglycol dimethyl ether, dioxane, tetrahydrofuran, diethyl ether, etc.; esters such as ethyl acetate, methyl acetate, etc.; aprotic polar solvents such as DMF, etc.; or a mixed solvent thereof. Examples of the catalyst which can be used include palladium, palladium black, palladium carbon, platinum, platinum oxide, copper chromite, Raney nickel, etc. In the above reaction, the amount of the catalyst is generally 0.02 to 1 time of the catalyst per the amount of the compound of the formula (1k). The reaction temperature is usually about −20° C. to 100° C., preferably about 0° C. to 70° C. and the hydrogen pressure is usually 1 to 10 atmospheric pressure. The reaction is completed generally in about 0.5 to 20 hours.

Examples of the hydride reducing agent used in the reaction include lithium aluminum hydride, sodium borohydride, diborane, etc. The amount of the reducing agent to be used is usually at least equimolar, preferably equimolar to 10 mols, of the reducing agent per mol of the compound of the formula (1k). The suitable solvent such as water, lower alcohols, e.g. methanol, ethanol, isopropanol, etc.; ethers, e.g. tetrahydrofuran, diethyl ether, diglyme, etc.; and acetic acid is usually used in this reducing reaction, the reaction usually is carried out at about 0° C. to 200° C., preferably 0° C. to 170° C., and completed in about 10 minutes to 10 hours. An anhydrous solvent of diethyl ether, tetrahydrofuran, diglyme and the like is used desirably when lithium aluminum hydride or diborane is used as the reducing agent.

The reaction between the compound of the formula (1g) and the compound of the formula (18) is carried out without solvents or in a suitable solvent in the presence or absence of a dehydrating agent. Examples of the solvent which can be used include alcohols such as methanol, ethanol, isopropanol, etc.; aromatic hydrocarbons such as benzene, toluene, xylene, etc.; and aprotic polar solvents such as DMF, dimethyl acetamide, N-methylpyrrolidone, etc. Examples of the dehydrating agent include drying agents such as molecular sieves and the like used for the dehydration of ordinary solvents; mineral acids such as hydrochloric acid, sulfuric acid, boron trifluoride and the like; and organic acids such as p-toluenesulfonic acid and the like. The reaction is carried out usually at room temperature to 250° C., preferably at about 50° C. to 200° C., and generally completed in about 1 to 48 hours. The amount of the compound of the formula (18) to be used is not limited particularly but it is usually at least equimolar, preferably large excess, of the compound of the formula (18) per mol of the compound of the formula (1g). The dehydrating agent is used in large excess amount when the drying agent is employed, or in catalytic amount when the acid is employed. The compound of the formula (1m) thus obtained may be used, without isolation, in the next reduction reaction.

Various methods are applicable to the reduction reaction of the compound of the formula (1m). For example, the reduction method employing a hydride reducing agent is used suitably. Examples of the hydride reducing agent which can be used include sodium aluminum hydride, sodium borohydride, diborane, etc. Usually, the amount of the hydride reducing agent is at least equimolar, preferably equimolar to 10 mols, of the hydride reducing agent per mol of the compound of the formula (1m). The reduction reaction is conducted in a suitable solvent, for example, water, lower alcohols such as methanol, ethanol, isopropanol, etc.; and ethers such as tetrahydrofuran, diethyl ether, diglyme, etc., and carried out usually at about −60° C. to 50° C., preferably at −30° C. to room temperature and completed in about 10 minutes to 5 hours. When lithium aluminum hydride or diborane is used as the reducing agent, an anhydrous solvent of diethyl ether, tetrahydrofuran, diglyme and the like is used desirably.

The reaction that converts the compound of the formula (1g) to the compound of the formula (1q) is called Witting Reaction, and the compound of the formula (1q) can be obtained by allowing the compound of the formula (1g) to react with Witting reagents represented, for example, by the following formulas:

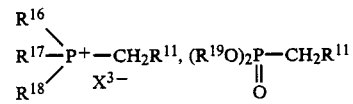

wherein $R^{16}$, $R^{17}$, and $R^{19}$ represent respectively a lower alkyl group or a phenyl group, and $R^{11}$ and $X^3$ have the same meanings as defined above.

The reaction is conducted in a solvent in the presence of a basic compound. Examples of the basic compound which can be used include inorganic bases such as sodium, potassium, sodium hydride, sodium amide, sodium hydroxide, potassium hydroxide, sodium carbonate, potassium carbonate, sodium hydrogencarbonate, etc.; metal alcoholates such as sodium methylate, sodium ethylate, etc.; lithium salts such as methyllithium, n-butyllithium, phenyllithium, etc.; and organic bases such as pyridine, piperidine, quinoline, triethylamine, N,N-dimethylaniline, etc. Any solvent which does not adversely influence the reaction can be used. Examples of the solvent include ethers such as diethyl ether, dioxane, tetrahydrofuran, monoglyme, diglyme and the like; aromatic hydrocarbons such as benzene, toluene, xylene and the like; aliphatic hydrocarbons such as n-hexane, pentane, heptane, cyclohexane and the like; amines such as pyridine, N,N-dimethylaniline and the like; and aprotic polar solvents such as DMF, DMSO, HMPA and the like. The reaction is carried out usually at $-30°$ C. to 150° C., preferably at about $-20°$ C. to 120° C. The reaction generally is completed in about 0.5 to 15 hours. The suitable amount of Witting reagent is at least equimolar, preferably equimolar to 5 mols, of the Witting reagent per mol of the compound of the formula (1g).

The reaction between the compound of the formula (1l) and the compound of the formula (13) or the reaction between the compound of the formula (1o) and the compound of the formula (17) is carried out in the presence or absence of a dehydrohalogenation agent in a suitable solvent. A basic compound usually is used as the dehydrohalogenation agent. Examples of the basic compound include organic bases such as triethylamine, trimethylamine, pyridine, dimethylaniline, N-methylmorpholine, 4-dimethylaminopyridine, DBN, DBU, DABCO and the like; and inorganic bases such as potassium carbonate, sodium carbonate, potassium hydrogencarbonate, sodium hydrogencarbonate, sodium hydroxide, potassium hydroxide, sodium hydride, potassium hydride, silver carbonate, alkali metal alcoholates, e.g. sodium methylate, sodium ethylate and the like.

In case excess amounts of the compound of the formula (1l) or (1o) is employed, it can be used as the dehydrohalogenation agent.

Examples of the solvent which can be used include halogenated hydrocarbons such as methylene chloride, chloroform, dichlorethane, etc.; aromatic hydrocarbons such as benzene, toluene, xylene, etc.; ethers such as diethyl ether, diisopropyl ether, tetrahydrofuran, dimethoxyethane, etc.; esters such as methyl acetate, ethyl acetate, etc.; aprotic polar solvents such as DMF, DMSO, HMPA, etc.; water; alcohols such as methanol, ethanol, propanol, butanol, 3-methoxy-1-butanol, ethylcellosolve, methylcellosolve, etc.; pyridine, acetone, acetonitrile, etc., or a mixed solvent of more than two kinds thereof. The ratio of the compound of the formula (1l) or (1o) to the compound of the formula (13) or (17) is not limited particularly but can be selected from a wide range. Usually, the latter is used in at least equimolar, preferably equimolar to 5 mols, amount per mol of the former. The reaction usually is carried out at about $-30°$ C. to 180° C., preferably at about 0° C. to 150° C. and is generally completed in 5 minutes to 30 hours.

In the reaction between the compound of the formula (1l) and the compound of the formula (13), the compound of the formula (13) may react with the alkylene group at the α-position from the $-S\rightarrow(O)_l$ group of the compound of the formula (1l) or with the imidazole ring at the 1- or 3-position, or when $R^2$ of the compound of the formula (1l) is a hydrogen atom, may react at the 1-position of the hydroquinoline ring, and a group: $-N(R^9)_2$ may be formed by reacting 2 moles of the compound of the formula (13) with the amino group of the compound of the formula (1l). These compounds, however, can be separated easily.

Likewise, in the reaction between the compound of the formula (1o) and the compound of the formula (17), the compound of the formula (17) may react with the alkylene group at the α-position from the $-S\rightarrow(O)_l$ group of the compound of the formula (1o) or with the imidazole ring at the 1- or 3- position, or when $R^2$ of the compound of the formula (1o) is a hydrogen atom, reacts at the 1-position of the hydroquinoline ring. These compounds, however, can be separated easily.

The reaction between the compound of the formula (1l) or (1r) and the compound of the formula (12) is carried out without solvents or in a suitable solvent in the presence of a reducing agent. Examples of the solvent which can be used include water; alcohols such as methanol, ethanol, isopropanol, etc.; acetic acid; ethers such as dioxane, diethyl ether, diglyme, tetrahydrofuran, etc.; and aromatic hydrocarbons such as benzene, toluene, xylene, etc. Examples of the reduction process include a process employing formic acid, a hydride reducing agent such as sodium borohydride, sodium cyanoborohydride, lithium aluminum hydride, etc.; a catalytic reducing process employing a catalytic reducing catalyst such as palladium black, palladium carbon, platinum oxide, platinum black, Raney nickel; and so on. When formic acid is used as the reducing agent, the suitable reaction temperature usually is room temperature to 200° C., preferably about 50° C. to 150° C., and the reaction is completed in about 1 to 10 hours. The formic acid is used desirably in a large excess amount as compared with the amount of the compound of the formula (1l) or (1r).

When the hydride reducing agent is employed, the suitable reaction temperature usually is $-30°$ C. to 100° C., preferably about 0° C. to 70° C., and the reaction is completed in about 30 minutes to 12 hours. The amount of the reducing agent is usually equimolar to 20 mols, preferably 1 to 5 mols, of the reducing agent per mol of the compound of the formula (1l) or (1r). Particularly, when lithium aluminum hydride is used as the reducing agent, it is desirable that ethers such as diethyl ether, dioxane, tetrahydrofuran, diglyme, and the like; aromatic hydrocarbons such as benzene, toluene, xylene and the like are used as solvents.

When the catalytic reducing catalyst is employed, it is desirable that the reaction is carried out usually under hydrogen atmosphere of ordinary pressure to 20 atmospheric pressure, preferably ordinary pressure to 10 atmospheric pressure, and usually at $-30°$ C. to 100° C., preferably at 0° C. to 60° C. The reaction is completed usually in 1 to 12 hours. The amount of the catalyst to the compound of the formula (1l) or (1r) is usually 0.1 to 40% by weight, preferably 1 to 20% by weight. The amount of the compound of the formula (12) is usually at least equimolar, preferably equimolar to large excess, of the compound of the formula (12) per mol of the compound of the formula (1l) or (1r).

The reaction between the compound of the formula (1l) and the compound of the formula (15) can be carried out under the conditions similar to those of the reaction between the compound of the formula (1l) and the compound of the formula (13) or the reaction between the compound of the formula (1o) and the compound of the formula (17).

The reaction between the compound of the formula (1l) or (1o) and the compound of the formula (14) is an ordinary amide-forming reaction, to which the conditions for known amide-forming reaction can be readily applied. Examples of the amide-forming reaction include;

(a) the mixed acid anhydride method, wherein the carboxylic acid of the formula (14) is reacted with an alkyl halocarboxylic acid to form a mixed acid anhydride, which is then reacted with the compound of the formula (1l) or (1o), (b) the active ester method, wherein the carboxylic acid of the formula (14) is converted into an active ester such as p-nitrophenyl ester, N-hydroxysuccinimide ester, 1-hydroxybenzotriazole ester, etc., which is then reacted with the compound of the formula (1l) or (1o), (c) the carbodiimide method, wherein the compound of the formula (1l) or (1o) is condensed with the carboxylic acid of the formula (14) in the presence of an activating agent such as dicyclohexylcarbodiimide, carbonyl diimidazole, etc., and (d) other methods, wherein the carboxylic acid of the formula (14) is converted into a carboxylic acid anhydride with a dehydrating agent such as acetic anhydride, etc., followed by reacting the product with the compound of the formula (1l) or (1o); the ester of carboxylic acid of the formula (14) and a lower alcohol is reacted with the compound of the formula (1l) or (1o) at elevated temperature and pressure; and an acid halide of carboxylic acid of the formula (14), i.e. a carboxylic halide, is reacted with the compound of the formula (1l) or (1o).

The mixed acid anhydride used in the mixed acid anhydride method can be prepared in accordance with conventional Schötten-Baumann reaction and subjected, usually without isolation, to reaction with the compound of the formula (1l) or (1o) to give the compound of the formula (1t) or (1v). The Schötten-Baumann reaction is carried out in the presence of a basic compound. Any conventional basic compounds commonly used in Schötten-Baumann reaction can be used. Examples of the basic compound include organic bases such as triethylamine, trimethylamine, pyridine, dimethylaniline, N-methylmorpholine, DBN, DBU, DABCO, etc.; inorganic bases such as potassium carbonate, sodium carbonate, potassium hydrogencarbonate, sodium hydrogencarbonate. The reaction is carried out at $-20°$ C. to 100° C., preferably 0° C. to 50° C., in 5 minutes to 10 hours, preferably 5 minutes to 2 hours. The reaction between the resulting mixed acid anhydride and the compound of the formula (1l) or (1o) is carried out at $-20°$ C. to 150° C., preferably 10° C. to 50° C., in 5 minutes to 10 hours, preferably 5 minutes to 5 hours. The mixed acid anhydride method generally is carried out in a solvent. Any solvents conventionally used in the mixed acid anhydride method can be used. Examples of the solvent include halogenated hydrocarbons such as methylene chloride, chloroform, dichloroethane, etc.; aromatic hydrocarbons such as benzene, toluene, xylene, etc.; ethers such as diethyl ether, tetrahydrofuran, dimethoxyethane, etc.; esters such as methyl acetate, ethyl acetate, etc.; and aprotic polar solvents such as DMF, DMSO, HMPA, etc. Examples of the alkyl halocarboxylate which can be used in the mixed acid anhydride method include methyl chloroformate, methyl bromoformate, ethyl chloroformate, ethyl bromoformate, isobutyl chloroformate, etc. The carboxylic acid of the formula (14), the alkyl halocarboxylate, and the compound of the formula (1l) or (1o) are usually used in an equimolar amount each. However, the alkyl halocarboxylate and the carboxylic acid of the formula (14) may be used in 1 to 1.5 mols amounts per mol of the compound of the formula (1l) or (1o).

When the method of allowing the compound of the formula (1l) or (1o) to react with the halide of the carboxylic acid of the formula (14) is employed, the reaction is carried out in the presence or absence of a basic compound in a suitable solvent. As for the basic compound, various known basic compounds can be used. Examples of the basic compound include sodium hydroxide, potassium hydroxide, sodium hydride, potassium hydride, etc. in addition to those used in the above-mentioned Schötten-Baumann reaction. Examples of the solvent which can be used include alcohols such as methanol, ethanol, propanol, butanol, 3-methoxy-1-butanol, ethylcellosolve, methylcellosolve, etc.; pyridine, acetone, etc. in addition to those used in the above-mentioned Schötten-Baumann reaction. Proportion of the compound of the formula (1l) or (1o) to the carboxylic acid halide is not limited particularly but can be varied appropriately. The suitable amount of the latter is usually about 0.1 to 10 mols, preferably 0.4 to 5 mols, of the latter per mol of the former. The reaction is proceeded at 20° C. to 180° C., preferably at 0° C. to 150° C., and generally completed in 5 minutes to 30 hours.

The reaction between the compound of the formula (1l) or (1o) and glyoxal (16) is carried out in a suitable solvent. As for the solvent, all of the solvents used in the above-mentioned reaction between the compound of the formula (1g) and the compound of the formula (18) can be used. The reaction is carried out usually at 0° C. to 100° C., preferably at about 0° C. to 70° C., and completed in about 1 to 5 hours. The intermediate thus obtained may be used, without isolation, in the next reduction reaction. The reduction reaction can be carried out under the conditions similar to those of the reduction reaction that forms the compound of the formula (1h) from the compound of the formula (1g) in the above-mentioned Reaction Scheme-7.

The reaction between the compound of the formula (1o) and the compound of the formula (12) can be carried out under the conditions similar to those of the reaction between the compound of the formula (1l) or (1r) and the compound of the formula (12) mentioned before.

The reaction that converts the compound of the formula (1q) to the compound of the formula (1y) can be carried out in the presence of a hydroboration reagent in a suitable solvent. Examples of the hydroboration reagent which can be used include various types of borane derivatives such as borane-tetrahydrofurane complex, borane-dimethylsulfide complex, thexylborane, monochloroborane, dichloroborane, disamylborane, dicyclohexylborane, diisopinocampheylborane, 9-borabicyclo[3.3.1]nonane, 3,5-dimethylborinane, catecholborane. Examples of the solvent which can be used include ethers such as tetrahydrofuran, diethyl ether, dioxane and the like. In the above reaction, the suitable amount of the hydroboration reagent is equimolar to 10 mols, preferably equimolar to 5 mols, of the hydroboration reagent per mol of the compound of the formula (1q). The reaction is carried out usually at 0° C. to 100° C., preferably at about room temperature to 80° C., and completed in about 1 to 5 hours. The desired compounds of the formula (1y) can be obtained by oxidizing the resulting intermediate with hydrogen peroxide. The reaction is carried out usually in 1 to 5 hours at 0° C. to 100° C., preferably at room temperature to 80° C., in a basic aqueous solution such as sodium hydroxide aqueous solution and the like. The suitable amount of the hydrogen peroxide to be used is usually in a large excess.

The reactions of the compound of the formula (1y) with the compounds of the formulas (19) and (20) can be carried out respectively under the conditions similar to those of the reaction between the compound of the formula (11) and the compound of the formula (14) and the reaction between the compound of the formula (11) and the compound of the formula (15).

The hydrolysis reaction of the compound of the formula (1z) is carried out usually at room temperature to 150° C., preferably at room temperature to 100° C., in the presence of an acidic compound or a basic compound in a solvent and completed in about 1 to 24 hours. Examples of the acidic compound include mineral acid such as hydrogen halide [e.g. hydrochloric acid, hydrobromic acid, etc.]; sulfuric acid, phosphoric acid, etc. Examples of the basic compound include alkali metal hydroxides such as sodium hydroxide, potassium hydroxide, etc.; and alkali metal carbonates such as sodium carbonate, potassium carbonate, etc.; alkali metal hydrogencarbonates such as sodium hydrogencarbonate, potassium hydrogencarbonate and so on. Examples of the solvent include water or a mixed solvent of water and a lower alcohol such as methanol, ethanol, propanol, etc.

In the compounds of the formulas (1a) to (1z) in the above-mentioned Reaction Schemes 1 to 9, when $R^2$ or $R^{2'}$ is a lower alkynyl group having a tri-lower alkylsilyl group, $R^2$ or $R^{2'}$ in the compounds of the formulas (1a) to (1z) can be converted to a lower alkynyl group by a desilylation reaction.

The desilylation reaction is carried out in a suitable solvent and in the presence of a tetraammonium halide such as tetrabutylammonium fluoride, etc.; fluorine compounds such as hydrofluoric acid, pyridinium hydrofluoride, tetrabutylammonium fluoride, etc.; mineral acids such as hydrochloric acid, hydrobromic acid, etc.; organic acids such as acetic acid, etc.; and inorganic bases such as potassium carbonate, sodium hydroxide, potassium hydroxide, etc. The reaction is carried out usually at —20° C. to 50° C., preferably at about —20° C. to room temperature and completed in about 10 minutes to 5 hours. Examples of the solvent which can be used include ethers such as tetrahydrofuran, diethyl ether, dioxane and the like.

In the above reaction, the suitable amount of the desilylating agent is a large excess amount to the starting materials.

The carbonyl group of the compounds of the formulas (1t) and (1v) can be converted to a —CH$_2$— group by subjecting the compounds to a reduction reaction.

The reduction reaction is carried out in a suitable solvent in the presence of a hydride reducing agent. Examples of the reducing agent which can be used include sodium borohydride, lithium aluminum hydride, diborane, etc. In the above reaction, the suitable amount of the reducing agent to be used is at least equimolar, preferably equimolar to 3 mols, of the reducing agent per mol of the starting materials. As for the solvent, there can be used, for example, water, lower alcohols such as methanol, ethanol, isopropanol, etc.; and ethers such as tetrahydrofuran, diethyl ether, diglyme, etc. The reaction is carried out usually at —60° C. to 100° C., preferably at about —30° C. to 80° C. and completed in about 10 minutes to 5 hours. Use of anhydrous solvent of diethyl ether, tetrahydrofuran and diglyme is desirable when lithium aluminum hydride or diborane is used as the reducing agent.

The compound of the formula (3) which is used as the starting material in Reaction Scheme-1 partially includes a new compound which is produced, for example, by the processes of the following Reaction Schemes 10 and 11:

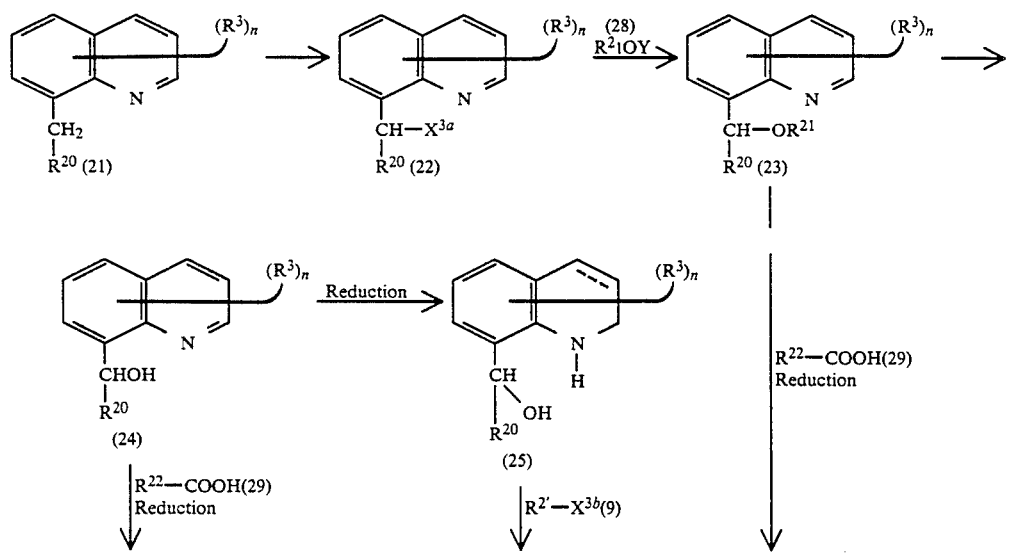

-continued
[Reaction Scheme-10]

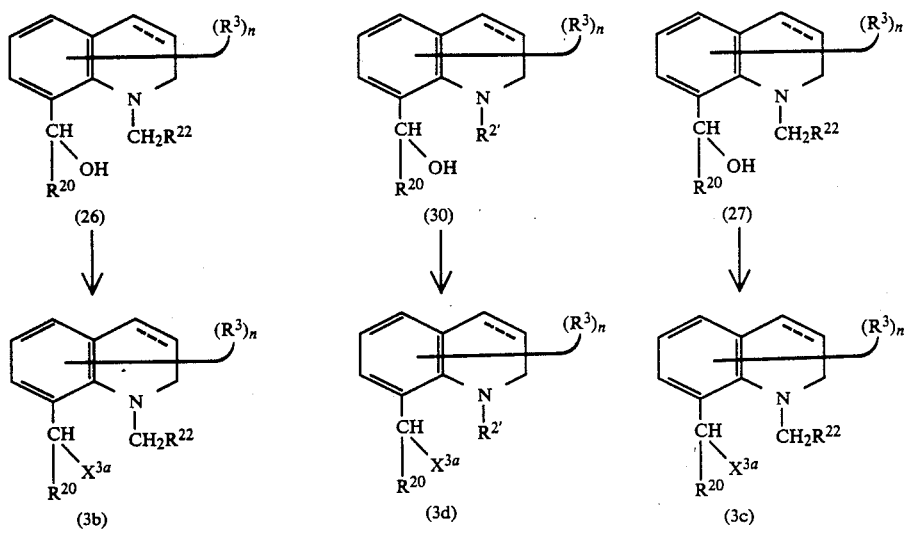

wherein $R^{2'}$, $R^3$, $X^{3a}$, $X^{3b}$, n and the bond between the 3- and 4-positions of the quinoline skeleton have the same meanings as defined above, $R^{20}$ and $R^{22}$ represent respectively a hydrogen atom or a lower alkyl group, $R^{21}$ represents a lower alkanoyl group, and Y represents a hydrogen atom or alkali metals such as sodium, potassium and the like.

The halogenation reaction that forms the compound of the formula (22) from the compound of the formula (21) is carried out by treating the compound of the formula (21) with a halogenating agent in a suitable solvent. Examples of the halogenating agent which can be used include halogen molecules such as chlorine, bromine, etc.; N-halogenosuccinimides such as N-bromosuccinimide, N-chlorosuccinimide, etc.; sulfinyl chloride; and copper halides such as copper chloride, copper bromide, etc.

Examples of the solvent which can be used include halogenated hydrocarbons such as dichloromethane, dichloroethane, chloroform, carbon tetrachloride, etc.; ethers such as diethyl ether, tetrahydrofuran, dioxane, etc.; acetic acid, etc.

The suitable amount of the halogenating agent is equimolar to excess, preferably equimolar to 1.2 mols, of the halogenating agent per mol of the compound of the formula (21).

The reaction is usually proceeded at about 0° C. to the boiling point of the solvent, preferably at room temperature to 100° C. and completed generally in about 1 to 10 hours. Radical reaction initiators such as peroxides, for example, benzoyl peroxide, hydrogen peroxide, etc. may be used in this reaction.

The reaction between the compound of the formula (22) and the compound of the formula (28) is carried out in the presence or absence of a basic compound in a suitable solvent.

The reaction is carried out usually at room temperature to 200° C., preferably at room temperature to 150° C., and completed in about 1 to 15 hours.

Examples of the solvent which can be used in the above reaction include lower alcohols such as methanol, ethanol, isopropanol, etc.; ethers such as diethyl ether, tetrahydrofuran, dioxane, ethyleneglycol monomethyl ether, diethyleneglycol dimethyl ether, etc.; aromatic hydrocarbons such as benzene, toluene, xylene, etc.; ketones such as acetone, methylethylketone, etc.; and polar solvents such as DMF, DMSO, HMPA, acetic anhydride, etc.

Examples of the basic compound which can be used include inorganic bases such as sodium hydroxide, potassium hydroxide, sodium carbonate, potassium carbonate, sodium hydrogencarbonate, potassium hydrogencarbonate, silver carbonate, etc.; alkali metals such as sodium, potassium, etc.; sodium amide; sodium hydride; alkali metal alcoholates such as sodium methylate, sodium ethylate, potassium ethylate, etc.; and organic bases such as triethylamine, tripropylamine, pyridine, quinoline, N,N-dimethylaniline, N-methylmorpholine, etc.

The suitable amount of the compound of the formula (28) is at least equimolar, preferably equimolar to 5 mols, of the compound of the formula (28) per mol of the compound of the formula (22).

The hydrolysis reaction that produces the compound of the formula (24) from the compound of formula (23) can be carried out under conditions similar to those of the hydrolysis reaction of the compound of the formula (1z) in the above-mentioned Reaction Scheme-9.

The reduction reaction which converts the compound of the formula (24) to the compound of the formula (25) is usually carried out by means of a catalytic reduction in the presence of a suitable reducing catalyst Examples of the reducing catalyst which can be used include conventional catalytic reducing catalysts such as platinum, platinum oxide, palladium black, palladium carbon, Raney nickel and the like. The amount of the reducing catalyst to the compound of the formula (24) is usually in the range of about 0.2 to 0.5 time per weight of the compound of the formula (24). The catalytic reduction is carried out, in a solvent, for example, water, methanol, ethanol, isopropanol, diethyl ether, tetrahydrofuran and dioxane under the hydrogen atmosphere of 1 to 10 kg/cm², preferably 1 to 5 kg/cm² at −30° C. to the boiling point of the solvent, preferably at about 0° C. to 70° C. while a well stirring.

The reduction process employing a hydride reducing agent, for example, is suitably applied to the reduction of the compound of the formula (24) in the presence of the compound of the formula (29). In the above reaction, examples of the hydride reducing agent which can be used include diborane; aluminum hydride metal salts such as sodium aluminum hydride, etc.; alkyl aluminum such as lithium tri-tert-butoxyaluminum hydride, diisobutylaluminum hydride, etc.; and boron compounds such as sodium borohydride, (1,1-dimethyl-1-diisopropylmethyl)borohydride, sodium cyanoborohydride, etc. The suitable amount of the reducing agent is at least about equimolar, preferably about equimolar to 5 mols, of the reducing agent per mol of the compound of the formula (24). The reduction reaction, for example, is carried out in a suitable solvent, for example, ethers such as diethyl ether, tetrahydrofuran, diglyme, etc.; aliphatic hydrocarbons such as n-hexane, n-octane, etc.; and aromatic hydrocarbons such as benzene, toluene, xylene, etc., usually at about −75° C. to 50° C., preferably at −75° C. to room temperature, and completed in about 10 minutes to 10 hours. When the boron compound is used as the reducing agent, water, alcohols such as methanol, ethanol, isopropanol, and the like or the compound of the formula (29) may be used as the solvents in addition to the above-mentioned solvents. When aluminum hydride metal salts etc. are used as the reducing agents, use of anhydrous solvents of diethyl ether, tetrahydrofuran and diglyme is desirable.

In the above reaction, the compound of the formula (29) is used usually in large excess amounts as compared with the compound of the formula (24).

The reduction reaction which converts the compound of the formula (23) to the compound of the formula (27) can be carried out in the presence of an organic acid of the formula (29) such as formic acid, acetic acid, propionic acid under the conditions similar to those of the above-mentioned reduction reaction which converts the compound of the formula (24) to the compound of the formula (26). In this reaction, the organic acid is used preferably in large excess amounts.

The reaction between the compound of the formula nation reaction of the compounds of the formulas (26), (30) and (27). The halogenation reaction, for example, is carried out by the reaction of the compound of the formula (26), (30) or (27) with a halogenating agent in a suitable inert solvent or without solvents. Examples of the halogenating agent which can be used include hydrogen halide such as hydrochloric acid, hydrobromic acid, etc.; N,N-diethyl-1,2,2-trichlorovinylamide, phosphorus pentachloride, phosphorus pentabromide, phosphorus oxychloride, thionylchloride, etc. As for the inert solvent, examples of the inert solvent which can be used include ethers such as dioxane, tetrahydrofuran, etc.; and halogenated hydrocarbons such as chloroform, methylene chloride, carbon tetrachloride, etc. The amount of the halogenating agent is at least equimolar, usually in excess, of the halogenating agent per mol of the compound of the formula (26), (30) or (27). The reaction is carried out usually at 0° C. to 150° C., preferably at 0° C. to 80° C., and completed in about 10 minutes to 6 hours.

In the reduction reactions which convert the compound of the formula (23) to the compound of the formula (27), the compound of the formula (24) to the compound of the formula (25), and the compound of the formula (24) to the compound of the formula (26), a mixture of the compound with the quinoline skeleton reduced at the 1-, 2-, 3- and 4-positions and the compound with the quinoline skeleton reduced at the 1- and 2-position only may be formed. These compounds, however, can be separated readily. In the above reduction reaction, the compounds with the quinoline skeleton reduced at the 1- and 2-positions only may be also formed preferentially. In this case, the compounds with the quinoline skeleton reduced at the 1-, 2-, 3- and 4-positions can be obtained by reducing them under the same conditions respectively Furthermore, depending on the reduction conditions, the compounds with the quinoline skeleton reduced at the 1-, 2-, 3- and 4-positions may be formed preferentially.

[Reaction Scheme-11]

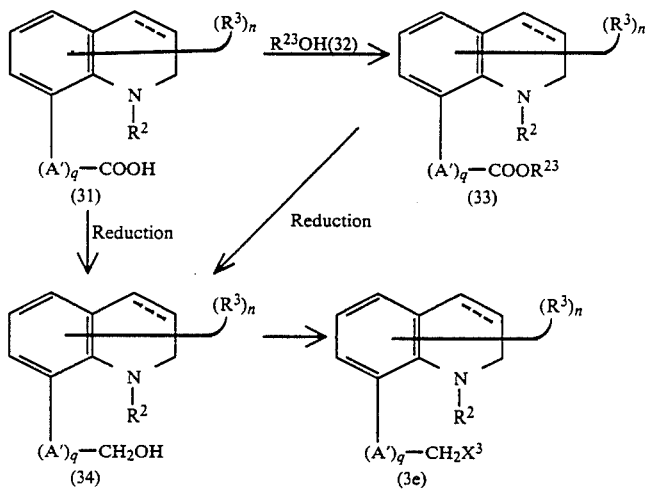

(25) and the compound of the formula (9) can be carried out, for example, under the conditions similar to those of the reaction between the compound of the formula (1e) and the compound of the formula (9) in Reaction Scheme-6.

Any of the conventional reaction conditions for halogenation of hydroxy group can be applied to the halogenation reaction of the compounds of the formulas (26), wherein $R^2$, $R^3$, n, A', q, $X^3$ and the bond between the 3- and 4-positions of the quinoline skeleton have the same meaning as defined above, and $R^{23}$ represents a lower alkyl group, provided that the group $-(A')_q CH_2-$ does not exceed 6 in carbon number.

The esterification reaction between the compound of the formula (31) and the compound of the formula (32) can be carried out under conditions of conventional esterification reactions, for example, (1) a process carried out in a suitable solvent in the presence of a dehydrating agent, (2) a process carried out in a suitable solvent in the presence of an acid or a basic compound, etc.

Examples of the solvent which can be used in above process (1) include halogenated hydrocarbons such as dichloromethane, chloroform, dichloroethane, carbon tetrachloride, etc.; aromatic hydrocarbons such as benzene, toluene, xylene, etc.; ethers such as diethyl ether, tetrahydrofuran, dioxane, ethyleneglycol monomethyl ether, dimethoxyethane, etc.; and aprotic polar solvents such as DMF, DMSO, HMPA, etc. Examples of the dehydrating agent which can be used include dicyclohexylcarbodiimide, carbonyl diimidazole, etc. The suitable amount of the alcohol of the formula (32) is at least equimolar, preferably equimolar to 1.5 mols, of the alcohol of the formula (32) per mol of the compound of the formula (31). The suitable amount of the dehydrating agent is at least equimolar, preferably equimolar to 1.5 mols, of the dehydrating agent per mol of the compound of the formula (31). The reaction is carried out usually at room temperature to 150° C., preferably at 50° C. to 100° C., and completed in about 1 to 10 hours.

Examples of the acid which can be used in above process (2) include inorganic acids such as hydrogen chloride, sulfuric acid, phosphoric acid, polyphosphoric acid, boron trifluoride, perchloric acid, etc.; organic acids such as trifluoroacetic acid, trifluoromethanesulfonic acid, naphthalenesulfonic acid, p-toluenesulfonic acid, benzenesulfonic acid, ethanesulfonic acid, etc.; acid anhydrides such as trichloromethanesulfonic acid anhydride, thifluoromethane sulfonic acid anhydride, etc.; thionyl chloride, acetone dimethyl acetal, etc. Furthermore, an acid ion-exchange resin can be also used. Examples of the basic compound which can be used include inorganic bases such as sodium hydroxide, potassium hydroxide, sodium carbonate, potassium carbonate, sodium hydrogencarbonate, potassium hydrogencarbonate, silver carbonate, etc.; and alcoholates such as sodium methylate, sodium ethylate, etc. Though the reaction can be carried out without solvents it can be carried out advantageously using the solvent shown in the above-mentioned process (1). Moreover, the reaction proceeds advantageously using a drying agent, for example, anhydrous calcium chloride, anhydrous copper sulfate, anhydrous calcium sulfate and phosphorus pentoxide. The suitable amount of the alcohol of the formula (32) to the compound of the formula (31) is usually in large excess when the reaction is conducted without solvents, and 1 to 5 mols, preferably 1 to 2 mols, of the alcohol of the formula (32) per mol of the compound of the formula (31) is used suitably when the reaction is conducted in the presence of the solvent. The reaction is carried out usually at −20° C. to 200° C., preferably at about 0° C. to 150° C., and completed in about 1 to 20 hours The reduction reaction of the compound of the formula (31) or (33) can be carried out under the conditions similar to those of the reduction reaction which forms the compound of the formula (1h) from the compound of the formula (1g) in the above-mentioned Reaction Scheme-7.

The halogenation reaction of the compound of the formula (34) is carried out under the conditions similar to those of the halogenation reaction of the compounds of the formula (26), (30) or (27) in Reaction Scheme-10.

The carboxylic acid of the formula (31) which is the starting material in the Reaction Scheme-11 and its homocarboxylic acid compound can be produced by the process shown in the following Reaction Scheme-12:

[Reaction Scheme-12]

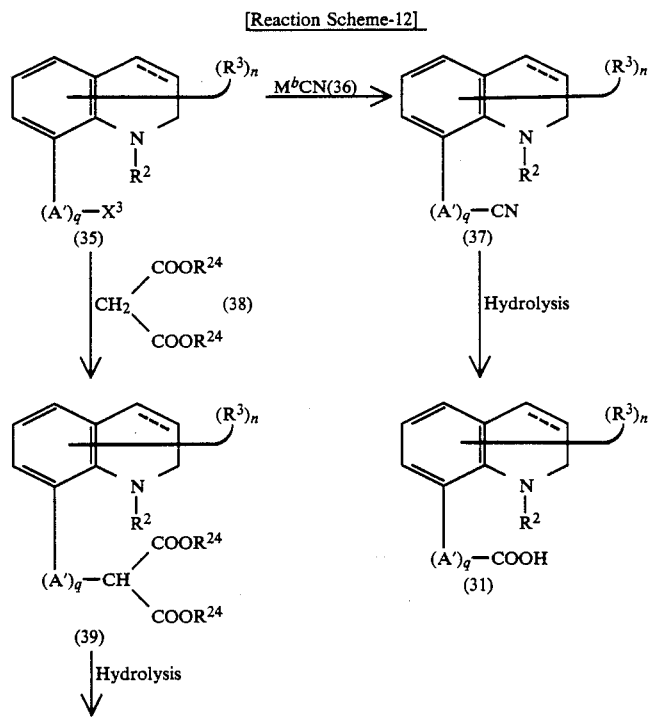

[Reaction Scheme-12]

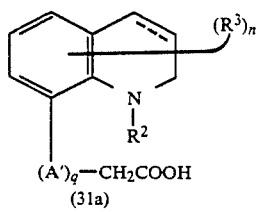

(31a)

wherein $R^2$, $R^3$, n, A', q, $X^3$ and the bond between the 3- and 4-positions of the quinoline skeleton have the same meanings as defined above, $R^{24}$ represents a lower alkyl group, and $M^b$ represents a metal.

The reaction between the compound of the formula (35) and the compound of the formula (36) can be carried out in a suitable solvent. $M^b$CN of the formula (36) includes, for example, cyanides such as potassium cyanide, sodium cyanide, silver cyanide, copper cyanide, calcium cyanide and the like. Example of the solvent which can be used in the reaction include water, alcohols such as methanol, ethanol, isopropanol and the like; and a mixed solvent thereof. The suitable amount of the compound of the formula (36) is at least equimolar, preferably equimolar to 1.5 mols, of the compound of the formula (36) per mol of the compound of the formula (35). The reaction is carried out usually at room temperature to 150° C., preferably at about 50° C. to 120° C., and completed in about 30 minutes to 10 hours.

The hydrolysis reaction of the compound of the formula (37) is carried out in the presence of a hydrolytic catalyst in a suitable solvent or without solvents. Examples of the hydrolytic catalyst include mineral acids such as hydrogen halides [e.g. hydrochloric acid, hydrobromic acid, etc.], sulfuric acid, phosphoric acid, etc.; alkali metal hydroxides such as sodium hydroxide, potassium hydroxide, etc.; alkali metal carbonates or alkali metal hydrogencarbonates such as sodium carbonate, potassium carbonate and sodium hydrogencarbonate, etc. Examples of the solvent which can be used in the above reaction include water, alcohols such as methanol, ethanol, and the like; or a mixed solvent thereof. The reaction is carried out usually at 0° C. to 150° C., preferably at room temperature to 100° C., and completed in about 1 to 24 hours.

The reaction between the compound of the formula (35) and the compound of the formula (38) is carried out in a suitable solvent, in the presence of a basic compound and usually at room temperature to 200° C., preferably at 60° C. to 120° C., and completed in about 1 to 24 hours. Examples of the solvent which can be used include ethers such as dioxane, tetrahydrofuran, ethyleneglycol dimethyl ether, diethyl ether, etc.; aromatic hydrocarbons such as benzene, toluene, xylene, etc.; lower alcohols such as methanol, ethanol, isopropanol, etc.; and polar solvents such as dimethyl formamide, dimethylsulfoxide, etc. Examples of the basic compound which can be used in the above reaction include inorganic bases such as calcium carbonate, sodium carbonate, potassium carbonate, sodium hydrogencarbonate, sodium hydroxide, potassium hydroxide, sodium amide, sodium hydride, potassium hydride, sodium methylate, sodium ethylate and the like; and amines such as triethylamine, tripropylamine, pyridine, quinoline and the like. The reaction proceeds advantageously by the using of alkali metal iodides such as potassium iodide, sodium iodide, etc. The amount of the compound of the formula (38) is usually equimolar to large excess, preferably equimolar to 5 mols and more preferably equimolar to 1.2 mols, of the compound of the formula (38) per mol of the compound of the formula (35).

The hydrolysis reaction of the compound of the formula (39) is carried out under the conditions similar to those of the hydrolysis reaction of the compound of the formula (37) above.

Some compounds of the formula (34) in Reaction Scheme-11 can be produced, for example, by the processes of the following Reaction Schemes-13 to 19.

[Reaction Scheme-13]

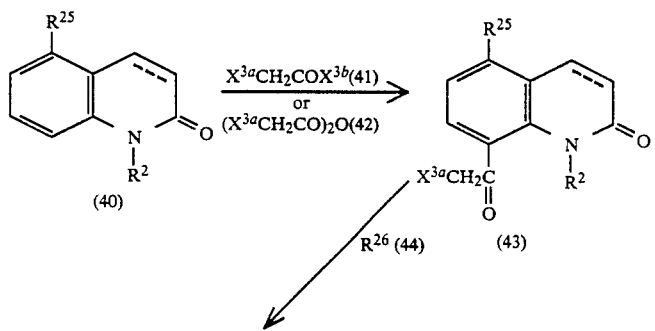

[Reaction Scheme-13]

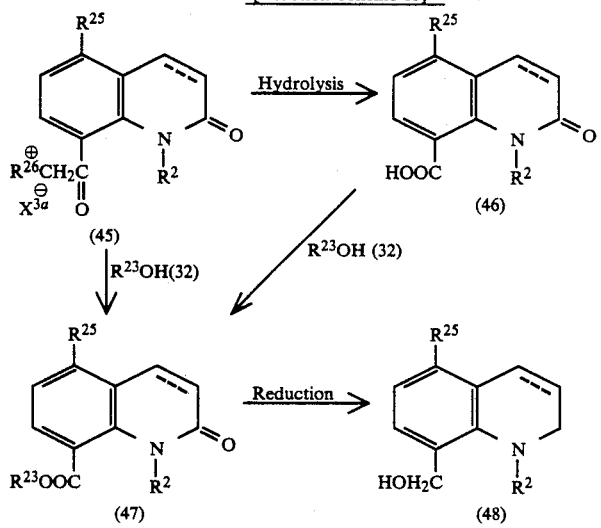

wherein $R^2$, $R^{23}$, $X^{3a}$, $X^{3b}$ and the bond between the 3- and 4-positions of the quinoline skeleton have the same meanings as defined above, $R^{25}$ represents a hydrogen atom, a lower alkoxy group, a lower alkyl group, a halogen atom, a hydroxy group, a lower alkenyloxy group, a hydroxy-substituted lower alkyl group, group of the formula:

(wherein $R^4$ and $R^5$ have the same meanings as defined above) or a phenyl group, and $R^{26}$ represents an aromatic amine.

The reaction between the compound of the formula (40) and the compound of the formula (41) or the compound of the formula (42) is generally called Friedel-Crafts reaction and is usually carried out in a suitable solvent in the presence of a Lewis acid. As for the solvent, the solvent which is used conventionally in this type reaction can be used advantageously, and examples of the solvent include carbon disulfide, nitrobenzene, chlorobenzene, dichloromethane, dichloroethane, trichloroethane, carbon tetrachloride, etc. As for the Lewis acid, conventional Lewis acid, for example, aluminum chloride, zinc chloride, iron chloride, tin chloride, boron tribromide, boron trifluoride, concentrated sulfuric acid, etc. can be used in the reaction The amount of the Lewis acid to be used is not limited and can be varied widely, usually 2 to 6 mols, preferably 3 to 4 mols, of the Lewis acid per mol of the compound of the formula (40) are used. The amount of the compound of the formula (41) or (42) is usually at least equimolar, preferably equimolar to 3 mols, of the compound of the formula (41) or (42) per mol of the compound of the formula (40). The reaction temperature is usually about room temperature to 120° C., preferably 40° C. to 70° C. and the reaction time, which varies depending on the materials, catalyst, reaction temperature, etc., is usually about 30 minutes to 24 hours.

In this reaction, when $R^{25}$ of the compound of the formula (40) is hydrogen atom, a halogen atom or a lower alkyl group, the compound substituted with the side chain $X^{3a}$—$CH_2CO$— at the 6-position of the carbostyryl skeleton also forms simultaneously. The compound, however, can be separated readily The reaction between the compound of the formula (43) and the compound of the formula (44) is carried out in a suitable solvent or without solvents. As for the solvent, any inert solvent which does not affect adversely on the reaction can be used.

Examples of the solvent include halogenated hydrocarbons such as chloroform, methylene chloride, dichloroethane, carbon tetrachloride, etc.; ethers such as diethyl ether, tetrahydrofuran, dioxane, dimethoxyethane, etc.; alcohols such as methanol, ethanol, isopropanol, butanol, etc.; esters such as methyl acetate, ethyl acetate, etc.; aprotic polar solvents such as DMF, DMSO, HMPA, etc.; acetonitrile, etc. Examples of the aromatic amine of the formula (44) include pyridine, quinoline, etc. The amount of the aromatic amine of the formula (44) is at least equimolar, preferably in large excess, of the aromatic amine of the formula (44) per mol of the compound of the formula (43). The reaction temperature is at 50° C. to 200° C., preferably 70° C. to 150° C. and the reaction is completed in about 3 to 10 hours.

The hydrolysis reaction which forms the compound of the formula (46) from the resulting compound of the formula (45) is carried out in water in the presence of an inorganic base such as sodium hydroxide and potassium hydroxide at room temperature to 150° C. in about 1 to 10 hours.

The esterification reaction between the compound of the formula (46) and the compound of the formula (32) is carried out in the presence of a basic compound in a solvent or without solvents. Examples of the solvent which can be used in the reaction include halogenated hydrocarbons such as methylene chloride, chloroform, dichloroethane, etc.; aromatic hydrocarbons such as benzene, toluene, xylene, etc.; ethers such as diethyl ether, tetrahydrofuran, dioxane, dimethoxyethane, etc.; and aprotic polar solvents such as DMF, DMSO, HMPA, etc. Examples of the basic catalyst which can be used include organic bases such as triethylamine, trimethylamine, pyridine, dimethylaniline, N-methylmorpholine, 4-dimethylaminopyridine, DBN, DBU, DABCO and the like; and inorganic bases such as potassium carbonate, sodium carbonate, potassium hydrogencarbonate, sodium hydrogencarbonate and the like. In the above reaction, the suitable amount of the basic compound is at least equimolar, preferably 1 to 1.5 mols, of the basic compound per mol of the compound of the formula (46). The suitable amount of the compound of the formula (32) is usually at least equimolar, preferably in large excess, of the compound of the formula (32) per mol of the compound of the formula (46). The reaction temperature is usually at room temperature to 150° C., preferably at about 50° C. to 100° C., and the reaction generally is completed in 30 minutes to 10 hours.

The reaction between the compound of the formula (45) and the compound of the formula (32) can be carried out in the presence of a basic compound in a solvent or without solvents.

Examples of the solvent which can be used in the reaction include halogenated hydrocarbons such as dichloromethane, chloroform, dichloroethane, etc.; aromatic hydrocarbons such as benzene, toluene, xylene, etc.; ethers such as diethyl ether, tetrahydrofuran, dioxane, dimethoxyethane, etc.; and aprotic polar solvents such as DMF, DMSO, HMPA, etc.

Examples of the basic compound which can be used include organic bases such as triethylamine, trimethylamine, pyridine, N,N-dimethylaniline, N-methylmorpholine, 4-dimethylaminopyridine, DBN, DBU, DABCO and the like; and inorganic bases such as potassium carbonate, sodium carbonate, sodium hydrogencarbonate, potassium hydrogencarbonate and the like.

The suitable amount of the compound of the formula (32) is at least equimolar, preferably in large excess, of the compound of the formula (32) per mol of the compound of the formula (45). The suitable amount of the basic compound is at least equimolar, preferably in equimolar to 1.5 mols, of the basic compound per mol of the compound of the formula (45). The reaction is carried out usually at room temperature to 150° C., preferably at about 50° C. to 100° C., and generally completed in about 30 minutes to 10 hours.

The reduction reaction of the compound of the formula (47) can be carried out under the conditions similar to those of the reduction reaction of the compound of the formula (33) mentioned before. In this reaction, lithium aluminum hydride is preferably used as the reducing agent.

wherein $R^2$, $X^3$, M and the bond between the 3- and 4-positions of the quinoline skeleton have the same meanings as defined above, and $R^{27}$ represents a lower alkoxy group.

The halogenation reaction of the compound of the formula (49), except for the use of 2,4,4,6-tetrabromocyclohexa-2,5-dienone as the halogenating agent, can be carried out under the conditions similar to those of the halogenation reaction of the compound of the formula (21) mentioned before.

The reaction between the compound of the formula (50) and the compound of the formula (52) can be carried out in a suitable solvent in the presence or absence of a basic compound.

Examples of the solvent and the basic compound which can be used include the solvent and the basic compound used in the reaction between the compound of the formula (2) and the compound of the formula (3) in Reaction Scheme-1.

The reaction is carried out usually at 0° C. to 150° C., preferably at about 0° C. to 100° C., and completed in about 1 to 24 hours. The suitable amount of the compound of the formula (52) is usually at least equimolar, preferably equimolar to 1.5 mols, of the compound of the formula (52) per mol of the compound of the formula (50). The reaction can proceed advantageously with the addition of copper halides such as copper iodide, etc.; copper powder, etc.

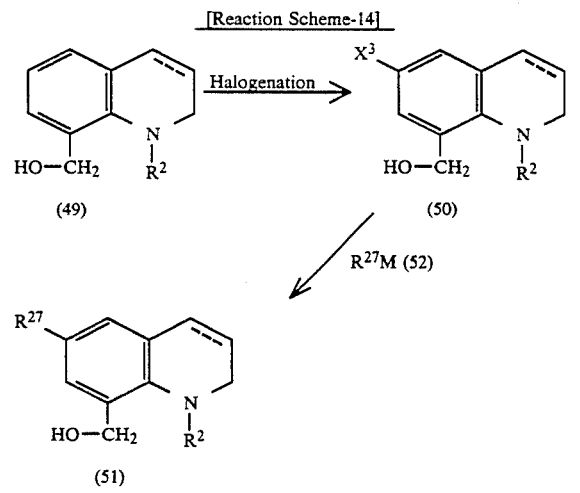

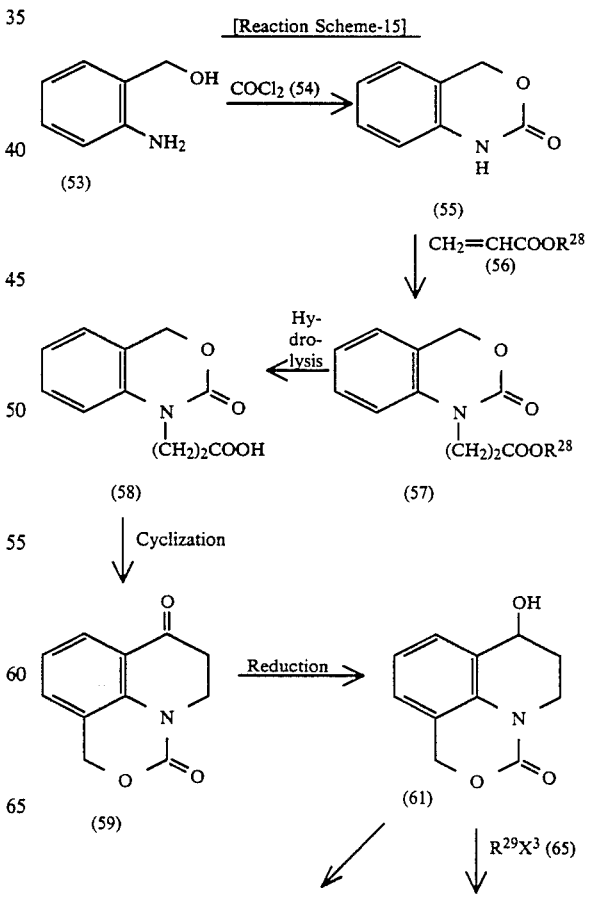

-continued
[Reaction Scheme-15]

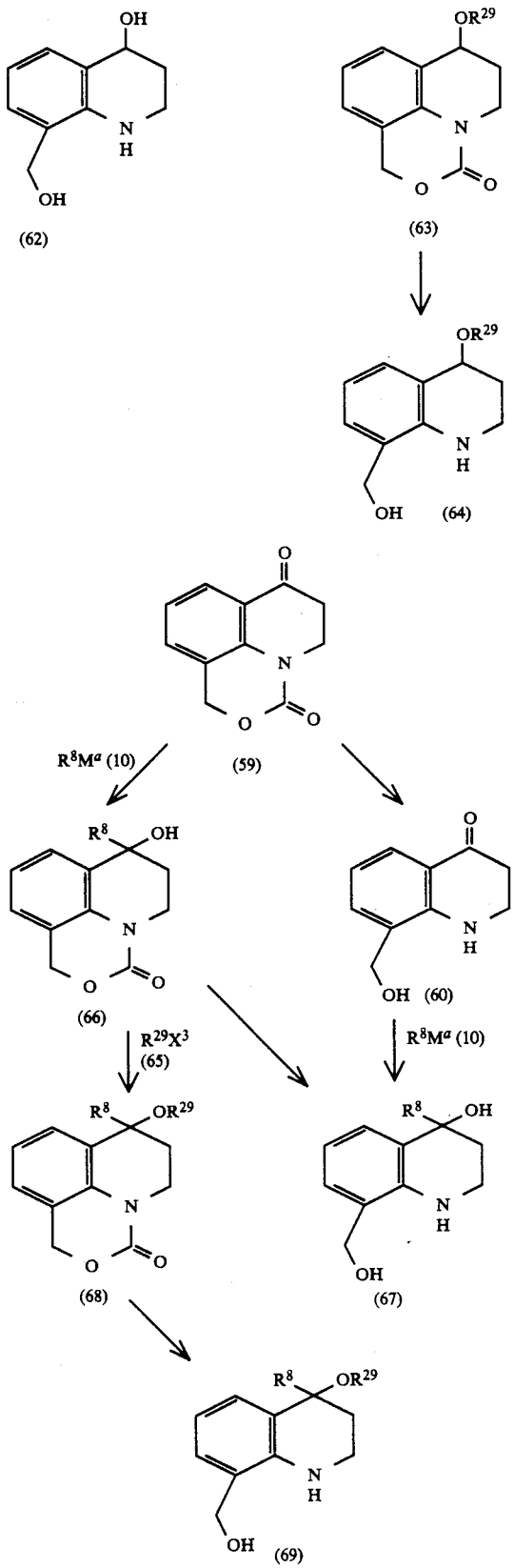

wherein $R^8$, $X^3$ and $M^a$ have the same meanings as defined above, $R^{28}$ represents a lower alkyl group, and $R^{29}$ represents a lower alkyl group, a lower alkenyl group or a lower alkoxy lower alkyl group.

The reaction between the compound of the formula (53) and phosgene (54) is carried out in a suitable solvent or without solvents in the presence of a basic compound.

The reaction is carried out usually at room temperature to 150° C., preferably at room temperature to 100° C., and completed in about 0.5 to 10 hours.

Examples of the solvent which can be used in the reaction include lower alcohols such as methanol, ethanol, isopropanol, etc.; ethers such as diethyl ether, tetrahydrofuran, dioxane, ethyleneglycol monomethyl ether, diethyleneglycol dimethyl ether, etc.; aromatic hydrocarbons such as benzene, toluene, xylene, etc.; ketones such as acetone, methylethylketone, etc.; and aprotic polar solvents such as DMF, DMSO, HMPA, etc.

Examples of the basic compound which can be used include inorganic bases such as sodium hydroxide, potassium hydroxide, sodium carbonate, potassium carbonate, sodium hydrogencarbonate, potassium hydrogencarbonate, silver carbonate, etc.; alkali metals such as sodium, potassium, etc.; sodium amide; sodium hydride; alkali metal alcoholates such as sodium methylate, sodium ethylate, potassium ethylate, etc.; and organic bases such as triethylamine, tripropylamine, pyridine, quinoline, N,N-dimethylaniline, N-methylmorpholine, etc.

The suitable amount of phosgene (54) is at least equimolar, preferably equimolar to 5 mols, of phosgene (54) per mol of the compound of the formula (53).

The reaction between the compound of the formula (55) and the compound of the formula (56) is carried out in a suitable solvent in the presence of a basic compound. The reaction is conducted usually at room temperature to 150° C., preferably room temperature to 100° C., and completed in about 1 to 10 hours. Examples of the basic compound and solvent which can be used in the reaction include the basic compound and solvent illustrated in the above-mentioned reaction between the compound of the formula (53) and phosgene (54).

The reaction that hydrolyzes the compound of the formula (57) and converts it to the compound of the formula (58) can be carried out under the conditions similar to those of the above-mentioned hydrolysis reaction that forms the compound of the formula (24) from the compound of the formula (23) in Reaction Scheme-10.

The cyclization reaction of the compound of the formula (58) can be carried out in accordance with various conventional cyclization methods, for example, a cyclization process by heating; a cyclization process using an acid such as phosphorus oxychloride, phosphorus pentachloride, phosphorus trichloride, thionyl chloride, concentrated sulfuric acid, polyphosphoric acid and the like; etc. When the heating cyclization process is employed, hydrocarbons and ethers having high-boiling point such as tetralin, diphenyl ether, diethyleneglycol dimethyl ether are used, and the heating conditions of 100° C. to 250° C., preferably 150° C. to 200° C., can be usually applied . When the cyclization process using the acid is employed, the amount of the acid is usually equimolar to large excess, preferably 3 to 20 mols, of the acid per mol of the compound of the formula (58), and the reaction is carried out usually at room temperature to 150° C. for about 0.1 to 6 hours. In the cyclization process using the acid, the reaction is carried out without solvents or in a suitable solvent, for example, ethers such as diethyl ether, dioxane, tetrahydrofuran, monoglyme, diglyme, etc.; aliphatic hydrocarbons such as n-hexane, heptane, ligroin, etc.; halogenated hydrocarbons such as chloroform, methylene chloride, carbon tetrachloride, etc.; aprotic polar solvents such as DMF, DMSO, HMPA, etc.; and acid anhydrides such as acetic anhydride, etc.

The reduction reaction which converts the compound of the formula (59) to the compound of the formula (61) can be carried out under the conditions similar to those of the above-mentioned reduction reaction that forms the compound of the formula (1h) from the compound of the formula (1g) in Reaction Scheme-7.

The reaction between the compound of the formula (61) or (66) and the compound of the formula (65) can be carried out in a suitable solvent in the presence of a basic compound.

Examples of the solvent which can be used in the reaction include the ethers, alcohols, aromatic hydrocarbons, aliphatic hydrocarbons, amines, halogenated hydrocarbons, aprotic polar solvents or a mixed solvent thereof, etc. illustrated in the reaction between the carbonyl group of the quinoline skeleton in the compound of the formula (1i) and the lower alkyleneglycols in Reaction Scheme-8.

Examples of the basic compound which can be used include inorganic bases such as sodium, potassium, magnesium, sodium hydride, sodium amide, sodium hydroxide, potassium hydroxide, sodium carbonate, potassium carbonate, sodium hydrogencarbonate, etc.; metal alcoholates such as sodium methylate, sodium ethylate, etc.; and organic bases such as pyridine, piperidine, quinoline, triethylamine, N,N-dimethylaniline, etc. The reaction temperature is usually −30° C. to 120° C., preferably about 0° C. to 100° C.,and the reaction generally is completed in about 0.1 to 15 hours. The suitable amount of the compound of the formula (65) is usually at least equimolar, preferably equimolar to 3 mols, of the compound of the formula (65) per mol of the compounds of the formula (61) or (66).

The reaction which converts the compounds of the formulas (59), (61), (66), (68) and (63) to the compounds of the formulas (60), (62), (67), (69) and (64) respectively can be carried out under the conditions similar to those of the hydrolysis reaction that forms the compound of the formula (24) from the compound of the formula (23) in Reaction Scheme-10.

The reaction between the compounds of the formula (59) or (60) and the compound of the formula (10) can be carried out under the conditions similar to those of the reaction between the compound of the formula (1i) and the compound of the formula (10) in Reaction Scheme-8.

The compounds of the formulas (60), (62), (64), (67) and (69) can be led to compounds, where the hydrogen atoms at the 1-position of the quinoline skeleton of the compound of the formulas (60), (62), (64), (67) and (69) are substituted with $R^{2'}$ ($R^{2'}$ has the same meaning as defined above) respectively, by allowing them to react with the compound of the formula (9) under the conditions similar to those of the reaction between the compound of the formula (25) and the compound of the formula (9) in Reaction Scheme-10.

The compounds of the formulas (59) and (60) can be converted to the compounds having a lower alkylenedioxy group at the carbonyl group of the compounds of the formulas (59) and (60) respectively by subjecting them to the reaction conducted under the substantially same conditions as those of the above-mentioned reaction that converts the carbonyl group of the compound of the formula (1i) to the lower alkylenedioxy group in Reaction Scheme-8.

The lower alkylenedioxy group-substituted compound in the above reaction can be converted to a compound substituted with a carbonyl group by subjecting the compound to a hydrolysis reaction under the same conditions as in the above-mentioned hydrolysis reaction that converts the lower alkylenedioxy group of the compound of the formula (1i) to the carbonyl group in Reaction Scheme-8.

[Reaction Scheme-16]

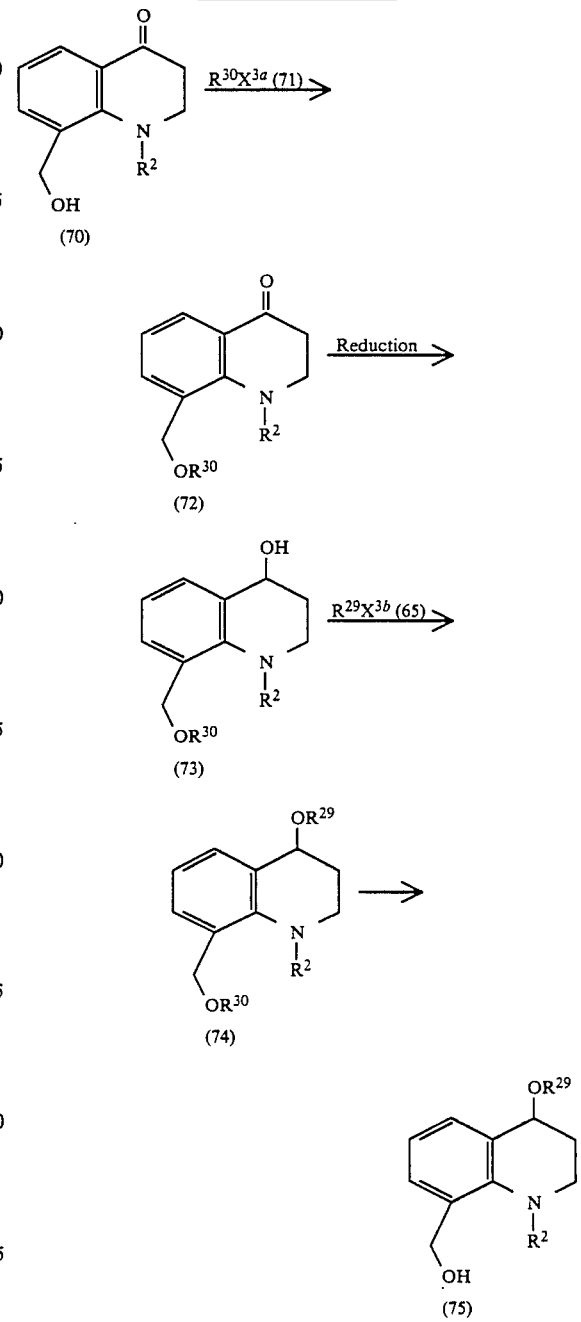

wherein $R^{30}$ represents a silyl group having 1 to 3 of lower alkyl groups, and $R^2$, $R^{29}$, $X^{3a}$ and $X^{3b}$ have the same meanings as defined above.

The reaction between the compound of the formula (70) and the compound of the formula (71) can be carried out in the presence of a basic compound in a suitable solvent.

As for the basic compound, there can be used, for example, inorganic bases such as sodium hydride, potassium hydride, sodium, potassium, sodium amide, potassium amide, sodium hydroxide, potassium hydroxide, sodium carbonate, potassium carbonate, sodium hydrogencarbonate, potassium hydrogencarbonate, etc.; alkyl lithiums such as n-butyl lithium, etc.; and organic bases such as triethylamine, pyridine, N,N-dimethylaminopyridine, imidazole, N-methylmorpholine, DBN, DBU, DABCO, etc. Examples of the solvent which can be used include all of the solvents shown in the above-mentioned reaction between the compound of the formula (25) and the compound of the formula (9) in Reaction Scheme-10.

The reaction is conducted usually at 0° C. to 100° C., preferably at 0° C. to 80° C., and completed in about 10 minutes to 20 hours.

The suitable amount of the compound of the formula (71) is at least equimolar, preferably equimolar to 2 mols, of the compound of the formula (71) per mol of the compound of the formula (70).

The reduction reaction of the compound of the formula (72) can be carried out under the conditions similar to those of the reduction reaction of the compound of the formula (1g) in Reaction Scheme-7.

The reaction between the compound of the formula (73) and the compound of the formula (65) can be carried out under the conditions similar to those of the reaction between the compound of the formula (61) and the compound of the formula (65) in Reaction Scheme-15.

The reaction which leads the compound of the formula (74) to the compound of the formula (75) can be carried out under the conditions similar to those of the above-mentioned desilylation reaction which is conducted when $R^2$ is a lower alkynyl group possessing a tri-loweralkylsilyl group in the compounds of the formulas (1a) to (1d).

[Reaction Scheme-17]

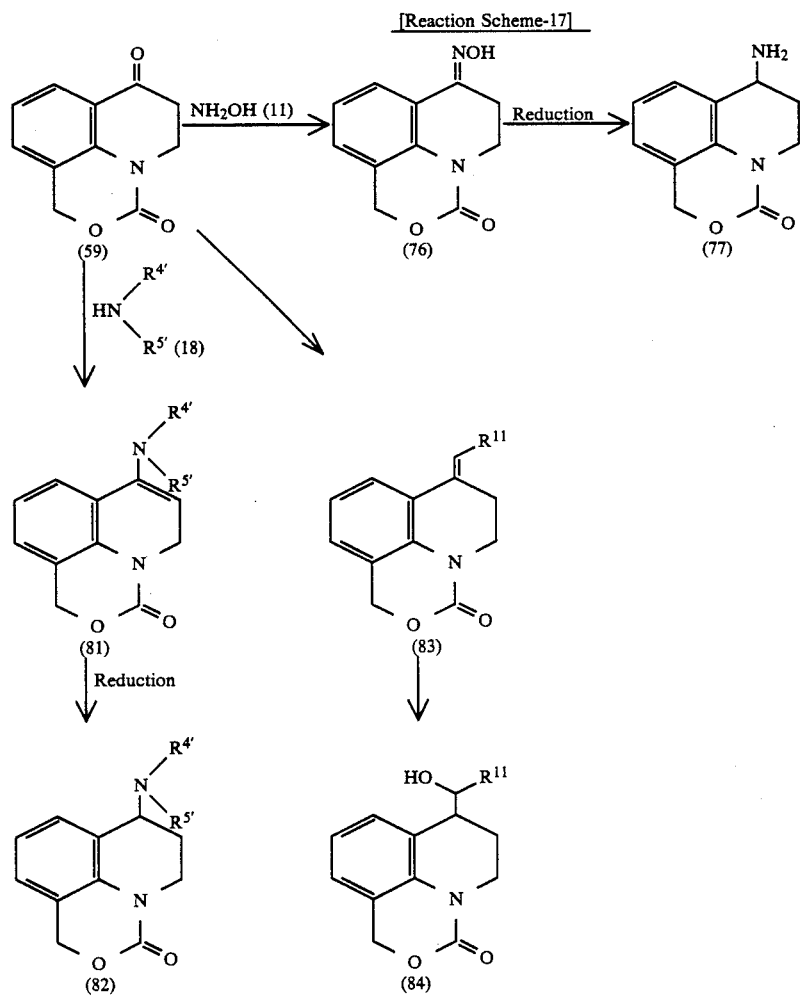

[Reaction Scheme-17]
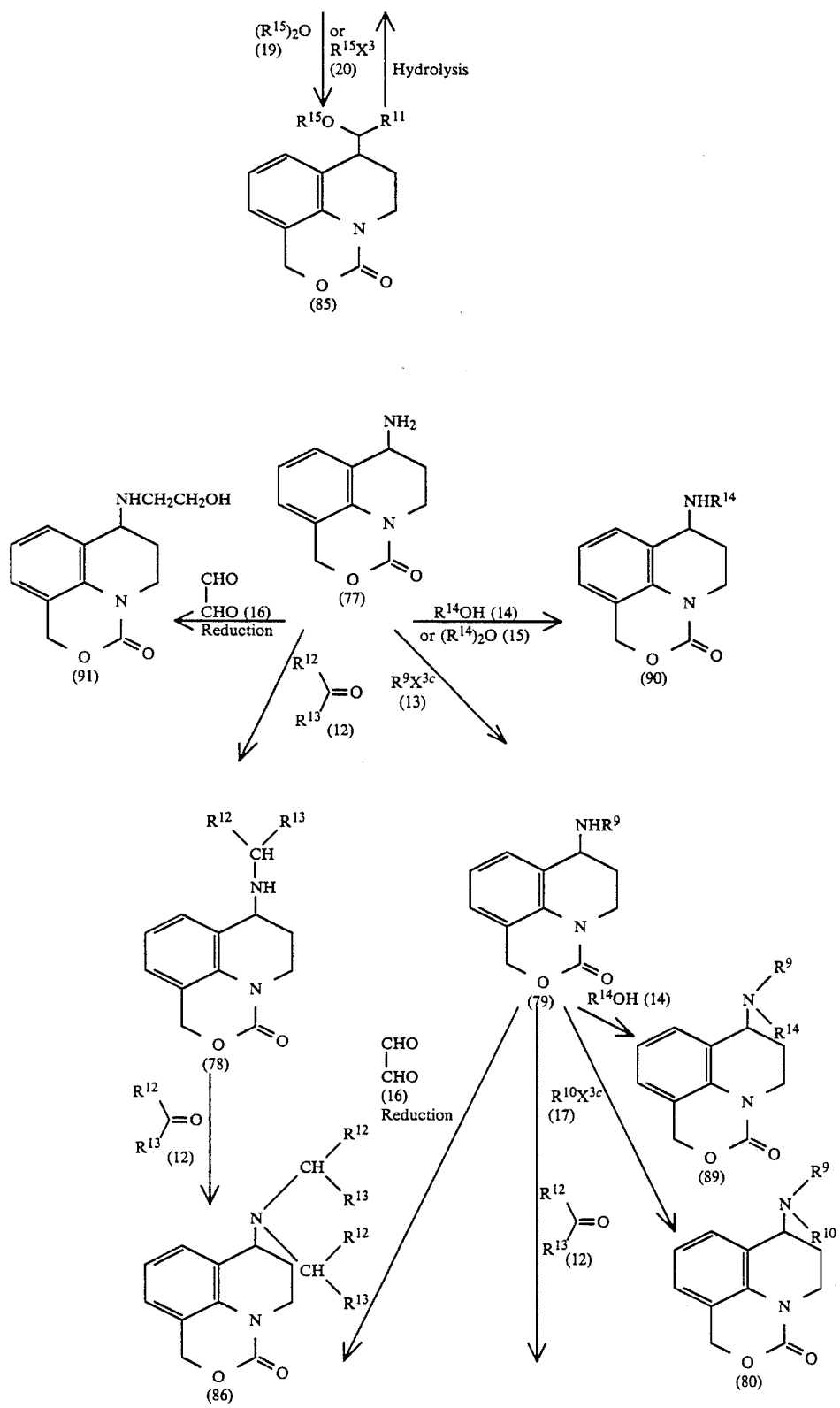

-continued
[Reaction Scheme-17]

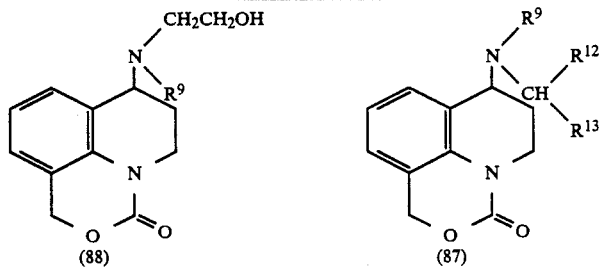

wherein $R^{4'}$, $R^{5'}$, $R^9$, $R^{10}$, $R^{11}$, $R^{12}$, $R^{13}$, $R^{14}$, $R^{15}$ and $X^{3c}$ have the same meanings as defined above.

The reaction between the compound of the formula (59) and hydroxylamine (11) can be carried out under the conditions similar to those of the reaction between the compound of the formula (1g) and hydroxylamine (11) in Reaction Scheme-9.

The reduction reaction of the compound of the formula (76) can be carried out under the conditions similar to those of the reduction reaction of the compound of the formula (1k) in Reaction Scheme-9.

The reaction between the compound of the formula (59) and the compound of the formula (18) can be carried out under the conditions similar to those of the reaction between the compound of the formula (1g) and the compound of the formula (18) in Reaction Scheme-9. The compound of the formula (81) obtained in this reaction is subjected to the next reduction reaction without isolation.

The reduction reaction of the compound of the formula (81) can be carried out under the conditions similar to those of the reduction reaction of the compound of the formula (1m) in Reaction Scheme 9.

The reaction between the compound of the formula (77), (78) or (79) and the compound of the formula (12) can be carried out under the conditions similar to those of the reaction between the compound of the formula (11) or (1r) and the compound of the formula (12) in Reaction Scheme-9.

The reaction between the compound of the formula (77) and the compound of the formula (13), and the reaction between the compound of the formula (79) and the compound of the formula (17) can be carried out under the conditions similar to those of the reaction between the compound of the formula (11) and the compound of the formula (13), and the reaction between the compound of the formula (1o) and the compound of the formula (17) in Reaction Scheme-9. In the reaction between the compound of the formula (77) and the compound of the formula (13), 2 mols of the compound of the formula (13) may react with the compound of the formula (77) to form the compound having group: —N($R^9$)$_2$. The resulting compound, however, can be separated readily.

The reaction that leads the compound of the formula (59) to the compound of the formula (83) can be carried out under the conditions similar to those of the Witting Reaction that leads the compound of the formula (1g) to the compound of the formula (1g) in Reaction Scheme-9.

The reaction between the compound of the formula (77) and the compound of the formula (15) can be carried out under the conditions similar to those of the reaction between the compound of the formula (11) and the compound of the formula (13) or the reaction between the compound of the formula (1o) and the compound of the formula (17) in Reaction Scheme-9.

The reaction between the compound of the formula (77) or (79) and the compound of the formula (14) can be carried out under the conditions similar to those of the reaction between the compound of the formula (11) or (1o) and the compound of the formula (14) in Reaction Scheme-9.

The reaction between the compound of the formula (77) or (79) and glyoxal (16) and the subsequent reduction reaction can be carried out under the conditions similar to those of the reaction between the compound of the formula (11) or (1o) and glyoxal (16) and the subsequent reduction reaction in Reaction Scheme-9.

The reaction which leads the compound of the formula (83) to the compound of the formula (84) can be carried out under the conditions similar to those of the reaction that leads the compound of the formula (1q) to the compound of the formula (1y) in Reaction Scheme-9.

The reaction between the compound of the formula (84) and the compound of the formula (19) can be carried out under the conditions similar to those of the reaction between the compound of the formula (77) and the compound of the formula (15) mentioned before.

The reaction between the compound of the formula (84) and the compound of the formula (20) can be carried out under the conditions similar to those of the reaction between the compound of the formula (77) and the compound of the formula (13) mentioned before.

The hydrolysis reaction of the compound of the formula (85) can be carried out under the conditions similar to those of the hydrolysis reaction of the compound of the formula (1z) in Reaction Scheme-9.

The compounds of the formulas (76), (77), (81), (82), (83), (78), (86), (79), (80), (89), (87), (88) and (84) can be led to respectively corresponding compounds having the following partial structure:

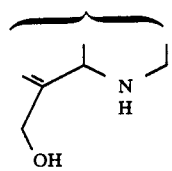

by subjecting them to the reaction which is carried out under the conditions similar to those of the reaction which leads the compound of the formula (59) to the compound of the formula (60) in Reaction Scheme-15.

The carbonyl group of the compounds of the formulas (89) and (90) can be led to —CH$_2$—group by subjecting the compounds of the formulas (89) and (90) to the reduction reaction carried out under the same manner as that of the reduction reaction of the compound of the formulas (1t) and (1v) in Reaction Scheme-9.

When one of $R^{4'}$ or $R^{5'}$ is a hydrogen atom and the other is group $R^{4a}$ (wherein $R^{4a}$ has the same meaning as defined above) in the formula (18), the compound of the following formula (81a):

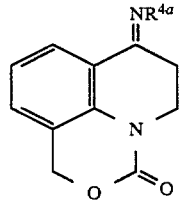
(81a)

(wherein $R^{4a}$ has the same meaning as defined above) can also be obtained by the reaction between the compound of the formula (59) and the compound of the formula (18).

The above mentioned compound can be let to the compound of the following formula (82a):

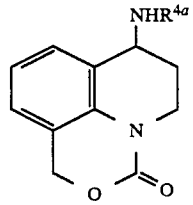
(82a)

(wherein $R^{4a}$ has the same meaning as defined above) in the same way as the reduction reaction of the compound of the formula (81).

[Reaction Scheme-18]

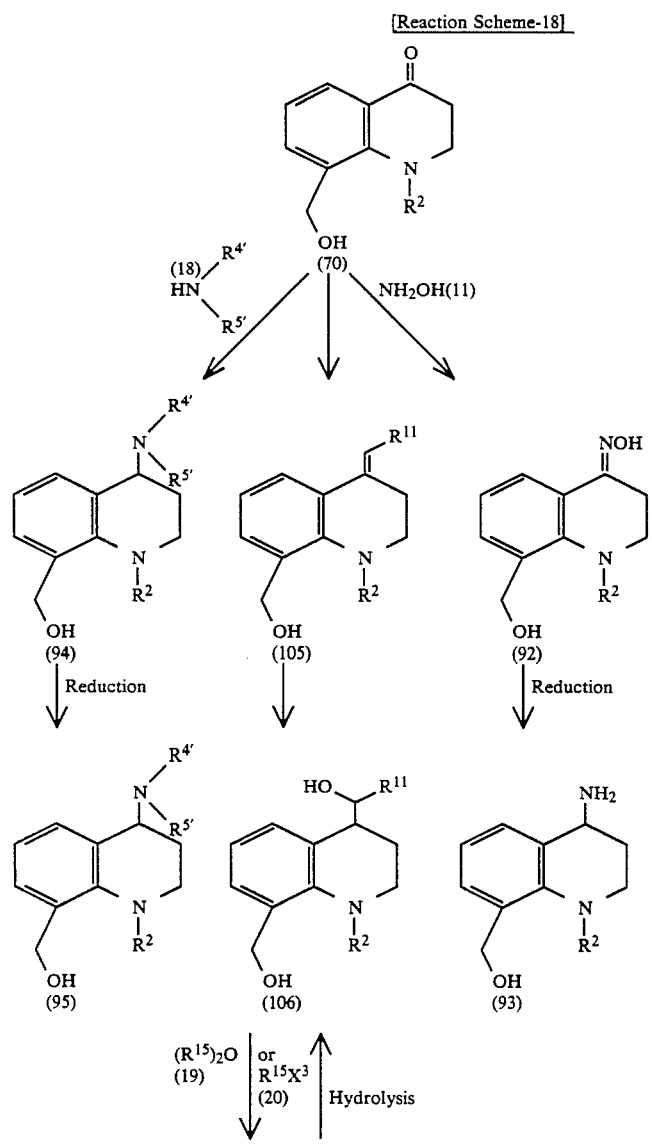

4,963,566
-continued
[Reaction Scheme-18]
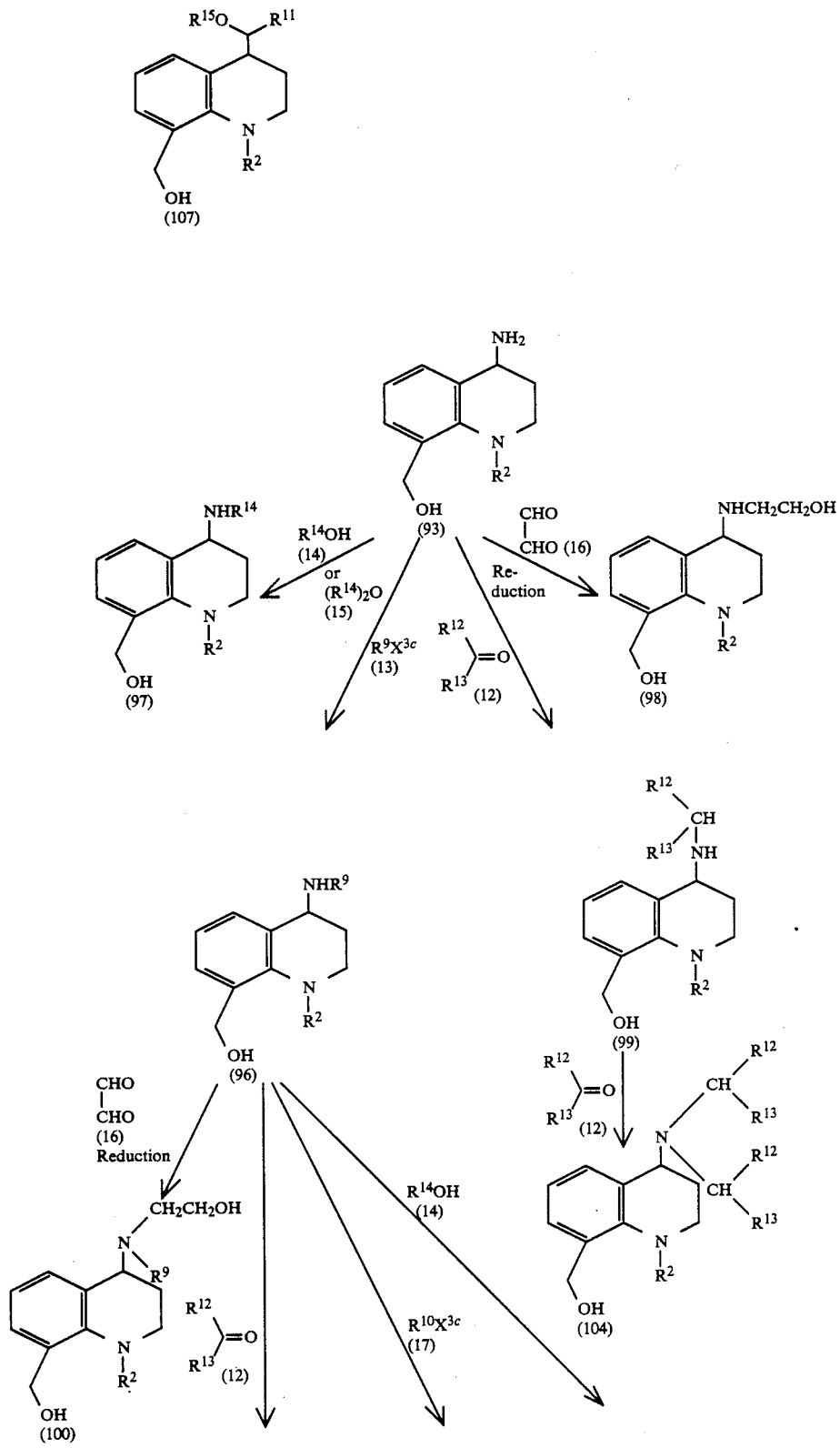

-continued
[Reaction Scheme-18]

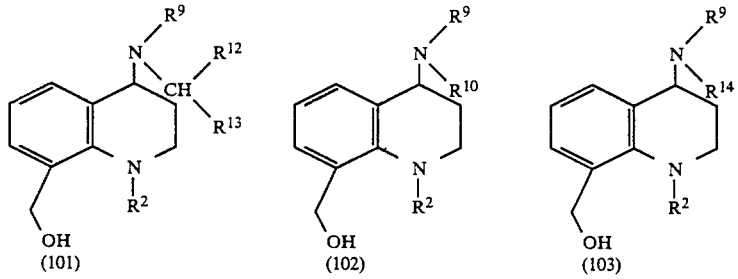

wherein $R^2$, $R^{4'}$, $R^5$, $R^9$, $R^{10}$, $R^{11}$, $R^{12}$, $R^{13}$, $R^{14}$, $R^{15}$ and $X^{3c}$ have the same meanings as defined above.

The reaction between the compound of the formula (70) and the compound of the formula (11) can be carried out under the conditions similar to those of the reaction between the compound of the formula (1g) and the compound of the formula (11) in Reaction Scheme-9.

The reduction reaction which leads the compound of the formula (92) to the compound of the formula (93) can be carried out under the conditions similar to those of the reduction reaction which leads the compound of the formula (1k) to the compound of the formula (1l) in Reaction Scheme-9.

The reaction between the compound of the formula (70) and the compound of the formula (18) can be carried out under the conditions similar to those of the reaction between the compound of the formula (1g) and the compound of the formula (18) in Reaction Scheme-9.

The reduction reaction which leads the compound of the formula (94) to the compound of the formula (95) can be carried out under the conditions similar to those of reduction reaction which leads the compound of the formula (1m) to the compound of the formula (1n) in Reaction Scheme-9.

The reaction between the compounds of the formula (93), (99) or (96) and the compound of the formula (12) can be carried out under the conditions similar to those of the reaction between the compounds of the formula (11) or (1r) and the compound of the formula (12) in Reaction Scheme-9.

The reaction between the compounds of the formula (93) or (96) and the compound of the formula (16) and the subsequent reduction reaction can be carried out under the conditions similar to those of the reaction between the compounds of the formula (11) or (1o) and the compound of the formula (16) and the subsequent reduction reaction in Reaction Scheme-9.

The reaction between the compounds of the formula (93) or (96) and the compound of the formula (14) can be carried out under the conditions similar to those of the reaction between the compounds of the formula (11) or (1o) and the compound of the formula (14) in Reaction Scheme-9.

The reaction between the compounds of the formula (93) or (96) and the compound of the formula (15) can be carried out under the conditions similar to those of the reaction between the compound of the formula (11) and the compound of the formula (13) or the reaction between the compound of the formula (1o) and the compound of the formula (17) in Reaction Scheme-9.

The reaction between the compound of the formula (93) and the compound of the formula (13), and the reaction between the compound of the formula (96) and the compound of the formula (17) can be carried out under the conditions similar to those under which the reaction between the compound of the formula (11) and the compound of the formula (13), and the reaction between the compound of the formula (1o) and the compound of the formula (17) in Reaction Scheme-9 are carried out.

In the above reaction, when $R^2$ of the compounds of the formulas (93) and (96) are a hydrogen atom, the reaction between the 1-position of the hydroquinoline ring and the compound of the formula (13) may occur. The resulting compound, however, can be separated readily. In the reaction between the compound of the formula (93) and the compound of the formula (13), 2 mols of the compound of the formula (13) may react with the compound of the formula (93) to form the compound having group: —N($R^9$)$_2$. However, the resulting compound can be separated readily.

The reaction which leads the compound of the formula (70) to the compound of the formula (105) can be carried out under the conditions similar to those of the reaction which leads the compound of the formula (1g) to the compound of the formula (1q) in Reaction Scheme-9.

The reaction which leads the compound of the formula (105) to the compound of the formula (106) can be carried out under the conditions similar to those of the reaction which leads the compound of the formula (1q) to the compound of the formula (1y) in Reaction Scheme-9.

The reaction between the compound of the formula (106) and the compound of the formula (19) or (20) can be carried out under the conditions similar to those of the reaction between the compound of the formula (84) and the compound of the formula (19) or (20) in Reaction Scheme-17.

The hydrolysis reaction of the compound of the formula (107) can be carried out under the conditions similar to those of the hydrolysis reaction of the compound of the formula (1z) in Reaction Scheme-9.

The compounds of the formulas (70), (92), (93), (99), (96), (94), (105), (106) and (107), if necessary, may be allowed to react respectively with the compound of the formula (71) under the conditions similar to those of the reaction between the compound of the formula (70) and the compound of the formula (71) in Reaction Scheme-16 to convert the 8-position of the hydroquinoline ring thereof to —CH$_2$OR$^{30}$ (R$^{30}$ has the same meaning as defined above), followed by subjecting them respectively to the reactions shown in Reaction Scheme-18, and to the reaction which carried out under the conditions similar to those of the reaction which leads the compound of the formula (74) to the compound of the formula (75) to convert the 8-position of the hydroquinoline ring thereof to —CH$_2$OH group.

In the compound of the formula (94), when one of R$^{4'}$ or R$^{5'}$ is a hydrogen atom and the other is group: R$^{4a}$ (R$^{4a}$ has the same meaning as defined above), the compound of the following formula:

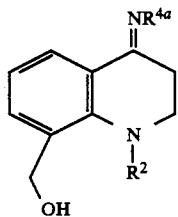

(94a)

(wherein R$^2$ and R$^{4a}$ have the same meanings as defined above) can also be obtained by the reaction between the compound of the formula (70) and the compound of the formula (18).

The above-mentioned compound can be led to the compound of the following formula:

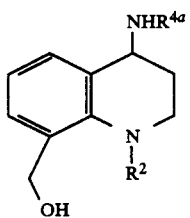

(95a)

(wherein R$^2$ and R$^{4a}$ have the same meanings as defined above), in the same manner as that of reduction reaction which leads the compound of the formula (94) to the compound of the formula (95).

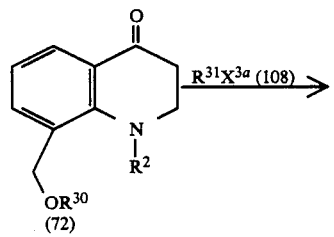

(72)

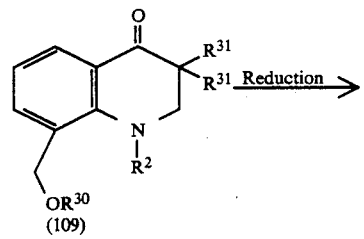

(109)

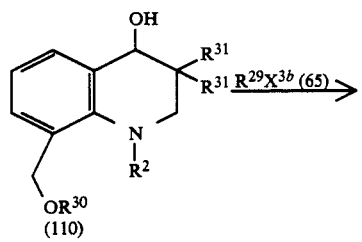

(110)

-continued

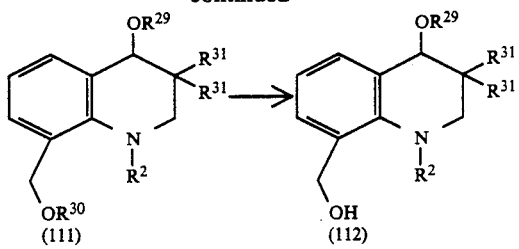

(111) (112)

wherein R$^{31}$ represents a lower alkyl group which may have 1 to 3 halogen atom, a phenyl group, a hydroxy-substituted lower alkyl group, a lower alkanoyloxy lower alkyl group, and R$^2$, R$^{29}$, R$^{30}$, X$^{3a}$ and X$^{3b}$ have the same meanings as defined above.

The reaction between the compound of the formula (72) and the compound of the formula (108) can be carried out in a suitable solvent in the presence of a basic compound. Examples of the solvent and basic compound which can be used include all of the solvents and basic compounds used in the reaction between the compound of the formula (70) and the compound of the formula (71) in Reaction Scheme-16.

The suitable amount of the compound of the formula (108) is at least equimolar, preferably equimolar to 2 mols, of the compound of the formula (108) per mol of the compound of the formula (72).

The reduction reaction of the compound of the formula (109) can be carried out under the conditions similar to those of the reduction reaction of the compound of the formula (1g) in Reaction Scheme-7.

The reaction between the compound of the formula (110) and the compound of the formula (65) can be carried out under the conditions similar to those of the reaction between the compound of the formula (73) and the compound of the formula (65) in the Reaction Scheme-16.

The reaction which leads the compound of the formula (111) to the compound of the formula (112) can be carried out under the conditions similar to those of the reaction which leads the compound of the formula (74) to the compound of the formula (75) in Reaction Scheme-16.

In the compound of the formula (1) and the starting compounds shown in Reaction Schemes 10 to 12, when the group R$^3$ is a lower alkoxycarbonyl group, the group R$^3$ can be led to a hydroxymethyl group by subjecting the compounds having the group R$^3$ to the reduction reaction which can be carried out under the conditions similar to those of the reduction reaction which forms the compound of the formula (1h) from the compound of the formula (1g) in Reaction Scheme-7. When the group R$^3$ is a lower alkoxycarbonyl group, the group R$^3$ can also be led to a carboxy group by subjecting the compounds having the group R$^3$ to the hydrolysis reaction. The hydrolysis reaction can be carried out under the conditions similar to those of the hydrolysis reaction of the compound of the formula (1z).

Furthermore, when the group R$^3$ is a carboxy group, the group R$^3$ can be led to a lower alkoxycarbonyl group by subjecting the compound having the group R$^3$ to conventional esterification reaction. The esterification reaction can be carried out under the conditions similar to those of the reaction between the compound of the formula (31) and the compound of the formula (32) in Reaction Scheme-11.

When the group $R^3$ is a carboxy group, the group $R^3$ can be led to the amido group represented by the following formula:

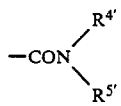

(wherein $R^{4'}$ and $R^{5'}$ have the same meanings as defined above) by subjecting the compound having the group $R^3$ to the reaction with an amine represented by the following formula:

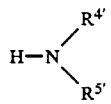

(wherein $R^{4'}$ and $R^{5'}$ have the same meanings as defined above). This reaction can be carried out in the same manner as that of the reaction which obtains the compound of the formula (1t) from the compound of the formula (1l) in Reaction Scheme-9.

When the group $R^3$ denotes the group of the formula:

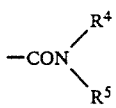

(wherein $R^4$ and $R^5$ have the same meanings as defined above), the group $R^3$ can be led to the group of the formula:

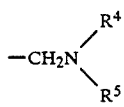

(wherein $R^4$ and $R^5$ have the same meanings as defined above) by subjecting the compounds having the group $R^3$ to the reduction reaction carried out in the same manner as that of the reduction reaction of the compounds of the formulas (1t) and (1v) in Reaction Scheme-9. In the above reaction, when the groups $R^4$ and $R^5$ denote a cycloalkylcarbonyl group or a lower alkanoyl group, they may be reduced simultaneously to form the cycloalkyl lower alkyl group or the lower alkyl group.

In Reaction Schemes 10 to 14, 16, 18 and 19, when the group $R^2$ or $R^{2'}$ of each starting compound is a lower alkynyl group possessing a tri-lower alkylsilyl group, the group $R^2$ or $R^{2'}$ can be led to the lower alkynyl group by subjecting the compounds having the group $R^2$ or $R^{2'}$ to the desilylation reaction under the conditions similar to those of the desilylation reaction of the compounds of the formulas (1a) to (1d).

Among the compounds represented by the formula (1) according to the present invention, compounds having acidic groups can be easily converted to salts by reacting them with a pharmaceutically acceptable basic compound. The basic compound is exemplified by metal hydroxides such as sodium hydroxide, potassium hydroxide, lithium hydroxide, calcium hydroxide, etc., alkali metal carbonates or alkali metal hydrogen carbonates such as sodium carbonate, sodium hydrogen carbonate, and alkali metal alcoholates such as sodium methylate, potassium ethylate, etc. While among the compounds represented by the formula (1), compounds having basic groups can be easily converted to salts by permitting a pharmaceutically acceptable acid to act thereon. The acid is exemplified by inorganic acids such as sulfuric acid nitric acid, hydrochloric acid, hydrobromic acid, etc., and organic acids such as acetic acid, p-toluenesulfonic acid, ethanesulfonic acid, oxalic acid, maleic acid, succinic acid, benzoic acid, etc.

The compound of the invention naturally includes stereoisomers and optical isomers.

The thus-produced compound of this invention can be isolated and purified from the reaction system without difficulty by conventional means of separation. Employable as the conventional means of separation are, for instance, distillation, recrystallization, column chromatography, preparative thin layer chromatography and solvent extraction.

The compounds of this invention are useful as anti-ulcer agents and are used usually in the form of ordinary pharmaceutical preparations. Commonly used diluents or excipients such as fillers, extenders, binders, wetting agents, disintegrants, surfactants and lubricants are employed in the formulation of the preparations. Various dosage forms of the therapeutic agents can be selected according to the purpose of the therapy. Typical dosage forms which can be used are tablets, pills, powders, liquid preparations, suspensions, emulsions, granules, capsules, suppositories, and injectable preparations (solutions, suspensions, etc.).

In molding a pharmaceutical composition into a tablet form, a wide range of carriers known in the art can be used. Examples of suitable carriers include excipients such as lactose, white sugar, sodium chloride, glucose, urea, starch, calcium carbonate, kaolin, crystalline cellulose and silicic acid, binders such as water, ethanol, propanol, simple syrup, glucose solution, starch solution, gelatin solution, carboxymethyl cellulose, shellac, methyl cellulose, potassium phosphate and polyvinyl pyrrolidone, disintetrants such as dried starch, sodium alginate, agar powder, laminaria powder, sodium hydrogencarbonate, calcium carbonate, polyoxyethylenesorbitan fatty acid esters, sodium laurylsulfate, stearic acid monoglyceride, starch, and lactose, disintegration inhibitors such as white sugar, stearin, cacao butter and hydrogenated oils, absorption promoters such as quaternary ammonium bases and sodium laurylsulfate, humectants such as glycerol and starch, adsorbents such as starch, lactose, kaolin, bentonite and colloidal silicic acid, and lubricants such as purified talc, stearic acid salts, boric acid powder, polyethylene glycol.

The tablets, if desired, can be coated, and made into sugar-coated tablets, gelatin-coated tablets, enteric-coated tablets, film-coated tablets, or tablets comprising two or more layers.

In molding the pharmaceutical composition into pills, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, gelatin, and ethanol, and disintegrants such as laminaria and agar.

In molding the pharmaceutical composition into a suppository form, a wide variety of carriers known in the art can be used. Examples of suitable carriers include polyethylene glycol, cacao butter, higher alcohols, esters of higher alcohols, gelatin, and semisynthetic glycerides.

When the pharmaceutical composition is formulated into an injectable preparation, the resulting solution and suspension are preferably sterilized, and are isotonic with respect to the blood. In formulating the pharmaceutical composition into the form of a solution or suspension, all diluents customarily used in the art can be used. Examples of suitable diluents are water, ethyl alcohol, propylene glycol, ethoxylated isostearyl alcohol, polyoxylated isostearyl alcohol, and polyoxyethylenesorbitan fatty acid esters. Sodium chloride, glucose or glycerol may be incorporated into a pharmaceutical composition, in an amount sufficient to prepare isotonic solutions. The pharmaceutical composition may further contain ordinary dissolving aids, buffers, painalleviating agents, and optionally coloring agents, preservatives, perfumes, flavors, sweeteners, and other drugs.

The amount of the compound of this invention as an active ingredient to be incorporated into an anti-ulcer preparation is not particularly limited, and can vary over a wide range. A suitable effective amount of the compound of this invention is usually about 1 to about 70% by weight, preferably 5 to 50% by weight, based on the entire composition.

The administration method of the anti-ulcer preparation using the compound of the invention is not particularly limited and can be adequately selected according to the form of the preparation, age and sex of the patient, and symptom of disease. For example, the tablets, pills, liquid preparations, suspensions, emulsions, glanules, and capsules are orally administered. The injectable preparations are intravenously administered either alone or together with ordinary auxiliary agents such as glucose and amino acids. Furthermore, as required, the injectable preparations can singly be administered intramuscularly, intracutaneously, subcutaneously, or intraperitoneally. The suppository is administered intrarectally.

The dosage of the anti-ulcer preparation containing the compound of this invention is suitably selected according to the purpose of use, age and sex of the patient, and the symptoms of disease, etc. Usually, a preferred dosage of the compound of this invention is 0.6 to 50 mg/kg body weight per day. It is advantageous that the active ingredient is contained in a single unit dose form in an amount of 10 to 1000 mg.

Hereinafter, this invention will be described in greater detail with reference to Reference Examples, Examples and Pharmaceutical Examples.

EXAMPLES

Reference Example 1

8-Methylquinoline (4.02 g) was dissolved in carbon tetrachloride (40 ml), and N-bromosuccinimide (5.98 g) and benzoyl peroxide (0.15 g) were added to the solution, and the mixture was heated and refluxed for 3 hours. After filtering off the insoluble matter, the filtrate was concentrated. The resultant residue was recrystallized from ligroin to give 8-bromomethylquinoline (3.60 g).
Pale brown needle crystals
mp: 80° C.

Reference Example 2

8-Bromomethylquinoline (1.11 g) and sodium acetate (0.82 g) were suspended and dissolved in dimethyl formamide, and heated for 2 hours at 80° to 90° C. After completion of the reaction, dimethyl formamide was distilled off, and the residue was extracted with a mixed solvent of ethyl acetate-toluene (3:1). The solvent was distilled off to give 8-acetoxymethylquinoline (0.86 g).

Reference Example 3

To a solution of 8-acetoxymethylquinoline (12.07 g) in methanol (80 ml) was added an 30% aqueous solution of sodium hydroxide, and the mixture was heated and refluxed for 1.5 hours. After distilling off the methanol, the resulting residue was extracted with chloroform. After drying over anhydrous magnesium sulfate, the solvent was distilled off. The residue was recrystallized from ethyl acetate-n-hexane to give 8-hydroxymethylquinoline (9.21 g).
Pale yellow needle crystals
mp: 74°–75° C.

Reference Example 4

Sodium cyanoborohydride (8.80 g) was suspended in tetrahydrofuran (50 ml), and formic acid (50 ml) was added to the suspension under ice-cooling. After purging the vessel with argon, 8-acetoxymethylquinoline (5.65 g) was added thereto, and the mixture was stirred for 3 hours at room temperature. After distilling off tetrahydrofuran, water was added to the residue, and sodium hydroxide was added to the mixture under ice-cooling to adjust to alkalinic. The mixture was extracted with chloroform and dried over anhydrous magnesium sulfate, and the solvent was distilled off.

The resulting residue was purified by silica gel column chromatography [eluent: n-hexane-ethyl acetate (4:1)] to give 8-hydroxymethyl-1-ethyl-1,2,3,4-tetrahydro quinoline (2.93 g).
Yellow oil
NMR(CDCl$_3$)$\delta$: 1.27 (3H, t, J=7.5 Hz), 1.66–2.00 (2H, m), 2.85 (2H, q, J=7.5 Hz), 3.00–3.20 (2H, m), 4.00 (1H, br.), 4.75 (2H, s), 6.93 (3H, s).

Reference Example 5

1-Methyl-8-hydroxymethyl-1,2,3,4-tetrahydroquinoline (0.89 g) was dissolved in dichloromethane (30 ml), and thionyl chloride (1.09 ml) was added thereto, and the mixture was stirred for 2 hours at 45° C. After distilling off the solvent, n-hexane was added to the residue, and the solvent was distilled off under reduced pressure to give 1-methyl-8-chloromethyl-1,2,3,4-tetrahydroquinoline (1.1 g).

Reference Example 6

To 8-hydroxymethyl-1,2,3,4-tetrahydroquinoline (8.03 g) and sodium hydride (60% in oil) (1.97 g) was added tetrahydrofuran (100 ml) under ice-cooling and argon atmosphere, and the mixture was stirred for 2 hours at 70° to 75° C. At −70° C., n-butyllithium (20 ml) was added to the reaction mixture by use of a syringe, and 30 minutes after addition, a solution of methyl iodide (6.98 g) in tetrahydrofuran (30 ml) was added thereto, and the mixture was stirred for 20 hours at room temperature. After distilling off tetrahydrofuran, the resulting residue was extracted with chloroform, and dried over anhydrous magnesium sulfate. The solvent was distilled off, and the resulting residue was purified by silica gel column chromatography [eluent: n-hexane-ethyl acetate (4:1)] to give 1-methyl-8-hydroxymethyl-1,2,3,4-tetrahydroquinoline (5.00 g).

Yellow oil

NMR(CDCl$_3$) δ: 1.70–2.10 (2H, m), 2.77 (3H, s), 2.80 (2H, t, J=6 Hz), 3.00–3.20 (2H, m), 4.80 (2H, s), 5.20 (1H, br.), 6.97 (3H, s).

Reference Example 7

To a solution of ethyl magnesium bromide prepared from magnesium (12.2 g) and ethyl bromide (55 g) in tetrahydrofuran (75 ml) was added dropwise a solution of propargyl alcohol (14 g) in tetrahydrofuran (75 ml) at 0° C. After stirring the mixture for 1.5 hours at the same temperature, trimethylsilyl chloride (55 g) was added dropwise to this solution in 1 hour. The mixture was stirred for 1 hour at 50° C., and for 24 hours at room temperature. To the reaction mixture was added a saturated aqueous solution of ammonium chloride and the mixture was extracted with diethyl ether. After distilling off the solvent, the resulting residue was dissolved in a solution of ethanol-water (10:3) containing 1% of hydrochloric acid and stirred for 1 hour. The mixture was extracted with diethyl ether and dried, the solvent was distilled off. The resulting residue was distilled under reduced pressure to give 3-trimethylsilylprop-2-yn-1-ol (12 g).

Colorless oil bp: 77.5°–78° C. (12 mmHg)

Reference Example 8

To a solution of triphenylphosphine dibromide which was prepared from bromine (19.2 g) and triphenylphosphine (48 g), in dimethyl formamide (200 ml), was added a solution of 3-trimethylsilylprop-2-yn-1-ol (10.3 g) in dimethyl formamide (40 ml) at 0° C., and the mixture was stirred for 3 hours at the same temperature and then for 12 hours at 20° C. After extracting the reaction mixture with petroleum ether, the extract was washed with a saturated aqueous solution of sodium hydrogencarbonate and dried over anhydrous magnesium sulfate, then the solvent was distilled off. The resulting residue was distilled under reduced pressure to give 3-bromo-1-trimethylsilylprop-1-yne (5.35 g).

Colorless oil bp: 44°–45° C. (2 mmHg)

Reference Example 9

8-Hydroxymethylquinoline (1.0 g) was dissolved in methanol (30 ml). Platinum oxide (0.25 g) was added thereto and the mixture was subjected to catalytic reduction at 3.5 kg/cm$^2$, 40° C. After completion of the catalytic reduction, the catalyst was filtered off and the filtrate was concentrated under reduced pressure. The resulting residue was recrystallized from ethyl acetate-n-hexane to give 8-hydroxymethyl-1,2,3,4-tetrahydroquinoline (1.0 g). Yellow needle crystals mp: 67°–68° C.

Reference Example 10

In a manner analogous to Reference Example 9, the compound mentioned below was obtained using appropriate starting materials.

4-Methyl-8-hydroxymethyl-1,2,3,4-tetrahydroquinoline NMR(CDCl$_3$) δ: 1.27 (3H, d, J=7 Hz), 1.43–2.20 (2H, m), 2.77 −3.07 (1H, m), 3.17–3.50 (2H, m), 4.57 (2H, s), 6.53 (1H, t, J=8 Hz), 6.85 (1H, d, J=8 Hz), 7.02 (1H, d, J=8 Hz).

In a manner analogous to Reference Example 4, the compound obtained in Reference Example 6 and those mentioned below were obtained using appropriate starting materials.

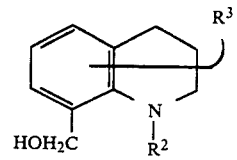

| Reference Examples | $R^2$ | $R^3$ | Crystal form (recrystallization solvent) | Melting point (°C.) |
|---|---|---|---|---|
| 11 | n-C$_4$H$_9$ | H | NMR$^{(1)}$ | |
| 12 | CH$_3$ | 4-CH$_3$ | NMR$^{(2)}$ | |
| 13 | C$_2$H$_5$ | 6-Br | Pale yellow powder (n-hexane-ethyl acetate) | 105–106 |
| 14 | C$_2$H$_5$ | 6-OCH$_3$ | NMR$^{(3)}$ | |
| 15 | CH$_3$ | 5-OCH$_3$ | NMR$^{(4)}$ | |

In a manner analogous to Reference Example 6, the compounds obtained in Reference Examples 4, and 11 to 15 and those mentioned below were obtained using appropriate starting materials.

1) NMR(CDCl$_3$) δ: 0.97 (3H, t, J=7 Hz), 1.13–2.00 (6H, m), 2.67–3.00 (4H, m), 3.00–3.23 (2H, m), 4.77 (2H, s), 6.97 (3H, brs)

2) NMR(CDCl$_3$) δ: 1.33 (2H, d, J=8 Hz), 1.43–2.27 (2H, m), 2.67–3.23 (3H, m), 2.77 (3H, s), 4.83 (2H, s), 6.93–7.37 (3H, m)

3) NMR(CDCl$_3$) δ: 1.23 (3H, t, J=8 Hz), 1.63–2.00 (2H, m), 2.60–3.17 (6H, m), 3.73 (3H, s), 4.73 (2H, s), 6.47 (1H, d, J=2 Hz), 6.57 (1H, d, J=2 Hz)

4) NMR(CDCl$_3$) δ: 1.70–2.00 (2H, m), 2.50–2.80 (2H, m), 2.74 (3H, s), 2.90–3.20 (2H, m), 3.78 (3H, s), 4.73 (2H, s), 6.46 (1H, d), 6.98 (1H, d)

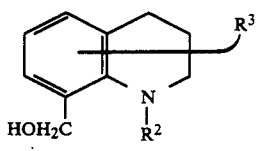

| Reference Examples | R² | R³ | NMR (CDCl₃) δ: |
|---|---|---|---|
| 16 | CH₂CH=CH₂ | H | 1.57–2.00(2H,m), 2.73(2H,t,J = 7Hz), 2.90–3.13(2H,m), 3.42(2H,d,J = 6Hz), 4.63(2H,s), 5.03–5.40(2H,m) 5.67–6.17(1H,m), 6.70–7.20(3H,m) |
| 17 | CH₂—C≡C—Si(CH₃)₃ | H | 0.17(9H,2), 1.67–2.07(2H,m), 2.80(2H,t,J = 7Hz), 3.13–3.37(2H,m), 3.72(2H,s), 4.73(2H,s), 6.77–7.13(3H,m) |
| 18 | CH₂—⌬ (benzyl) | H | 1.63–2.07(2H,m), 2.73–3.07(4H,m), 4.07(2H,s), 4.82(2H,s), 6.90–7.60(8H,m) |
| 19 | COCH₃ | H | |

Reference Example 20

Sodium cyanoborohydride (7.9 g) was dissolved in tetrahydrofuran (50 ml). After adding and dissolving 8-hydroxymethyl-4-methylquinoline (3.5 g) in the solution, formic acid (50 ml) was added dropwise thereto with stirring under ice-cooling in nitrogen stream. The mixture was stirred for 5 hours at room temperature. After completion of the reaction, water was added to the reaction mixture and the mixture was concentrated under reduced pressure. The resulting residue was adjusted to alkalinic with a sodium hydroxide aqueous solution and extracted with chloroform. After drying the extract over anhydrous magnesium sulfate, chloroform was distilled off. The resulting residue was purified by silica gel column chromatography [eluent: dichloromethane-methanol(200:1)], then 1,4-dimethyl-8-hydroxymethyl-1,2-dihydroquinoline (0.9 g) was obtained.

NMR(CDCl₃) δ: 2.08 (3H, d, J=1.5 Hz), 2.58 (3H, s), 3.50–3.70 (2H, m), 4.78 (2H, s), 5.50–5.70 (1H, m), 6.90 −7.30 (3H, m).

Reference Example 21

1,4-Dimethyl-8-hydroxymethyl-1,2-dihydroquinoline (0.9 g) was dissolved in dichloromethane (30 ml). To this solution was added dropwise thionylchloride (0.6 g) with stirring under ice-cooling, and the mixture was stirred for 30 minutes. After completion of the reaction, dichloromethane was distilled off under reduced pressure, and n-hexane was added to the residue. The mixture was concentrated under reduced pressure to give 1,4-dimethyl-8-chloromethyl-1,2-dihydroquinoline (0.8 g).

Reference Example 22

To a mixture of 2-hydroxymethylaniline (25 g), triethylamine (32 ml) and tetrahydrofuran (250 ml) was introduced phosgene generated from trichloromethyl chloroformate (12.2 ml) and active carbon at room temperature with stirring. After stirring for 1 hour at room temperature, the reaction mixture was filtered off and the filtrate was concentrated. The resulting residue was recrystallized from diethyl ether-n-hexane to give 4H-1,2-dihydro-2-oxo-[3,1]benzoxazine (22.3 g).

White needle crystals
mp: 120°–121° C.

Reference Example 23

To a solution of 4H-1,2-dihydro-2-oxo-[3,1]benzoxazine (13 g) in tetrahydrofuran (250 ml) was gradually added sodium hydride (60%) (4.2 g) at room temperature with stirring. Then the mixture was stirred for 1 hour at 80° C. After distilling off the solvent, methyl acrylate (10 ml) was added to the residue and the mixture was heated for 3 hours at 50° C. The reaction mixture was concentrated and extracted with diethyl ether, and the extract was washed with water and dried over anhydrous magnesium sulfate. The solvent was distilled to give a crude methyl 3-(4H-1,2-dihydro-2-oxo-[3,1]benzoxazin-1yl)propionate.

NMR(CDCl₃) δ: 2.80 (2H, t, J=8 Hz), 3.70 (3H, s), 4.20 (2H, t, J=8 Hz), 5.20 (2H, s), 6.96–7.48 (4H, m).

The above compound was used in the next reaction without purification.

To a solution of methyl 3-(4H-1,2-dihydro-2-oxo[3,1-]benzoxazin-1-yl)propionate obtained above in methanol (60 ml) was added a saturated aqueous solution of sodium carbonate (10 ml) and the mixture was refluxed for 6 hours. The reaction mixture was washed with diethyl ether, the water layer was adjusted to acidic with 10% aqueous solution of concentrated hydrochloric acid. The mixture was extracted with diethyl ether, and the solvent was distilled off to give 3-(4H-1,2-dihydro-2-oxo-[3,1]benzoxazin-1-yl)propionic acid (20 g).

1 NMR(CDCl₃) δ: 2.86 (2H, t, J=7 Hz), 4.22 (2H, t, J=7 Hz), 5.30 (2H, s), 6.93–7.50 (4H, m).

Reference Example 24

The polyphosphoric acid prepared from phosphorus pentoxide (50 g) and phosphoric acid (50 ml) was heated to 100° C, and 3-(4H-1,2-dihydro-2-oxo-[3,1]benzoxazin-1-yl) propionic acid (20 g) was added thereto. The mixture was heated with stirring at 100° C for 4 hours. Then water was added to the reaction mixture and the mixture was extracted with dichloromethane. After the extract was dried over anhydrous sodium sulfate and concentrated, the residue was purified by silica gel column chromatography (eluent: dichloromethane) and recrystallized from ethyl acetate-n-hexane to give 6,7-dihydro-3,7-dioxo-1H,3H,5H-pyrido[3,2,1-ij][3,1]benzoxazine (5.1 g).

White needle crystals
mp: 130°–131° C.

Regarding 1H,3H,5H-pyrido[3,2,1-ij][3,1]benzoxazine derivatives obtained above and hereinafter, the substitution position number of the skeleton was defined as below according to the Chemical Abstract, vol. 102, p. 612, 1985.

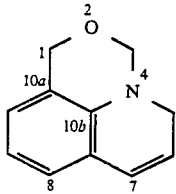

Reference Example 25

A solution of 6,7-dihydro-3,7-dioxo-1H,3H,5H-pyrido [3,2,1-ij][3,1]benzoxazine (2 g), ethylene glycol (2.2 ml) and p-toluenesulfonic acid (catalytic amount) in toluene (60 ml) was refluxed by use of Dean-Stark apparatus for 3 hours. After washing the reaction mixture with a saturated aqueous solution of sodium hydrocarbonate, the mixture was dried over anhydrous magnesium sulfate. The solvent was distilled off to give 6,7-dihydro-3-oxo-7,7-ethylenedioxy-1H,3H,5H-pyrido[3,2,1-ij][3,1]benzoxazine (2.1 g).

NMR(CDCl$_3$) δ: 2.08–2.17 (2H, m), 4.00–4.12 (2H, m), 4.12 –4.30 (4H, m), 7.03–7.50 (3H, m).

Reference Example 26

6,7-Dihydro-3-oxo-7,7-ethylenedioxy-1H,3H,5H-pyrido[3,2,1-ij][3,1]benzoxazine (4 g) was dissolved in a mixture of 10% aqueous solution of sodium hydroxide and methanol (1 : 10 v/v, 90 ml) and the solution was refluxed for 2 hours. Sequentially the solvent was distilled off and the resulting residue was extracted with dichloromethane. The extract was washed with water and dried. After distilling off the solvent, the resulting residue 8-hydroxymethyl-4,4-ethylenedioxy-1,2,3,4-tetrahydroquinoline (2.6 g).

Pale yellow plate crystals
mp: 140°–141° C.

Reference Example 27

To a solution of 8-hydroxymethyl-4,4-ethylenedioxy-1,2,3,4-tetrahydroquinoline (2.5 g) in tetrahydrofuran (30 ml) was added n-butyllithium (14.5 to 17% solution in n-hexane) (10 ml) at —40° C. and stirred for 30 minutes. Then methyl iodide (1.9 g) was added to the reaction mixture and the mixture was stirred for 3 hours at −30° C. to −10° C. and for 30 minutes at −5° C. After distilling off the solvent, n-hexane-ethyl acetate was added to the resulting residue and the insoluble matter was filtered off. The filtrate was concentrated to give 8-hydroxymethyl-4,4-ethylenedioxy-1-methyl-1,2,3,4-tetrahydroquinoline (1.9 g).

NMR(CDl$_3$) δ: 2.00–2.13 (2H, m), 2.83 (3H, s), 3.27–3.35 (2H, m), 4.05–4.30 (4H, m), 4.80 (2H, s), 7.03 (1H, t, J=6 Hz), 7.18 (1H, dd, J=1.6 Hz), 7.39 (1H, dd, J=1.6 Hz).

Reference Example 28

To a solution of 6,7-dihydro-3,7-dioxo-1H,3H,5-pyrido[3,2,1-ij][3,1]benzoxazine (1 g) in methanol (20 ml) was added sodium borohydride (186 mg) by portions at room temperature and the mixture was stirred for 30 minutes at the same temperature. After distilling off the solvent, the resulting residue was extracted with dichloromethane. The extract was washed with water and dried, and the solvent was distilled off to give 6,7-dihydro-3-oxo-7-hydroxy-1H,3H,5H-pyrido[3,2,1-ij][3,1]benzoxazine (0.9 g).

NMR(CDl$_3$) δ: 2.03–2.18 (2H, m), 3.80–4.00 (1H, m), 4.00 –4.20 (1H, m), 4.84 (1H, q, J=5 Hz), 5.21 (2H, s), 7.06 (2H, d, J=5 Hz), 7.38 (1H, t, J=5 Hz).

Reference Example 29

To a solution of 6,7-dihydro-3-oxo-7-hydroxy-1H,3H,5-pyrido[3,2,1-ij][3,1]benzoxazine (4.3 g) in dimethyl formamide (50 ml) was added sodium hydride (60%, 941 mg) at room temperature and the mixture was stirred for 30 minutes. To this mixture was added a solution of methyl iodide (3.4 g) in dimethyl formamide (5 ml) and the mixture was stirred for 1 hour at the same temperature. Sequentially the reaction mixture was extracted with a mixed solvent of benzene-ethyl acetate (1 : 3). The extract was washed with water and dried, the solvent was distilled off and the resulting residue was purified by silica gel column chromatography (eluent: dichloromethane) to give 6,7-dihydro-3-oxo-7-methoxy-1H,3H,5H-pyrido-[3,2,1-ij][3,1]benzoxazine (4.3 g).

NMR(CDl$_3$) δ: 1.85–2.08 (1H, m), 2.15–2.31 (1H, m), 3,42 (3H, s), 3.70–3.87 (1H, m), 4.02–4.18 (1H, m), 4.29 (1H, t, J=4 Hz), 5.20 (2H, s), 6.96–7.12 (2H, m), 7.22–7.32 (1H, m).

Reference Example 30

6,7-Dihydro-3-oxo-7-methoxy-1H,3H,5H-pyrido[3,2,1-ij][3,1]benzoxazine (4.3 g) was dissolved in a mixture of 10% aqueous solution of sodium hydroxide and methanol (1:10 v/v, 55 ml), and the mixture was refluxed for 2 hours. After distilling off the solvent, the resulting residue was extracted with dichloromethane. The extract was washed with water and dried, the solvent was removed. The resultant residue was purified by silica gel column chromatography [eluent: n-hexane-ethyl acetate (4:1 v/v)]to give 8-hydroxymethyl-4-methoxy-1,2,3,4-tetrahydroquinoline (2.4 g).

NMR(CDl$_3$) δ: 1.65–1.88 (1H, m), 2.01–2.18 (1H, m), 2.92 (1H, brs), 3.16–3.50 (2H, m), 3.33 (3H, s), 4.20 (1H, t, J=3 Hz), 4.37 (1H, d, J=13 Hz), 4.44 (1H, d, J=13 Hz), 4.95 (1H, brs), 6.55 (1H, t, J=7 Hz), 6.91 (1H, dd, J=2.7 Hz), 7.06 (1H, dd, J=2.7 Hz).

Reference Example 31

In a manner analogous to Reference Example 27, the compound mentioned below was obtained using appropriate starting materials.

8-hydroxymethyl-4-methoxy-1-ethyl-1,2,3,4-tetrahydroquinoline

NMR(CDl$_3$) δ: 1.25 (3H, t, J=7 Hz), 1.93–2.05 (2H, m), 2.96 (2H, q, J=7 Hz), 3.11–3.25 (2H, m), 3.42 (3H, s), 4.28 (1H, t, J=5 Hz), 4.51 (1H, brs), 4.69 (1H, d, J=13 Hz), 4.79 (1H, d, J=13 Hz), 6.98 (1H, t, J=7 Hz), 7.16 (1H, dd, J=2.7 Hz), 7.22 (1H, dd, J=2.7 Hz).

Reference Example 32

8-Hydroxymethyl-1-ethyl-4-oxo-1,2,3,4-tetrahydroquinoline (1.44 g) was dissolved in dimethyl formamide (2 ml). Imidazole (1.57 g) and t-butyl dimethylsilyl chloride (1.16 g) were added to the solution and the mixture was stirred overnight at room temperature. Water was added to the reaction mixture and the mixture was extracted with ethyl acetate-toluene. After the extract was dried over anhydrous magnesium sulfate, the solvent was distilled off. The resulting residue was purified by silica gel column chromatography [eluent: n-hexane-ethyl acetate (3: 1) ] to give 4-oxo-8-t-butyl-dimethylsilyloxymethyl-1-ethyl-1,2,3,4-tetrahydroquinoline (2.18 g).

Yellow oil

Reference Example 33

4-oxo-8-t-butyldimethylsilyloxymethyl-1-ethyl-1,2,3,4-tetrahydroquinoline (2.17 g) was dissolved in methanol (20 ml). To this solution was added sodium borohydride (0.26 g) at room temperature, and the mixture was stirred for 10 minutes. Water was added to the reaction mixture and the solvent was distilled off to give 8-t-butyldimethylsilyloxymethyl-4-hydroxy-1-ethyl-1,2,3,4-tetrahydroquinoline (2.30 g).

Reference Example 34

8-t-butyldimethylsilyloxymethyl-4-hydroxy-1-ethyl-1,2,3,4-tetrahydroquinoline (2.19 g) was dissolved in dimethyl formamide (15 ml), followed by addition of sodium hydride (60% in oil, 0.33 g), and allyl bromide (0.99 g) was added thereto under ice-cooling. The mixture was stirred for 2.5 hours at the same temperature. Furthermore sodium hydride (60% in oil, 0.16 g) and allyl bromide (0.48 g) were added to the reaction mixture and the mixture was stirred overnight at room temperature. Water was added to the reaction mixture. The mixture was extracted with ethyl acetate-toluene and dried over anhydrous magnesium sulfate, and the solvent was distilled off. The resulting residue was purified by silica gel column chromatography [eluent: n-hexane-ethyl acetate (6 : 1)]to give 8-t-butyldimethylsilyloxymethyl-4-allyloxy-1-ethyl-1,2,3,4-tetrahydroquinoline (1.83 g).

Yellow oil

Reference Example 35

8-t-Butyldimethylsilyloxymethyl-4-allyloxy-1-ethyl-1,2,3,4-tetrahydroquinoline (1.81 g) was dissolved in tetrahydrofuran (20 ml), and to this solution was added dropwise 1M tetrabutylammonium fluoride-tetrahydrofuran solution (6 ml) under ice-cooling. The mixture was stirred for 1 hour at the same temperature. Water was added to the reaction mixture and after distilling off tetrahydrofuran, the residue was extracted with dichloromethane. The extract was dried over anhydrous magnesium sulfate and distilled off then 8-hydroxymethyl-4-allyloxy-1-ethyl-1,2,3,4-tetrahydroquinoline (1.30 g) was obtained.

Yellow oil

Reference Example 36

6,7-Dihydro-3,7-dioxo-1H,3H,5H-pyrido[3,2,1-ij][3,1]benzoxazine (5 g), hydroxylamine hydrochloride (2.1 g) and sodium acetate (7.5 g) were dissolved in a mixed solvent of ethanol-water (5:1) (90 ml) and the mixture was refluxed for 2 hours. After completion of the reaction, the solvent was distilled off and the resulting residue was poured into water. Crystals which precipitated were collected by filtration and dried to give 6,7-dihydro-3-oxo-7-hydroxyimino-1H,3H,5H-pyrido[3,2,1-ij][3,1]benzoxazine. The compound was dissolved in acetic acid (150 ml) and platinum oxide (250 mg) was added thereto. The mixture was subjected to catalytic reduction at 50° C. and 4 atmospheres. After completion of the catalytic reduction, catalyst was filtered off and the filtrate was concentrated to give 6,7-dihydro-3-oxo-7-amino-1H,3H,5H-pyrido [3,2,1-ij][3,1]benzoxazine (5 g).

Yellow oil

NMR(CDCl$_3$) δ: 2.13–2.32 (2H, m), 3.78–4.13 (2H, m), 4.35 (1H, brs), 7.02–7.13 (2H, m), 7.36–7.45 (1H, m)

Reference Example 37

6,7-Dihydro-3-oxo-7-amino-1H,3H,5H-pyrido[3,2,1-ij]-[3,1]benzoxazine (5 g) was dissolved in a mixed solution of formic acid (10 ml) and 37% aqueous solution of formalin (10 ml), and stirred for 5 hours at 100° C. The residue, obtained by removing the solvent, was extracted with dichloromethane. The extract was washed with a saturated aqueous solution of sodium hydrogencarbonate and dried over anhydrous magnesium sulfate, and the solvent was distilled off to give 6,7-dihydro-3-oxo-7-dimethylamino-1H,3H,5H-pyrido[3,2,1-ij][3,1]benzoxazine (4.8 g).

Red viscous oil

1 NMR(CDCl$_3$) δ: 1.94–2.11 (2H, m), 2.29 (6H, s), 3.53 (1H, t, J=6 Hz), 3.59–3.76 (1H, m), 4.07–4.25 (1H, m), 5.17 (2H, s), 6.95–7.05 (2H, m), 7.34 −7.46 (1H, m).

Reference Example 38

To a solution of 4-oxo-1-ethyl-8-hydroxymethyl-1,2,3,4-tetrahydroquinoline (3.80 g) in methanol (40 ml), molecular sieve 3A (4 g), cyclopropylamine (11.42 g) and p-toluenesulfonic acid (catalytic amount) were added and the mixture was stirred for 8 hours at 65° C. After ice-cooling the reaction mixture, molecular sieve 3A was filtered off, then sodium borohydride (1.05 g) was added thereto, and the mixture was stirred for 1 hour at room temperature. A small amount of water was added to the reaction mixture, and methanol was distilled off. The residue was extracted with dichloromethane and dried over anhydrous magnesium sulfate. The solvent was distilled off and the resulting residue was purified by silica gel column chromatography [eluent: n-hexane-ethyl acetate (3:1)]to give 4-cyclopropylamino-8-hydroxymethyl-1-ethyl-1,2,3,4-tetrahydroquinoline (3.69 g).

Pale yellow oil

NMR(CDCl$_3$) δ: 0.33–0.56(4H, m), 1.26 (3H, t, J=7.5 Hz), 1.85– 2.15 (2H, m), 2.15–2.30 (1H, m), 2.93 (2H, q, J=7.5 Hz), 3.00–3.30 (2H, m), 3.85 (1H, t, J =5.3 Hz), 4.74 (2H, dd, J=13.5 Hz), 6.95 (1H, t, J=7.3 Hz), 7.09 (1H, dd, J=7.3 Hz), 7.24 (1H, dd, J=7.3 Hz).

Reference Example 39

Acetic anhydride (0.5 ml) and formic acid (0.25 ml) were stirred for 1 hour at 60° C, and to this mixture 4-cyclopropylamino-8-hydroxymethyl-1-ethyl-1,2,3,4-tetrahydroquinoline (0.37 g) was added under ice-cooling and the mixture was stirred overnight at room temperature The reaction mixture was adjusted to alkalinic with 30% aqueous solution of sodium hydroxide under ice-cooling, stirred for 0.5 hour, sequentially extracted with dichloromethane. The extract was dried over anhydrous magnesium sulfate The residue, obtained by distilling off the solvent, was purified by silica gel column chromatography [eluent: dichloromethane-methanol (75:1)]to give 4-(N-formyl-N-cyclopropylamino)-8-hydroxymethyl1-ethyl-1,2,3,4-tetrahydroquinoline (0.35 g).

Colorless oil

NMR(CDCl$_3$) δ: 0.45–0.85 (4H, m), 1.29 (3H, t, J=7.5 Hz), 1.75 −2.10 (1H, m), 2.30–2.70 (2H, m), 2.80–3.45 (4H, m), 4.77 (2H, dd, J=13.5 Hz), 4.82 (1H, br.), 5 64 (1H, t, J=8.5 Hz), 6.85–7.20 (3H, m), 8.50 (1H, s).

Reference Example 40

To a solution of 4-(N-formyl-N-cyclopropylamino)-8-hydroxymethyl-1-ethyl-1,2,3,4-tetrahydroquinoline (0.34 g) in tetrahydrofuran (10 ml), lithium aluminum hydride (0.10 g) was added under ice-cooling and the mixture was refluxed gently for 1.5 hours. A saturated aqueous solution of Rochelle salt was added to the reaction mixture under ice-cooling, followed by addition of diethyl ether, the mixture was stirred for 1 hour at room temperature. After filtering off the precipitates, the organic layer was dried over anhydrous magnesium sulfate. The solvent was distilled off to give 4-(N-methyl-N-cyclopropylamino)-8-hydroxymethyl-1-ethyl-1,2,3,4-tetrahydroquinoline (0.30 g).

White powder

Reference Example 41

To a solution of 6,7-dihydro-3,7-dioxo-1H,3H,5H-pyrido[3,2,1-ij][3,1]benzoxazine (6.10 g) in methanol (100 ml) were added molecular sieve 3A (12 g), p-toluenesulfonic acid (catalytic amount) and allylamine (50 ml), and the mixture was refluxed overnight. After cooling the reaction mixture, molecular sieve 3A was filtered off and sodium borohydride (1.70 g) was added to the filtrate under ice-cooling, then the mixture was stirred for 1 hour at room temperature. To the reaction mixture was added a small amount of water, and methanol was distilled off. The residue was extracted with dichloromethane and dried over anhydrous magnesium sulfate. After distilling off the solvent, the resulting residue was purified by silica gel column chromatography [eluent: n-hexane-ethyl acetate (3:1)]to give 6,7-dihydro-3-oxo-7-allylamino-1H,3H,5H-pyrido[3,2,1-ij][3,1]benzoxazine (5.89 g).

Yellow oil

NMR(CDCl$_3$) δ: 1.90–2.10 (2H, m), 3.25–3.45 (2H, m), 3.75–3.90 (2H, m), 4.00–4.15 (1H, m), 5.10–5.35 (2H, m), 5.19 (2H, s), 5.85–6.05 (1H, m), 6.95–7.10 (2H, m), 7.20–7.30 (1H, m).

Reference Example 42

6,7-Dihydro-3-oxo-7-allylamino-1H,3H,5H-pyrido[3,2,1-ij][3,1]benzoxazine (5.86 g) was dissolved in a solution of formic acid (7 ml) and 35% formalin (7 ml), and the solution was stirred for 2 hours at 90° C. Formic acid and formalin were distilled off under reduced pressure, and to this mixture were added ice water and dichloromethane, and the mixture was adjusted to alkalinic with sodium carbonate. The mixture was extracted with dichloromethane, dried over anhydrous magnesium sulfate, and distilled off to give 6,7-dihydro-3-oxo-7-(N-methyl-N-allylamino)- 1H,3H,5H-pyrido[3,2,1-ij][3,1]benzoxazine (5.90 g).

Orange colored oil

NMR (CDCl$_3$) δ: 1.80–2.20 (2H, m), 2.24 (3H, s), 3.00–3.25 (2H, m), 3.50–3.60 (1H, m), 3.80–3.90 (1H, m), 4.25–4.35 (1H, m), 5.10–5.30 (2H, m), 5.19 (2H, s), 5.80–6.00 (1H, m), 6.90–7.10 (2H, m), 7.56 (1H, dd, J =6.5 Hz).

Reference Example 43

To a solution of 6,7-dihydro-3-oxo-7-(N-methyl-N-allylamino)-1H,3H,5H-pyrido[3,2,1-ij][3,1]benzoxazine (5.89 g) in methanol (80 ml) was added 15% aqueous solution of sodium hydroxide (20 ml) and the mixture was refluxed for 6 hours. After distilling off methanol and extracting with dichloromethane, the extract was dried over anhydrous magnesium sulfate. The solvent was distilled off to give 4-(N-methyl-N-allylamino)-8-hydroxymethyl-1,2,3,4-tetrahydroquinoline (4.83 g).

NMR (CDCl$_3$) δ: 1.70 (1H, br.), 1.93 (2H, q, J=7.0 Hz), 2.24 (3H, s), 2.95–3.55 (4H, m), 3.89 (1H, t, J=7.0 Hz), 4 59 (2H, dd J=13.6 Hz), 4.80 (1H, br.), 5.00–5.25 (2H, m), 5.75–6.00 (1H, m), 6.60 (1H, t, J=7.5 Hz), 6.91 (1H, dd, J=7.5 Hz), 7.42 (1H, dd, J= 7.5 Hz).

Reference Example 44

To a suspension of methyltriphenyl phosphonium bromide (11.85 g) in tetrahydrofuran (100 ml), n-butyl lithium (10.2 ml) was added dropwise with stirring in nitrogen flow at −40° C. The temperature was raised to −20° C. over 30 minutes, a solution of 8-(t-butyldimethylsilyloxymethyl)-4-oxo-1-ethyl-1,2,3,4-tetrahydroquinoline (3.8 g) in tetrahydrofuran (100 ml) was added dropwise thereto. The temperature was raised gradually to the room temperature, the mixture was stirred for 2.5 hours. Water was added to the reaction mixture, and the mixture was extracted with dichloromethane and dried, then the solvent was distilled off under reduced pressure. The resulting residue was purified by silica gel column chromatography [eluent: n-hexane-ethyl acetate (8:1)]to give 8-(t-butyldimethylsilyloxymethyl)-4-methylene-1-ethyl-1,2,3,4tetrahydroquinoline (3.4 g).

Reference Example 45

To a solution of 8-(t-butyldimethylsilyloxymethyl)-4-methylene-1-ethyl-1,2,3,4-tetrahydroquinoline (2.04 g) in tetrahydrofuran ( 50 ml), 10M solution (3.2 m) of borane-dimethylsulfide complex in tetrahydrofuran was added dropwise with stirring under ice-cooling. After stirring the mixture for 2 hours at room temperature, water was added to the reaction mixture, and furthermore 3N aqueous solution of sodium hydroxide (10 ml) and 30% hydrogen peroxide (10 ml) were added thereto. After stirring for 2 hours at room temperature, the reaction mixture was subjected to salting-out and extracted with dichloromethane. After the extract was dried, the solvent was distilled off under reduced pressure, and the resulting residue was purified by silica gel column chromatography [eluent: n-hexane-ethyl acetate (3:1)]to give 8-(t-butyldimethylsilyloxymethyl)-4-hydroxymethyl-1-ethyl-1,2,3,4-tetrahydroquinoline (1.98 g).

Reference Example 46

To a solution of 8-(t-butyldimethylsilyloxymethyl)-4-hydroxymethyl-1-ethyl-1,2,3,4-tetrahydroquinoline (1.98 g) in pyridine (5 ml), acetic anhydride was added dropwise with stirring under ice-cooling and the mixture was stirred for 2 hours at room temperature. Pyridine was distilled off under reduced pressure, and the resultant residue was extracted with dichloromethane. After washing with a saturated aqueous solution of copper sulfate and with water in this order, the mixture was dried and the solvent was distilled off under reduced pressure to give 8-t-butyldimethylsilyloxymethyl-4-acetyloxymethyl-1-ethyl-1,2,3,4-tetrahydroquinoline (2.23 g).

Reference Example 47

To a solution of 8-(t-butyldimethylsilyloxymethyl)-4-oxo-1-ethyl-1,2,3,4-tetrahydroquinoline (3.1 g) in tetrahydrofuran (30 ml), sodium hydride (60%, 0.48 g) and methyl iodide (0.8 ml) were added under ice-cooling, and the mixture was stirred for 1 hour. Moreover sodium hydride (60%, 0.48 g) and methyl iodide (0.8 ml) were added to the reaction mixture and the mixture was stirred for 1.5 hours under ice-cooling. After tetrahydrofuran was distilled off, the residue was extracted with ethyl acetate and the extract was dried over anhydrous magnesium sulfate, then the solvent was distilled off. The residue was purified by silica gel column chromatography [eluent: n-hexane-ethyl acetate (10:1)]to give 8-(t-butyldimethylsilyloxymethyl)-4-oxo-3,3-dimethyl-1-ethyl-1,2,3,4-tetrahydroquinoline (2.27 g).
Red colored oil

Reference Example 48

To a solution of 8-(t-butyldimethylsilyloxymethyl)- c 4-oxo-3,3-dimethyl-1-ethyl-1,2,3,4-tetrahydroquinoline (2.27 g) in tetrahydrofuran (30 ml), 1m solution (7 ml) of tetrabutylammonium fluoride in tetrahydrofuran was added dropwise and the mixture was stirred for 45 minutes under ice-cooling. Water was added to the reaction mixture, and tetrahydrofuran was distilled off. The residue was extracted with dichloromethane and dried over anhydrous magnesium sulfate, and the solvent was distilled off. The residue was purified by silica gel column chromatography [eluent:n-hexane-ethyl acetate (4:1)] to give 8-hydroxymethyl-4-oxo-3,3-dimethyl-1-ethyl-1,2,3,4-tetrahydroquinoline (1.55 g).
Yellow oil

Example Reference 50

To a solution of 8-(t-butyldimethylsilyloxymethyl)-4-oxo-3,3-dimethyl-1-ethyl-1,2,3,4-tetrahydroquinoline (1.60 g) in methanol (20 ml) was added sodium borohydride (0.30 g) and the mixture was stirred for 30 minutes. Methanol was distilled off and the resulting residue was extracted with dichloromethane. After drying the extract over anhydrous magnesium sulfate, the solvent was distilled off. The resulting crude 8-(t-butyldimethylsilyloxymethyl)-4-hydroxy-3,3-dimethyl-1-ethyl-1,2,3,4-tetrahydroquinoline was dissolved in dimethyl formamide (15 ml), followed by addition of sodium hydride (60%, 0.24 g), methyl iodide (0.85 g) was added thereto. The mixture was stirred overnight at room temperature. The reaction mixture was extracted with ethyl acetate-toluene and dried over anhydrous magnesium sulfate, and the solvent was distilled off. The resulting residue was purified by silica gel column chromatography [eluent:n-hexane-ethyl acetate (20:1)] to give 8-(t-butyldimethylsilyloxymethyl)- 4-methoxy-3,3-dimethyl-1-ethyl-1,2,3,4-tetrahydroquinoline (1.40 g).
Colorless oil

Example Reference 49

To a solution of 8-(t-butyldimethylsilyloxymethyl)-4-methoxy-3,3-dimethyl-1-ethyl-1,2,3,4-tetrahydroquinoline (1.40 g) in tetrahydrofuran (20 ml), 1M solution (4.2 ml) of tetrabutylammonium fluoride in tetrahydrofuran was added dropwise under ice-cooling. After the mixture was stirred for 45 minutes, tetrahydrofuran was distilled off and the residue was extracted with dichloromethane. The extract was dried over anhydrous magnesium sulfate and the solvent was distilled off. The resulting residue was purified by silica gel column chromatography [eluent:n-hexane-ethyl acetate (6:1)] to give 8-hydroxymethyl-4-methoxy-3,3-dimethyl-1-ethyl-1,2,3,4-tetrahydroquinoline (0.75 g).
Colorless oil

EXAMPLE 1

A solution of 5-methoxy-2-mercaptobenzimidazole(0.9 g), sodium hydride (60% in oil, 0.20 g) and 18-crown-6(i.e. 1,4,7,10,13,16-hexaoxacyclooctadecane) (50 mg) in dimethyl formamide (15 ml) was stirred for 20 minutes at room temperature. To the mixture was added a solution of 1-methyl-8-chloromethyl-1,2,3,4-tetrahydroquinoline hydrochloride (1.1 g) in dimethyl formamide (15 ml) and the solution was stirred for 20 hours at room temperature. Dimethyl formamide was distilled off, and chloroform, 30% aqueous solution of sodium hydroxide and water were added to the resulting residue. The mixture was stirred for 2 hours and extracted with chloroform. After drying over anhydrous magnesium sulfate, the solvent was distilled off. The resultant residue was purified by silica gel column chromatography [eluent:n-hexane-ethyl acetate (4:1)] to give 8-(5-methoxy-2-benzimidazolyl)thiomethyl-1-methyl-1,2,3,4-tetrahydroquinoline (0.80 g).

NMR(CDCl$_3$) δ: 1.60–2.00 (2H, m), 2.70 (2H, t, J=7 Hz), 2,73 (3H, s), 2.83–3.23 (2H, m), 3.73 (3H, s), 4.30 (2H, s), 6.67–7.40 (6H, m), 12.50 (1H, br.).

In a manner analogous to Example 1, the compounds shown in the table below were obtained using appropriate starting materials.

In the column of "bond between the 3- and 4-positions of the quinoline skeleton" in the table, the symbol "s" means a single bond and "d" means a double bond.

| Example No. | R¹ | m | A | R² | R³ | n | bond between the 3- and 4-positions of the quinoline skeleton | Crystal form (recrystallization solvent) | Melting point (°C.) |
|---|---|---|---|---|---|---|---|---|---|
| 2 | H | 1 | CH₂ | C₂H₅ | H | 1 | s | Colorless needle crystals (ethyl acetate-n-hexane) | 153–153.5 |
| 3 | 5-CH₃ | 1 | CH₂ | C₂H₅ | H | 1 | s | NMR⁽¹⁾ | |
| 4 | 5-OCH₃ | 1 | CH₂ | C₂H₅ | H | 1 | s | NMR⁽²⁾ | |
| 5 | 5-F | 1 | CH₂ | C₂H₅ | H | 1 | s | Yellow powder (diethyl ether-n-hexane) | 125–126 |
| 6 | 5-F,6-F | 2 | CH₂ | C₂H₅ | H | 1 | | NMR⁽³⁾ | |
| 7 | 5-F | 2 | CH₂ | C₂H₅ | H | 1 | | NMR⁽⁴⁾ | |
| 8 | 6-OCH₃ 5-OC₂H₅ 6-F | 2 | CH₂ | C₂H₅ | H | 1 | s | NMR⁽⁵⁾ | |
| 9 | 5-Cl | 1 | CH₂ | C₂H₅ | H | 1 | s | NMR⁽⁶⁾ | |
| 10 | 5-COCH₃ | 1 | CH₂ | C₂H₅ | H | 1 | s | NMR⁽⁷⁾ | |
| 11 | 5-CF₃ | 1 | CH₂ | C₂H₅ | H | 1 | s | NMR⁽⁸⁾ | |
| 12 | 4-CH₃ | 1 | CH₂ | C₂H₅ | H | 1 | s | NMR⁽⁹⁾ | |
| 13 | 4-CH₃ 6-CH₃ | 2 | CH₂ | C₂H₅ | H | 1 | s | NMR⁽¹⁰⁾ | |
| 14 | 5-CH₃ | 2 | CH₂ | C₂H₅ | H | 1 | s | Pale yellow powder (diethyl ether-n-hexane) | 153–156 |
| 15 | 6-CH₃ | 1 | CH₂ | CH₃ | H | 1 | s | Colorless needle crystals (ethyl acetate-n-hexane) | 140–142 |
| 16 | 5-F | 1 | CH₂ | CH₃ | H | 1 | s | Yellow needle crystals (ethyl acetate-n-hexane) | 128–129.5 |
| 17 | 5-CH₃ | 1 | CH₂ | CH₃ | H | 1 | s | Colorless needle crystals (ethyl acetate-n-hexane) | 150–152.5 |
| 18 | 5-Cl | 1 | CH₂ | CH₃ | H | 1 | s | NMR⁽¹¹⁾ | |
| 19 | 4-CH₃ | 1 | CH₂ | CH₃ | H | 1 | s | NMR⁽¹²⁾ | |
| 20 | 5-F | 2 | CH₂ | CH₃ | H | 1 | s | NMR⁽¹³⁾ | |
| 21 | 6-OCH₃ | 1 | CH₂ | CH₂CH=CH₂ | H | 1 | s | NMR⁽¹⁴⁾ | |
| 22 | H | 1 | CH₂ | CH₂CH=CH₂ | H | 1 | s | NMR⁽¹⁵⁾ | |
| 23 | 5-OCH₃ | 1 | CH₂ | CH₂CH=CH₂ | H | 1 | s | NMR⁽¹⁶⁾ | |
| 24 | 5-F | 1 | CH₂ | n-C₄H₉ | H | 1 | s | NMR⁽¹⁷⁾ | |
| 25 | H | 1 | CH₂ | n-C₄H₉ | H | 1 | s | NMR⁽¹⁸⁾ | |
| 26 | 5-CH₃ | 1 | CH₂ | n-C₄H₉ | H | 1 | s | NMR⁽¹⁹⁾ | |
| 27 | 5-OCH₃ | 1 | CH₂ | CH₂C≡CH | H | 1 | s | White powder (dichloromethane-diethyl ether) | 122.0–122.5 |
| 28 | H | 1 | CH₂ | CH₂C≡CH | H | 1 | s | Yellow powder (dichloromethane-diethyl ether) | 114.0–115.0 |
| 29 | 5-CH₃ | 1 | CH₂ | 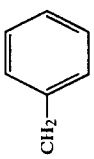 | H | 1 | s | White powder (ethyl acetate) | 172.5–173.5 |

-continued

| No. | R1 | n | A | R2 | R3 | m | config | Appearance (recryst. solvent) | mp (°C) |
|---|---|---|---|---|---|---|---|---|---|
| 30 | 5-CH₃ | 1 | CH₂ | CH₂–C₆H₅ | H | 1 | s | White powder (ethyl acetate) | 169.5–170.0 |
| 31 | H | 1 | CH₂ | CH₃ | 4-CH₃ | 1 | s | NMR(20) | |
| 32 | 5-F, 6-OCH₃ | 2 | CH₂ | CH₃ | 4-CH₃ | 1 | s | NMR(21) | |
| 33 | H | 1 | CH₂ | C₂H₅ | 6-Br | 1 | s | NMR(22) | |
| 34 | 4-CH₃, 6-CH₃ | 2 | CH₂ | CH₃ | H | 1 | s | NMR(23) | |
| 35 | H | 1 | CH₂ | CH₂C≡CSi(CH₃)₃ | H | 1 | s | White powder (dichloromethane–diethyl ether) | 140.5–141.5 |
| 36 | 5-CH₃ | 1 | CH₂ | CH₂C≡CSi(CH₃)₃ | H | 1 | s | Pale brown powder (dichloromethane–diethyl ether) | 146.0–148.0 |
| 37 | 5-COCH₃ | 1 | CH₂ | CH₃ | H | 1 | s | NMR(24) | |
| 38 | 5-F, 6-OCH₃ | 2 | CH₂ | C₂H₅ | 6-Br | 1 | s | NMR(25) | |
| 39 | H | 1 | CH₂ | C₂H₅ | 6-OCH₃ | 1 | s | Pale brown powder (ethyl acetate–n-hexane) NMR(26) | 142–143 |
| 40 | 5-F, 6-OCH₃ | 2 | CH₂ | C₂H₅ | 6-OCH₃ | 1 | s | NMR(27) | |
| 41 | 5-CO₂CH₃ | 1 | CH₂ | CH₃ | H | 1 | s | NMR(28) | |
| 42 | 5-OC₂H₅, 6-F | 2 | CH₂ | CH₃ | H | 1 | s | White powder (ethyl acetate–diethyl ether–n-hexane) NMR(29) | 112–114 |
| 43 | 5-F, 6-CH₃ | 2 | CH₂ | C₂H₅ | H | 1 | s | | |
| 44 | 5-F, 6-CH₃ | 2 | CH₂ | C₂H₅ | H | 1 | s | | |
| 45 | 5-F | 1 | CH₂ | C₂H₅ | 6-OCH₃ | 1 | s | Brown powder (ethyl acetate–n-hexane) NMR(30) | 160.0–162.0 |
| 46 | 5-F, 6-OCH₃ | 2 | CH₂ | CH₂CH=CH₂ | H | 1 | s | NMR(31) | |
| 47 | 4-CH₃ | 1 | CH₂ | CH₂CH=CH₂ | H | 1 | s | NMR(32) | |
| 48 | 4-CH₃, 6-CH₃ | 2 | CH₂ | CH₂CH=CH₂ | H | 1 | s | | |
| 49 | 5-CH₃ | 1 | CH₂ | CH₂CH=CH₂ | H | 1 | s | Colorless needle crystals (diethyl ether) NMR(33) | 143–145 |
| 50 | 5-F, 6-OC₂H₅ | 2 | CH₂ | CH₂CH=CH₂ | H | 1 | s | | |
| 51 | 5-Cl | 1 | CH₂ | CH₂CH=CH₂ | H | 1 | s | NMR(34) | |
| 52 | 5-COCH₃ | 1 | CH₂ | CH₂CH=CH₂ | H | 1 | s | NMR(35) | |

-continued

| | | | | | | | |
|---|---|---|---|---|---|---|---|
| 53 | H | 1 | CH$_2$ |  | H | 1 | White powder (n-hexane-ethyl acetate) | 168–169 |
| 54 | 5-CH$_3$ | 1 | CH$_2$ | (4-F-phenyl) | H | 1 | s | White powder (dichloromethane-diethyl ether) | 171–171.5 |
| 55 | 5-F 6-OCH$_3$ | 2 | CH$_2$ | (4-F-phenyl) | H | 1 | s | White powder (dichloromethane-diethyl ether) | 143–144 |
| 56 | 5-OCH$_3$ | 1 | CH$_2$ | CH$_2$C≡CH | H | 1 | s | NMR(36) |
| 57 | 5-F 6-OCH$_3$ | 2 | CH$_2$ | CH$_2$C≡CH | H | 1 | s | NMR(37) |
| 58 | 5-F | 1 | CH$_2$ | CH$_2$CH=CH$_2$ | 4-CH$_3$ | 1 | s | NMR(38) |
| 59 | 6-OCH$_3$ | 2 | CH$_2$ | CH$_2$CH=CH$_2$ | 4-CH$_3$ | 1 | s | Colorless needle crystals (ethyl acetate) | 165–165.5 |
| 60 | H | 1 | CH$_2$ | —CH$_2$-cyclopropyl | H | 1 | s | NMR(39) |
| 61 | 5-F 6-OCH$_3$ | 2 | CH$_2$ | —CH$_2$-cyclopropyl | H | 1 | s | NMR(40) |
| 62 | H | 1 | CH$_2$ | CH$_2$CF$_3$ | H | 1 | s | White powder (dichloromethane) | 168–169 |
| 63 | 5-CH$_3$ | 1 | CH$_2$ | CH$_2$CF$_3$ | H | 1 | s | White powder (dichloromethane-diethyl ether) | 158–159 |
| 64 | 5-F 6-OCH$_3$ | 2 | CH$_2$ | CH$_2$CF$_3$ | H | 1 | s | White powder (dichloromethane-diethyl ether) | 133–134 |
| 65 | H | 1 | CH$_2$ | C$_2$H$_5$ | 4-CH$_3$ | 1 | s | White powder (diethyl ether) | 135.5–136.5 |
| 66 | 5-F 6-OCH$_3$ | 2 | CH$_2$ | C$_2$H$_5$ | 4-CH$_3$ | 1 | s | NMR(41) |
| 67 | 5-COCH$_3$ | 1 | CH$_2$ | C$_2$H$_5$ | 4-CH$_3$ | 1 | s | NMR(42) |
| 68 | H | 1 | CH$_2$ | CH$_2$CH=CH$_2$ | 3-CH$_3$ | 1 | s | Colorless needle crystals (diethyl ether) | 151.5–152 |
| 69 | 5-CH$_3$ | 1 | CH$_2$ | CH$_2$CH=CH$_2$ | 3-CH$_3$ | 1 | s | Colorless needle crystals (diethyl ether-n-hexane) | 64–67 |
| 70 | 5-OCH$_3$ | 1 | CH$_2$ | CH$_2$CH=CH$_2$ | 3-CH$_3$ | 1 | s | Colorless needle crystals (diethyl ether) | 70–72 |
| 71 | 5-F | 1 | CH$_2$ | CH$_2$CH=CH$_2$ | 3-CH$_3$ | 1 | s | Colorless needle crystals | 72–75 |

| No. | Subst. | n | -A- | R | Subst.2 | m | s/d | Form (solvent) / mp |
|---|---|---|---|---|---|---|---|---|
| 72 | 5-F, 6-OCH$_3$ | 2 | CH$_2$ | CH$_2$CH=CH$_2$ | 3-CH$_3$ | 1 | s | (diethyl ether-n-hexane) NMR$^{(43)}$ |
| 73 | H | 1 | CH$_2$ | CH$_2$C≡CH | 4-CH$_3$ | 1 | s | NMR$^{(44)}$ |
| 74 | H | 1 | CH$_2$ | C$_2$H$_5$ | 3-CH$_3$ | 1 | s | 134–135 Colorless needle crystals (ethyl acetate-n-hexane) |
| 75 | 5-F, 6-OCH$_3$ | 2 | CH$_2$ | C$_2$H$_5$ | 3-CH$_3$ | 1 | s | NMR$^{(45)}$ |
| 76 | 5-CH$_3$ | 1 | CH$_2$ | CH$_3$ | 4-CH$_3$ | 1 | d | NMR$^{(46)}$ |
| 77 | 5-OCH$_3$ | 1 | CH$_2$ | CH$_3$ | 4-CH$_3$ | 1 | d | NMR$^{(47)}$ |
| 78 | 5-F, OCH$_3$ | 2 | CH$_2$ | CH$_3$ | 4-CH$_3$ | 1 | d | NMR$^{(48)}$ |
| 79 | H | 1 | CH$_2$ | C$_2$H$_5$ | 4-CH$_3$ | 1 | d | NMR$^{(49)}$ |
| 80 | 5-F | 2 | CH$_2$ | C$_2$H$_5$ | 4-CH$_3$ | 1 | d | NMR$^{(50)}$ |
| 81 | 6-OCH$_3$ | 1 | CH$_2$ | CH$_3$ | 3-CH$_3$, 4-CH$_3$ | 2 | d | NMR$^{(51)}$ |
| 82 | H | 1 | CH$_2$ | CH$_2$CH$_2$N(CH$_3$)(CH$_3$) | H | 1 | s | 152–154 White powder (diethyl ether) |
| 83 | H | 1 | CH$_2$ | CH$_3$ | 4=O | 1 | s | 135–136 Yellow powder (ethyl acetate-n-hexane) |
| 84 | H | 1 | CH$_2$ | CH$_3$ | 4-OH | 1 | s | 144.5–145 White powder (ethyl acetate-n-hexane) |
| 85 | H | 1 | CH$_2$ | CH$_3$ | 4-OH, 4-CH$_3$ | 2 | s | 156–157 Yellow powder (dichloromethane-diethyl ether) |
| 86 | H | 1 | CH$_2$ | CH$_3$ | 4-OH, 4-C$_2$H$_5$ | 2 | s | NMR$^{(52)}$ |
| 87 | H | 1 | CH$_2$ | C$_2$H$_5$ | 4-OH, 4-OCH$_3$ | 1 | s | 136–137 Pale yellow powder (ethyl acetate-n-hexane) |
| 88 | H | 1 | CH$_2$ | C$_2$H$_5$ | 4-C$_6$H$_5$ | 1 | s | 162–163 White powder (dichloromethane-diethyl ether) |
| 89 | 5-CH$_3$ | 1 | CH$_2$ | C$_2$H$_5$ | 4-C$_6$H$_5$ | 1 | s | 157.5–158.5 White powder (dichloromethane-diethyl ether) |
| 90 | 5-F, 6-OCH$_3$ | 2 | CH$_2$ | C$_2$H$_5$ | 4-C$_6$H$_5$ | 1 | s | 158–159 White powder (dichloromethane-diethyl ether) |

-continued

| | | | | | | | |
|---|---|---|---|---|---|---|---|
| 91 | H | 1 | CH₂ | C₂H₅ | 4-OCH₃ | s | Pale yellow powder (ethyl acetate-n-hexane) | 136-137 |
| 92 | 5-CH₃ | 1 | CH₂ | C₂H₅ | 4-OCH₃ | s | NMR⁽⁵³⁾ | |
| 93 | 5-OCH₃ | 1 | CH₂ | C₂H₅ | 4-OCH₃ | s | NMR⁽⁵⁴⁾ | |
| 94 | 5-F | 2 | CH₂ | C₂H₅ | 4-OCH₃ | s | NMR⁽⁵⁵⁾ | |
| 95 | 6-OCH₃ 5-OC₂H₅ | 2 | CH₂ | C₂H₅ | 4-OCH₃ | s | NMR⁽⁵⁶⁾ | |
| 96 | 6-F 5-COCH₃ | 1 | CH₂ | C₂H₅ | 4-OCH₃ | s | NMR⁽⁵⁷⁾ | 150-151.5 |
| 97 | H | 1 | CH₂ | C₂H₅ | 4-N(CH₃)₂ | s | Yellow powder (dichloromethane-diethyl ether) | |
| 98 | 5-F 6-OCH₃ | 2 | CH₂ | C₂H₅ | 4-N(CH₃)₂ | s | NMR⁽⁵⁸⁾ | 144-145 |
| 99 | H | 1 | CH₂ | C₂H₅ | 4-NHCH₃ | s | Yellow powder (ethyl acetate) | 201-202 |
| 100 | H | 1 | CH₂ | C₂H₅ | 4=NOH | s | Colorless columns (methanol) | 148-149 |
| 101 | H | 1 | CH₂ | C₂H₅ | 4-OCH₂CH=CH₂ | s | NMR⁽⁵⁹⁾ | |
| 102 | H | 1 | CH₂ | C₂H₅ | 4=CH₂ | s | White powder (dichloromethane-diethyl ether) | 193-194 |
| 103 | H | 1 | CH₂ | C₂H₅ | 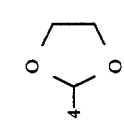 | s | White powder (methanol) | 137-139 |
| 104 | H | 1 | CH₂ | C₂H₅ | 3-CO₂CH₃ | s | White powder (ethyl acetate-n-hexane) | 175-177 |
| 105 | H | 1 | CH₂ | C₂H₅ | 3-CH₂OH | s | White powder (ethanol) | 111-113 |
| 106 | H | 1 | CH₂ | C₂H₅ | 3-CON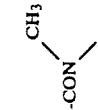 | s | White powder (ethyl acetate-n-hexane) | |
| 107 | H | 1 | CH₂ | C₂H₅ | 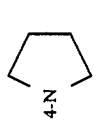 | s | NMR⁽⁶⁰⁾ | 169-171 |
| 108 | 5-OCH₃ | 1 | CH₂ | C₂H₅ | 3-CO₂CH₃ | s | NMR⁽⁶¹⁾ | |
| 109 | 5-OCH₃ | 1 | CH₂ | C₂H₅ | 3-CH₂OH | s | White Powder (ethyl acetate-n-hexane) | |
| 110 | 5-CH₃ | 1 | CH₂ | C₂H₅ | 4-OCH₂CH=CH₂ | s | NMR⁽⁶²⁾ | |
| 111 | 5-COCH₃ | 1 | CH₂ | C₂H₅ | 4-OCH₂CH=CH₂ | s | NMR⁽⁶³⁾ | 128-130 (decomposition) |
| 112 | H | 1 | CH₂ | C₂H₅ | 4=O | s | Yellow powder (dichloromethane-diethyl ether) | |

-continued

| No. | Sub1 | | | | Sub2 | | | Property |
|---|---|---|---|---|---|---|---|---|
| 113 | H | 1 | CH$_2$ | C$_2$H$_5$ | 4-OH | 1 | s | NMR(64) |
| 114 | 5-F | 2 | CH$_2$ | C$_2$H$_5$ | 3-CH$_2$OH | 1 | s | NMR(65) |
| 115 | 6-OCH$_3$ 5-CH$_3$ | 1 | CH$_2$ | C$_2$H$_5$ | 3-CH$_2$OH | 1 | s | NMR(66) |
| 116 | 5-C(=O)CH$_3$ | 1 | CH$_2$ | CH$_2$CH=CH$_2$ | 4-OCH$_3$ | 1 | s | NMR(67) |
| 117 | H | 1 | CH$_2$ | C$_2$H$_5$ | 3,3-diCH$_3$ 4=O | 3 | s | NMR(68) |
| 118 | 5-F 6-OCH$_3$ | 2 | CH$_2$ | CH$_2$CH=CH$_2$ | 4-N(CH$_3$)$_2$ | 1 | s | White powder (ethyl acetate-n-hexane) 144–145 |
| 119 | H | 1 | CH$_2$ | CH$_2$CH=CH$_2$ | 4-N(CH$_3$)$_2$ | 1 | s | Pale yellow powder (ethyl acetate-n-hexane) 131–132 |
| 120 | H | 1 | CH$_2$ | C$_2$H$_5$ | 4=NCH$_3$ | 1 | s | NMR(69) |
| 121 | H | 1 | CH$_2$ | C$_2$H$_5$ | 4-N(CH$_3$)(CH$_2$CH$_2$OH) | 1 | s | NMR(70) |
| 122 | H | 1 | CH$_2$ | C$_2$H$_5$ | 4-N(CH$_3$)(COCH$_3$) | 1 | s | NMR(71) |
| 123 | 5-F 6-OCH$_3$ | 2 | CH$_2$ | C$_2$H$_5$ | 4-N(CH$_3$)(cyclopropyl) | 1 | s | NMR(72) |
| 124 | 5-F 6-OCH$_3$ | 2 | CH$_2$ | H | 4-N(CH$_3$)(CH$_2$CH=CH$_2$) | 1 | s | NMR(73) |
| 125 | 5-F 6-OCH$_3$ | 2 | CH$_2$ | C$_2$H$_5$ | 4-N(CH$_3$)(CH$_2$-cyclopropyl) | 1 | s | NMR(74) |

| No. | Sub | | | | Structure | | Form / mp |
|---|---|---|---|---|---|---|---|
| 126 | 5-F 6-OCH₃ | 2 | CH₂ | C₂H₅ | 4-N(CH₃)-CH(OC₂H₅)(CF₃) | s | NMR⁽⁷⁵⁾ |
| 127 | 5-F 6-OCH₃ | 2 | CH₂ | C₂H₅ | 4-N-pyrrolidine | s | NMR⁽⁷⁶⁾ |
| 128 | 5-F 6-OCH₃ | 2 | CH₂ | C₂H₅ | 4-N(CH₃)-CO-cyclopropyl | s | NMR⁽⁷⁷⁾ |
| 129 | 5-F 6-OCH₃ | 2 | CH₂ | C₂H₅ | 4-N(CH₂CH=CH₂)(COCH₃) | s | NMR⁽⁷⁸⁾ |
| 130 | 5-F 6-OCH₃ | 2 | CH₂ | C₂H₅ | 4-N(CH₂CH=CH₂)(CH₂-C₆H₄-4-OCH₃) | s | NMR⁽⁷⁹⁾ |
| 131 | 5-F 6-OCH₃ | 2 | CH₂ | C₂H₅ | 4-N(CH₂CH=CH₂)(C₂H₅) | s | Colorless needles (ethyl acetate-n-hexane) 146–147 |
| 132 | H | 1 | CH₂ | C₂H₅ | 3-CH₂N(CH₃)(CH₃) | s | White powder (ethyl acetatne-n-hexane) 152–154 |
| 133 | H | 1 | CH₂ | C₂H₅ | 3-CO₂H | s | White powder (ethanol) 181.5–182.5 (decomposition) |

-continued

| | | | | | | |
|---|---|---|---|---|---|---|
| 134 | H | 1 | CH₂ | C₂H₅ | 3-CON(morpholine) | 1 | White powder (ethyl acetate-ethanol) 193.5-194.5 |
| 135 | 5-F 6-OCH₃ | 2 | CH₂ | C₂H₅ | 3-CO₂CH₃ | 1 | s NMR(80) |
| 136 | 5-F 6-OCH₃ | 2 | CH₂ | C₂H₅ | 3-CO₂H | 1 | s NMR(81) |
| 137 | 5-F 6-OCH₃ | 2 | CH₂ | C₂H₅ | 3-CON(pyrrolidine) | 1 | s NMR(82) |
| 138 | 5-F 6-OCH₃ | 2 | CH₂ | C₂H₅ | 3-CNH(CH₂)₂-(3,4-dimethoxyphenyl) | 1 | s NMR(83) |
| 139 | H | 1 | CH₂ | C₂H₅ | 3-CON(piperidine) | 1 | s NMR(84) |
| 140 | 5-CH₃ | 1 | CH₂ | C₂H₅ | 4-N(CH₃)(CH₂CH=CH₂) | 1 | s White powder (½ hydrate) (diethyl ether) 132—133 |
| 141 | 5-COCH₃ | 1 | CH₂ | C₂H₅ | 4-N(CH₃)(CH₂CH=CH₂) | 1 | s NMR(85) |
| 142 | 5-F 6-OCH₃ | 2 | CH₂ | C₂H₅ | 4-N(CH₃)(CH₂CH=CH₂) | 1 | s NMR(86) |
| 143 | 5-CH₃ | 1 | CH₂ | C₂H₅ | 4-NH(cyclohexyl) | 1 | s NMR(87) |

| No. | | | | | | | |
|---|---|---|---|---|---|---|---|
| 144 | 5-F<br>OCH₃ | 2 | CH₂ | CH₂CH=CH₂ | 4-OCH₃ | s | NMR⁽⁸⁸⁾ |
| 145 | 5-CH₃ | 1 | CH₂ | CH₂CH=CH₂ | 4-OCH₃ | s | NMR⁽⁸⁹⁾ |
| 146 | 5-COCH₃ | 1 | CH₂ | C₂H₅ | 4-OCH₂OCH₃ | s | NMR⁽⁹⁰⁾ |
| 147 | 5-F<br>6-OCH₃ | 2 | CH₂ | C₂H₅ | 4-CH₂OH | s | NMR⁽⁹¹⁾ |
| 148 | 5-COCH₃ | 1 | CH₂ | C₂H₅ | 4-N(CH₃)(cyclopropyl) | s | Yellow powder<br>(½ hydrate)<br>(ethyl acetate-n-hexane)<br>167.5–168.5 |
| 149 | 5-F<br>6-OCH₃ | 2 | CH₂ | C₂H₅ | 4-N(CHO)(cyclopropyl) | s | NMR⁽⁹²⁾ |
| 150 | 5-F<br>6-OCH₃ | 2 | CH₂ | C₂H₅ | 4-N(CH₃)(COCF₃) | s | NMR⁽⁹³⁾ |
| 151 | 5-F<br>6-OCH₃ | 2 | CH₂ | C₂H₅ | 4-N(cyclohexyl)(CH₃) | s | NMR⁽⁹⁴⁾ |
| 152 | H | 1 | CH₂ | C₂H₅ | 4-CF₃ | d | NMR⁽⁹⁵⁾ |
| 153 | 5-F<br>6-OCH₃ | 2 | CH₂ | C₂H₅ | 4-CH₂OCH₃ | s | NMR⁽⁹⁶⁾ |
| 154 | 5-CH₃ | 1 | CH₂ | C₂H₅ | 4-OCH₃<br>3,3-diCH₃ | 3 | NMR⁽⁹⁷⁾ |
| 155 | 5-CO-cyclopropyl | 1 | CH₂ | CH₂CH=CH₂ | 4-N(CH₃)₂ | s | NMR⁽⁹⁸⁾ |
| 156 | 5-COCH₃ | 1 | CH₂ | CH₂CH=CH₂ | 4-N(CH₃)₂ | s | NMR⁽⁹⁹⁾ |

⁽¹⁾NMR(CDCl₃)δ: 1.30(3H, t, J=7.5Hz), 1.66–2.10(2H, m), 2.08(3H, s), 2.73(2H, t, J=7Hz), 2.97(2H, q, J=7.5Hz), 3.10–3.34(2H, m), 4.25(2H, s), 6.80–7.50(6H, m)
⁽²⁾NMR(CDCl₃)δ: 1.42(3H, t, J=7.5Hz), 2.83(2H, t, J=7Hz), 3.08(2H, q, J=7.5Hz), 3.23–3.50(2H, m), 3.83(3H, s), 4.27(2H, s), 6.66–7.50(6H, m)

-continued (3) NMR(CDCl₃)δ: 1.42(3H, t, J=7.5Hz), 1.83–2.30(2H, m), 2.50–3.00(2H, m), 3.10(2H, q, J=7.5Hz), 3.23–3.43(2H, m), 4.25(2H, s), 6.67–7.60(5H, m), 13.17(1H, br.)
(4) NMR(CDCl₃)δ: 1.33(3H, t, J=7.5Hz), 1.66–2.10(2H, m), 2.77(2H, t, J=7Hz), 3.00–3.33(2H, m), 3.83(3H, s), 6.66–7.40(5H, m), 13.00(1H, br.)
(5) NMR(CDCl₃)δ: 1.40(3H, t, J=7Hz), 1.43(3H, t, J=7Hz), 3.07(2H, t, J=7Hz), 3.20–3.50(2H, m), 4.26(2H, s), 6.50–7.50(5H, m)
(6) NMR(CDCl₃)δ: 1.38(3H, t, J=7.5Hz), 1.66–2.10(2H, m), 2.50–3.00(2H, m), 3.05(2H, q, J=7.5 Hz), 3.10–3.40(2H, m), 4.25(2H, s), 6.67–7.63(6H, m), 12.17(1H, br.)
(7) NMR(CDCl₃)δ: 1.40(3H, t, J=7.5Hz), 1.66–2.10(2H, m), 1.70–2.20(2H, m), 2.83(3H, s), 2.83(2H, t, J=7.5Hz), 3.07(2H, t, J=7Hz), 3.10–3.20(2H, m), 4.30(2H, s), 6.80–7.20(6H, m)
(8) NMR(CDCl₃)δ: 1.40(3H, t, J=7.5Hz), 1.66–2.20(2H, m), 2.80(2H, t, J=6Hz), 3.03(2H, q, J=7Hz), 3.20–3.50(2H, m), 4.28(2H, s), 6.70–7.50(6H, m)
(9) NMR(CDCl₃)δ: 1.35(3H, t, J=7.5Hz), 1.66–2.20(2H, m), 2.55(3H, s), 2.77(2H, t, J=6Hz), 3.03(2H, q, J=7Hz), 3.20–3.50(2H, m), 3.00–3.20(2H, m), 6.67–7.50(6H, m), 12.80(1H, br.)
(10) NMR(CDCl₃)δ: 1.37(3H, t, J=7.5Hz), 1.67–2.10(2H, m), 2.40(3H, s), 2.50(2H, s), 2.80(2H, t, J=7.5Hz), 3.03(2H, q, J=7.5Hz), 3.10–3.50(2H, m), 4.23(2H, s), 6.70–7.43(5H, m), 12.50(1H, br.)
(11) NMR(CDCl₃)δ: 1.70–2.30(2H, m), 2.83(2H, t, J=7Hz), 2.90(3H, s), 3.20–3.40(2H, m), 4.36(2H, m), 6.80–7.80(6H, m), 13.10(1H, br.)
(12) NMR(CDCl₃)δ: 1.50–2.10(2H, m), 2.53(3H, s), 2.30–2.80(2H, m), 2.73(3H, s), 2.83–3.30(2H, m), 4.30(2H, s), 6.70–7.33(6H, m)
(13) NMR(CDCl₃)δ: 1.73–2.13(2H, m), 2.80(2H, t, J=6Hz), 2.83(3H, s), 3.10–3.33(2H, m), 3.83(3H, s), 4.33(2H, s), 6.80–7.33(5H, m), 11.50 (1H, br.)
(14) NMR(CDCl₃)δ: 1.67–2.07(2H, m), 2.60–2.92(2H, m), 3.07–3.37(2H, m), 3.57(2H, d, J=6Hz), 4.33(2H, s), 5.07–6.33(1H, m), 5.77–6.33(1H, m), 6.80–7.33(5H, m)
(15) NMR(CDCl₃)δ: 1.73–2.10(2H, m), 2.83(2H, t, J=8Hz), 3.13–3.40(2H, m), 3.60(2H, s), 3.80(3H, s), 4.30(2H, s), 5.17–5.57(2H, m), 5.77–6.40(1H, m), 6.57–7.50(6H, m)
(16) NMR(CDCl₃)δ: 1.70–2.13(2H, m), 2.82(2H, t, J=7Hz), 3.13–3.43(2H, m), 3.63(2H, s), 4.30(2H, s), 5.20–5.60(2H, m), 5.83–6.43(1H, m), 6.70–7.67(6H, m)
(17) NMR(CDCl₃)δ: 0.95(3H, t, J=6Hz), 1.13–1.63(4H, m), 2.67–3.18(4H, m), 3.18–3.50(2H, m), 4.30(2H, s), 6.80–7.83(7H, m)
(18) NMR(CDCl₃)δ: 0.93(3H, t, J=7Hz), 1.13–1.60(2H, m), 1.63–2.17(4H, m), 2.43(3H, s), 2.63–3.13(4H, m), 3.13–3.43(2H, m), 4.30(2H, s), 6.87–7.67(6H, m)
(19) NMR(CDCl₃)δ: 0.93(3H, t, J=7Hz), 1.13–1.60(2H, m), 1.60–2.13(4H, m), 2.63–3.13(4H, m), 3.80(3H, s), 4.30(2H, s), 6.63–7.47(6H, m)
(20) NMR(CDCl₃)δ: 1.23(3H, t, J=8Hz), 1.40–2.23(2H, m), 2.67–3.33(4H, m), 2.82(3H, s), 4.33(2H, s), 6.90–7.57(7H, m)
(21) NMR(CDCl₃)δ: 1.27(3H, t, J=8Hz), 1.47–2.33(2H, m), 2.70–3.37(7H, m), 2.88(3H, s), 3.87(3H, s), 4.33(2H, s), 6.87–7.37(5H, m)
(22) NMR(CDCl₃)δ: 1.33(3H, t, J=8Hz), 1.67–2.07(2H, m), 2.77(2H, t, J=8Hz), 3.00(2H, q, J=8Hz), 3.13–3.37(2H, m), 4.22(2H, s), 6.93–7.60(6H, m)
(23) NMR(CDCl₃)δ: 1.66–2.17(2H, m), 2.40(3H, s), 2.50(3H, s), 2.87(2H, t, J=7Hz), 2.87(3H, s), 3.16–3.43(2H, m), 4.30(2H, s), 6.66–7.37(5H, m)
(24) NMR(CDCl₃)δ: 1.70–2.30(2H, m), 2.63(3H, s), 2.87(2H, t, J=8Hz), 2.95(3H, s), 3.20–3.47(2H, m), 4.35(2H, s), 6.80–7.90(5H, m), 8.07(1H, s)
(25) NMR(CDCl₃)δ: 1.37(3H, t, J=8Hz), 1.67–2.07(2H, m), 2.60–3.37(6H, m), 3.87(3H, s), 4.23(2H, s), 6.90–7.47(4H, m)
(26) NMR(CDCl₃)δ: 1.33(3H, t, J=8Hz), 1.67–2.07(2H, m), 2.75(2H, t, J=8Hz), 2.97(2H, q, J=8Hz), 3.10–3.37(2H, m), 3.67(3H, s), 3.83(3H, s), 4.23(2H, s), 6.45(1H, d, J=3Hz), 6.78(1H, d, J=3Hz), 6.87–7.40(2H, m)
(27) NMR(CDCl₃)δ: 1.70–2.20(2H, m), 2.60–3.00(2H, m), 2.93(3H, s), 3.20–3.40(2H, m), 3.92(3H, s), 4.32(2H, s), 6.80–8.30(6H, m), 12.30(1H, brs)
(28) NMR(CDCl₃)δ: 1.42(3H, t, J=7.5Hz), 1.80–2.20(2H, m), 2.82(2H, t, J=7Hz), 2.88(3H, s), 3.17–3.40(2H, m), 4.07(2H, s), 4.32(2H, s), 5.30–5.50(2H, m), 6.00–6.20(1H, m), 6.90–7.50(4H, m), 7.81(1H, dd), 8.06(1H, s)
(29) NMR(CDCl₃)δ: 1.33(3H, t, J=7Hz), 1.66–2.10(2H, m), 2.30(3H, d, J=2Hz), 2.77(2H, t, J=7Hz), 2.98(2H, q, J=7Hz), 3.10–3.40(2H, m), 4.27(2H, s), 6.73–7.50(5H, m), 12.97(1H, br.)
(30) NMR(CDCl₃)δ: 1.70–2.00(2H, m), 2.66(2H, t, J=7.5Hz), 3.07–3.20(2H, m), 3.45(2H, t, J=7Hz), 3.69(3H, s), 4.08(2H, s), 5.10–5.30(2H, m), 5.80–6.00(1H, m), 6.70–7.15(5H, m)
(31) NMR(CDCl₃)δ: 1.70–2.10(2H, m), 2.57(3H, s), 2.57(3H, s), 3.07–3.45(2H, m), 3.20–3.45(2H, m), 3.61(2H, d, J=7Hz), 4.34(2H, s), 5.20–5.50(2H, m), 5.95–6.25(1H, m), 6.90–7.40(6H, m), 12.61(1H, br.)
(32) NMR(CDCl₃)δ: 1.90–2.15(2H, m), 2.49(3H, s), 2.61(3H, s), 2.80–3.00(2H, m), 3.30–3.50(2H, m), 3.72(2H, d, J=7Hz), 4.35(2H, s), 5.40–5.60(2H, m), 5.83–6.43(1H, m), 6.85–7.45(5H, m), 12.27(1H, br.)
(33) NMR(CDCl₃)δ: 1.43(3H, t), 1.70–2.10(2H, m), 2.80(2H, t), 3.10–3.30(2H, m), 3.59(2H, d), 4.06(2H, q), 4.34(2H, s), 5.10–5.50(2H, m), 5.90–6.20(1H, m), 6.70–7.40(5H, m)
(34) NMR(CDCl₃)δ: 1.60–2.10(2H, m), 2.73(2H, t), 3.05–3.35(2H, m), 3.53(2H, d), 4.30(2H, s), 5.80–6.30(1H, m), 5.10–5.60(2H, m), 6.80–6.30(6H, m), 12.30(1H, brs)
(35) NMR(CDCl₃)δ: 1.42(3H, t), 1.90–2.10(2H, m), 2.64(3H, s), 2.85(2H, t), 3.30–3.40(2H, m), 3.66(2H, m), 4.32(2H, s), 5.30–5.50(2H, m), 6.00–6.20(1H, m), 6.90–7.50(4H, m), 7.81(1H, dd), 8.06(1H, s)
(36) NMR(CDCl₃)δ: 1.92–2.13(2H, m), 2.39(1H, t, J=8Hz), 2.85(2H, t, J=8Hz), 3.48(2H, t, J=2Hz), 3.82 and 3.85(3H, s), 3.88 and 3.91(3H, s), 4.34 and 4.35(2H, s), 6.86–7.42(5H, m)
(37) NMR(CDCl₃)δ: 1.93–3.12(2H, m), 2.39(1H, t, J=2Hz), 2.85(2H, t, J=7Hz), 3.40–3.57(2H, m), 3.79(2H, d, J=2Hz), 3.88 and 3.91(3H, s), 4.34 and 4.35(2H, s), 6.86–7.42(5H, m)
(38) NMR(CDCl₃)δ: 1.27(3H, d), 1.40–2.30(2H, m), 2.95(1H, q), 3.20–3.40(2H, m), 4.30(2H, s), 5.80–6.40(1H, m), 6.70–7.70(7H, m)
(39) NMR(CDCl₃)δ: 0.27–0.38(2H, m), 0.63–0.75(2H, m), 1.08–1.33(1H, m), 1.92–2.10(2H, m), 2.85(2H, t, J=7Hz), 2.95(2H, d, J=7Hz), 3.52–3.64(2H, m), 4.32(2H, s), 6.90–7.67(7H, m)
(40) NMR(CDCl₃)δ: 0.29–0.45(2H, m), 0.64–0.80(2H, m), 1.13–1.35(1H, m), 1.92–2.13(2H, m), 2.84–3.09(1H, m), 3.37–3.67(2H, m), 3.81(2H, d, J=2Hz), 4.36(2H, s), 4.29 and 4.30(2H, s), 6.85–7.40(5H, m)
(41) NMR(CDCl₃)δ: 1.70–2.10(2H, m), 2.80–3.40(5H, m), 2.85(3H, s), 4.27(2H, s), 6.60–7.40(5H, m)
(42) NMR(CDCl₃)δ: 1.27(3H, d), 1.37(3H, t), 1.50–2.20(2H, m), 2.60(3H, s), 2.70–3.50(5H, m), 4.30(2H, s), 6.80–7.60(4H, m), 7.79(1H, dd), 8.07(1H, m)
(43) NMR(CDCl₃)δ: 1.23(3H, d), 1.37(3H, t), 1.50–2.50(2H, m), 2.82(3H, s), 2.70–3.40(5H, m), 4.30(2H, s), 6.80–7.60(4H, m), 5.90–6.20(1H, m), 6.70–7.40(5H, m)
(44) NMR(CDCl₃)δ: 1.09(3H, d), 2.20–2.50(2H, m), 2.50–2.70(1H, m), 3.77(3H, s), 4.30(2H, s), 3.60–3.70(2H, m), 2.84–3.09(1H, m), 2.05–2.24(1H, m), 3.37–3.67(2H, m), 5.20–5.60(2H, m), 3.81(2H, d, J=2Hz), 4.36(2H, s), 7.04–7.68(7H, m)
(45) NMR(CDCl₃)δ: 1.29(3H, d, J=6Hz), 1.64–1.85(1H, m), 2.05–2.24(1H, m), 2.30(1H, t, J=2Hz), 2.84–3.09(1H, m), 3.37–3.67(2H, m), 3.81(2H, d, J=2Hz), 4.36(2H, s), 7.04–7.68(7H, m)
(46) NMR(CDCl₃)δ: 1.07(3H, d), 1.36(3H, t), 2.00–3.50(7H, m), 3.86(3H, s), 4.38(2H, s), 6.60–7.30(5H, m)
(47) NMR(CDCl₃)δ: 2.07(3H, d), 2.40(3H, s), 2.72(3H, s), 3.70–3.90(2H, m), 4.30(2H, s), 5.60–5.80(1H, m), 6.70–7.50(6H, m)
(48) NMR(CDCl₃)δ: 2.05(3H, d), 2.67(3H, s), 2.69(3H, s), 3.60–3.90(2H, m), 3.77(3H, s), 4.30(2H, s), 5.60–5.80(1H, m), 6.70–7.50(6H, m)
(49) NMR(CDCl₃)δ: 2.06(3H, d), 2.69(3H, s), 3.50–3.80(2H, m), 3.83(3H, s), 4.33(2H, s), 5.50–5.70(1H, m), 6.70–7.50(6H, m), 12.60–13.00(1H, brs)
(50) NMR(CDCl₃)δ: 1.22(3H, d), 2.06(3H, d), 2.95(3H, s), 3.60–3.80(2H, m), 3.83(3H, m), 4.32(2H, s), 5.50–5.80(1H, m), 6.90–7.50(5H, m)
(51) NMR(CDCl₃)δ: 1.88(3H, s), 1.98(3H, s), 2.60(3H, s), 3.53(2H, s), 4.29(2H, s), 6.90–7.70(7H, m)
(52) NMR(CDCl₃)δ: 0.88(3H, t), 1.78–2.14(2H, m), 2.96(3H, s), 3.28–3.72(2H, m), 4.10(1H, d, J=15Hz), 4.56(1H, d, J=15Hz), 7.10–7.57(7H, m)
(55) NMR(CDCl₃)δ: 4.17(1H, br), 4.45(1H, brs), 6.7–7.56(H, m), 12.23(1H, brs)
(55) NMR(CDCl₃)δ: 1.41(3H, t, J=7Hz), 2.05–2.20(2H, m), 2.98–3.27(2H, m), 3.33–3.48(2H, m), 3.44(3H, s), 3.89(3H, brs), 4.23–4.34(3H, m), 6.79–7.33(4H, m)7.42(1H, dd, J=2.8Hz)
(56) NMR(CDCl₃)δ: 1.29(3H, t, J=7.0Hz), 1.44(3H, t, J=6.9Hz), 2.0–2.2(2H, m), 2.9–3.3(2H, m), 3.2–3.3(2H, m), 3.42(3H, s), 4.09(2H, q, J=6.9Hz), 4.1–4.3(1H, m), 4.46(2H, s), 6.8–7.4(5H, m)
3.74 and 3.77(3H), 4.17(1H, brs), 4.45(1H, brs), 6.7–7.56(H, m), 12.23(1H, brs)
3.16(2H, brs), 3.35 and 3.37(3H), -continued (57)NMR(CDCl₃)δ: 1.33(3H, t, J=7.0Hz), 2.0-2.1(2H, m), 2.60(3H, s), 2.9-3.2(2H, m), 3.3-3.4(2H, m), 3.39(3H, s), 4.23(1H, t, J=4.2Hz), 4.39(2H, d, J=5.3Hz), 6.9-7.7(6H, m)
(58)NMR(CDCl₃)δ: 1.41(3H, t, J=7Hz), 1.65-1.93(1H, m), 2.06-2.38(1H, m), 2.26(6H, s), 2.88-3.12(1H, m), 3.40-3.61(1H, m), 3.80(1H, t, J=7Hz), 3.89(3H, brs), 4.09(1H, d, J=15Hz), 4.39(1H, d, J=15Hz), 6.80-7.23(3H, m), 7.36(1H, d, J=7Hz), 7.52(1H, d, J=8Hz)
(59)NMR(CDCl₃)δ: 1.38(3H, t, J=7.5Hz), 2.04-2.12(2H, m), 3.04(2H, q, J=7.5Hz), 3.40-3.45(2H, m), 4.00-4.20(2H, m), 4.29(2H, s), 4.43(1H, t, J=0.6Hz), 5.15-5.35(2H, m), 5.85-6.00(1H, m), 7.00-7.60(7H, m), 12.54(1H, brs)
(60)NMR(CDCl₃)δ: 1.40(3H, t, J=7Hz), 1.63-1.88(5H, m), 2.10-2.22(1H, m), 2.35-2.53(2H, m), 2.53-2.72(2H, m), 2.98-3.33(2H, m), 3.40-3.56(2H, m), 3.61(1H, t, J=5Hz), 4.10(1H, d, J=15Hz), 4.44(1H, d, J=15Hz), 7.00(1H, t, J=7Hz), 7.05-7.21(2H, m), 7.21-7.45(3H, m), 7.53-7.65(3H, m)
(61)NMR(CDCl₃)δ: 1.40(3H, t, J=7Hz), 2.95-3.06(2H, m), 3.80(3H, s), 3.70-3.82(5H, m), 4.18(1H, d, J=14Hz), 4.51(1H, d, J=14Hz), 6.62-6.78(2H, m), 7.00(2H, d, J=4Hz), 7.14-7.47(3H, m), 7.53-7.65(1H, m)
(62)NMR(CDCl₃)δ: 1.41(3H, t, J=8Hz), 2.05-2.30(2H, m), 2.44 and 2.42(3H), 3.10(2H, q, J=8Hz), 2.44(2H, d, J=0.5Hz), 4.00-4.60(2H, m), 4.27(3H, s), 5.10-5.40(2H, m), 5.60-6.10(1H, m), 7.00-7.50(6H, m), 12.12(1H, brd)
(63)NMR(CDCl₃)δ: 1.45(3H, t, J=7.5Hz), 2.05-2.20(2H, m), 2.65(3H, s), 3.13(2H, q, J=7.5Hz), 3.49(2H, bs), 4.00-4.30(2H, m), 4.30(2H, s), 4.46(1H, t, J=0.5Hz), 5.10-5.35(2H, m), 5.85-6.05(1H, m), 7.13(1H, t, J=8Hz), 7.25(1H, dd, J=0.25Hz), 7.50-8.20(3H, m), 13.00(1H, brd)
(64)NMR(CDCl₃)δ: 1.40(3H, t, J=7.2Hz), 1.9-2.3(2H, m), 2.9-3.2(2H, m), 3.3-3.5(2H, m), 4.12 and 4.33 (2H, dd, J=14.9Hz), 7.0-7.5(7H, m), 12.1-12.8(1H, brs)
(65)NMR(CDCl₃)δ: 1.39(3H, t, J=7Hz), 2.39(3H, s), 2.00-3.90(9H, m), 3.98(1H, d, J=15Hz), 4.45(1H, d, J=15Hz), 6.55-7.27(6H, m)
(66)NMR(CDCl₃)δ: 1.41(3H, t, J=7Hz), 1.70-4.00(9H, m), 3.78(3H, s), 4.04(1H, d, J=15Hz), 4.46(1H, d, J=15Hz), 6.80-7.40(5H, m)
(67)NMR(CDCl₃)δ: 1.9-2.1(2H, m), 2.59(3H, s), 3.2-3.3(2H, m), 3.40(3H, s), 3.59(2H, d, J=5.5Hz), 4.23(1H, t, J=4.3Hz), 4.40 and 4.49(2H, dd, J=14Hz), 5.22(1H, d, J=10.3Hz), 5.36(1H, d, J=16.9Hz), 5.6-6.1(1H, m), 6.98(1H, t, J=7.6Hz), 7.21(1H, d, J=7.0Hz), 7.36(1H, d, J=6.7Hz), 7.3-7.5(1H, brs), 7.81(1H, d, J=8.5Hz), 8.0-8.2(1H, brs)
(68)NMR(CDCl₃)δ: 1.21(6H, s), 1.35(3H, t, J=7.5Hz), 2.66(3H, s), 3.27(2H, s), 3.53(2H, q, J=7.5Hz), 4.60(2H, s), 6.88(1H, t, J=7.0Hz), 7.2-8.4(5H, m)
(69)NMR(CDCl₃)δ: 1.40(3H, t, J=7Hz), 2.75(2H, t, J=6Hz), 3.09(2H, q, J=7Hz), 3.32(3H, s), 3.55(2H, t, J=6Hz), 4.34(2H, s), 7.05-7.23(3H, m), 7.32(1H, brs), 7.51(1H, dd, J=1.8Hz), 7.60(1H, brs), 8.03(1H, d, J=1.8Hz)
(70)NMR(CDCl₃)δ: 1.42(3H, t, J=7.2Hz), 1.73-1.96(1H, m), 2.10-2.33(1H, m), 2.23(3H, s), 2.67(3H, s), 2.88-3.10(1H, m), 3.10-3.38(1H, m), 3.48-3.70(3H, m), 3.94(1H, t, J=8.0Hz), 4.10(1H, d, J=14.8Hz), 4.43(1H, d, J=14.8Hz), 7.00-7.69(7H, m)
(71)NMR(CDCl₃)δ: 1.29-1.50(3H, m), 1.81-2.43(2H, m), 2.23 and 2.27(3H, s), 2.65 and 2.69(3H, s), 2.85-3.65(4H, m), 4.18 and 4.20(1H, d, J=14.5Hz), 4.44 and 4.50(1H, d, J=14.5Hz), 5.00 and 5.91(1H, t, J=7.6Hz and J=8.3Hz), 6.87-7.22(4H, m), 7.30-7.56(3H, m)
(72)NMR(CDCl₃)δ: 0.30-0.60(4H, m), 1.38(3H, t, J=7Hz), 1.80-2.00(1H, m), 2.00-2.40(2H, m), 2.14(3H, s), 2.80-3.15(1H, m), 3.35-3.60(2H, m), 3.87(3H, s), 3.97(1H, t, J=6.6Hz), 4.15(1H, d, J=14.5Hz), 4.40(1H, d, J=14.5Hz), 4.40(1H, d, J=14.5Hz), 6.80-7.60(5H, m), 12.90(1H, br.)
(73)NMR(CDCl₃)δ: 1.73-1.95(2H, m), 2.20(3H, s), 2.90-3.50(4H, m), 3.77(1H, t, J=6.7Hz), 3.80(3H, s), 4.30(1H, d, J=13.4Hz), 4.41(1H, d, J=13.4Hz), 5.01-5.30(2H, m), 5.71-5.99(1H, m), 6.55(1H, t, J=7.5 Hz), 6.65-7.44(2H, m), 6.92(1H, t, J=6.4Hz), 7.33(1H, d, J=7.3Hz)
(74)NMR(CDCl₃)δ: 0.00-0.20(2H, m), 0.35-0.62(2H, m), 0.76-0.99(1H, m), 1.41(3H, t, J=7.1Hz), 1.66-1.90(1H, m), 2.02-2.47(3H, m), 2.29(3H, s), 2.83-3.09(1H, m), 3.09-3.34(2H, m), 3.34-3.62(1H, m), 3.88(3H, s), 4.02(1H, t, J=6.6Hz), 4.08(1H, d, J=15.0Hz), 4.38(1H, d, J=15Hz), 6.78-7.22(3H, m), 7.34(1H, d, J=7.3Hz), 7.64(1H, d, J=7.9Hz)
(75)NMR(CDCl₃)δ: 1.28 and 1.29(2H, t, J=7.0Hz), 1.40(2H, t, J=7.1Hz), 1.73-2.09 and 2.22-2.48(2H, m), 2.28 and 2.40(3H, s), 2.87-3.11(1H, m), 3.11-3.37(2H, m), 2.87-3.11(1H, m), 3.11-3.37(2H, m), 3.39-3.60(1H, m), 3.60-3.85(2H, m), 3.88(3H, s), 4.03-4.29(2H, m), 4.29-4.50(2H, m), 6.77-7.53(5H, m)
(76)NMR(CDCl₃)δ: 1.41(3H, t, J=6.9Hz), 1.64(4H, brs), 2.20-2.43(1H, m), 2.46-2.73(3H, m), 2.73-3.13(4H, m), 3.18-3.40(2H, m), 3.89(3H, s), 4.11(1H, d, J=14.6Hz), 4.43(1H, d, J=14.6Hz), 4.61(1H, d, J=9.4Hz), 6.72-7.54(5H, m)
(77)NMR(CDCl₃)δ: 0.72-0.91(2H, m), 0.95-1.18(2H, m), 1.18-1.33(1H, m), 1.41(3H, t, J=7.0Hz), 1.66-2.28(2H, m), 2.88(3H, s), 2.92-3.62(4H, m), 3.90(3H, s), 4.16(1H, d, J=14.6Hz), 4.41(1H, d, J=14.6Hz), 5.30(2H, m), 5.91(1H, t, J=8.0Hz), 6.73-7.53(5H, m)
(78)NMR(CDCl₃)δ: 1.30(3H, t, J=6.9Hz), 1.80-2.10(1H, m), 2.10-2.30(1H, m), 2.80-3.60(6H, m), 3.85(3H, s), 4.15-4.55(2H, m), 4.95-5.30(2H, m), 5.70-6.10(2H, m), 6.80-7.50(5H, m), 12.56(1H, br.)
(79)NMR(CDCl₃)δ: 1.34(3H, t, J=7Hz), 1.85-2.00(1H, m), 2.00-2.30(1H, m), 2.80-3.30(5H, m), 3.40-3.65(2H, m), 3.77(3H, s), 3.83(3H, s), 3.85-4.20(2H, m), 4.39(1H, d, J=8.3Hz), 5.00-5.30(2H, m), 5.75-6.00(1H, m), 6.70-7.35(7H, m), 7.52(1H, d, J=7.6Hz), 7.75(1H, d, J=7.6Hz), 12.90(1H, br.)
(80)NMR(CDCl₃)δ: 1.41(3H, t, J=7Hz), 2.60-3.20(5H, m), 3.60-4.00(2H, m), 3.80(3H, s), 3.89(3H, s), 4.15(1H, d, J=14.5Hz), 4.49(1H, d, J=14.5Hz), 6.70-7.40(5H, m), 11.60-12.10(1H, brs)
(81)NMR(CDCl₃)δ: 1.34(3H, t, J=7Hz), 2.70-3.20(5H, m), 3.70-4.20(2H, m), 3.89(3H, s), 4.36(1H, d, J=14Hz), 4.55(1H, d, J=14Hz), 6.70-7.30(5H, m)
(82)NMR(CDCl₃)δ: 1.33(3H, t, J=7Hz), 1.80-2.10(4H, m), 2.80-3.20(5H, m), 3.30-3.70(6H, m), 3.85(3H, s), 4.27(1H, d, J=14Hz), 4.50(1H, d, J=14Hz), 6.80-7.40(5H, m), 12.00-12.50(1H, brs)
(83)NMR(CDCl₃)δ: 1.30(3H, t, J=7Hz), 2.60-3.20(9H, m), 3.40-3.70(2H, m), 3.85(3H, s), 3.86(3H, s), 3.87(3H, s), 4.14(1H, d, J=14Hz), 4.44(1H, d, J=14Hz), 6.70-7.40(8H, m), 11.70-12.20(1H, brs)
(84)NMR(CDCl₃)δ: 1.41(3H, t, J=7.0Hz), 1.40-1.80(6H, m), 2.80-3.30(6H, m), 3.50-3.80(5H, m), 4.14(1H, d, J=14Hz), 4.50(1H, d, J=14Hz), 6.90-7.20(7H, m), 11.80-12.20(1H, brs)
(85)NMR(CDCl₃)δ: 1.40(3H, t, J=7.0Hz), 1.70-1.95(1H, m), 2.05-2.30(1H, m), 2.20(3H, s), 2.67(3H, s), 2.80-3.35(5H, m), 3.45-3.70(1H, m), 3.97(1H, t, J=8.5Hz), 4.27(1H, d, J=14.4Hz), 4.50(1H, d, J=14.4Hz), 5.05-5.35(2H, m), 5.70-6.00(1H, m), 7.00-8.30(6H, m)
(86)NMR(CDCl₃)δ: 1.37(3H, t, J=7.2Hz), 1.70-1.90(1H, m), 2.00-2.25(1H, m), 2.18(3H, s), 2.80-3.40(5H, m), 3.40-3.65(1H, m), 3.80-4.10(1H, m), 3.87(3H, s), 4.13(1H, d, J=14.5Hz), 4.41(1H, d, J=14.5Hz), 5.00-5.40(2H, m), 5.70-6.00(1H, m), 6.70-7.80(5H, m), 12.50-13.00(1H, br.)
(87)NMR(CDCl₃)δ: 0.95-2.20(10H, m), 1.28(3H, t, J=7.0Hz), 2.39(3H, m), 2.55-2.80(1H, m), 3.82(3H, s), 3.40(3H, s), 3.82(3H, s), 5.1-5.5(2H, m), 5.8-6.0(1H, m), 4.20(1H, d, J=14.4Hz), 4.31(1H, d, J=14.4Hz), 6.80-7.50(6H, m)
(88)NMR(CDCl₃)δ: 1.9-2.1(2H, m), 3.1-3.3(2H, m), 3.40(3H, s), 3.42(3H, s), 3.6-3.7(2H, m), 4.3-4.5(2H, m), 4.46(2H, s), 5.2-5.5(2H, m), 5.9-6.2(1H, m), 6.7-7.5(5H, m)
(89)NMR(CDCl₃)δ: 1.9-2.1(2H, m), 2.43(3H, s), 3.1-3.3(2H, m), 3.40(3H, s), 3.42(3H, s), 3.6-3.7(2H, m), 4.26(1H, m), 4.4(2H, s), 5.2-5.5(2H, m), 5.9-6.2(1H, m), 6.9-7.4(6H, m)

-continued (90)NMR(CDCl₃)δ: 1.39(3H, t, J=7Hz), 1.9-2.3(2H, m), 2.62(3H, s), 2.9-3.2(2H, m), 3.42(3H, m), 4.30(1H, d, J=15Hz), 4.44(1H, d, J=15Hz), 4.6-5.0(3H, m), 7.0-8.1(6H, m)
(91)NMR(CDCl₃)δ: 1.34(3H, t, J=7Hz), 1.9-2.2(2H, m), 2.9-3.1(2H, m), 3.5-3.7(1H, m), 3.7-3.9(2H, m), 3.82(3H, s), 4.23(2H, s), 6.8-7.3(5H, m)
(92)NMR(CDCl₃)δ: 0.35-0.80(4H, m), 1.36(3H, t, J=7Hz), 1.80-2.10(1H, m), 2.35-2.70(1H, m), 2.80-3.64(4H, m), 3.87(3H, s), 4.26(1H, d, J=14.4Hz), 4.34(1H, d, J=14.4Hz), 5.54(1H, t, J=8.3Hz), 6.80-7.40(5H, m), 8.45(1H, s), 12.40(1H, br.)
(93)NMR(CDCl₃)δ: 1.43(3H, t, J=7.1Hz), 1.92-2.50(2H, m), 2.75, 2.87 and 2.88(3H, s), 2.96-3.14(1H, m), 3.14-3.40(2H, m), 3.40-3.63(1H, m), 3.91(3H, s), 4.18(1H, d, J=14.5Hz), 4.37-4.55(1H, m), 5.25 and 5.79(1H, t, J=9.0Hz and J=8.2Hz), 6.75-7.52(5H, m)
(94)NMR(CDCl₃)δ: 1.00-1.50(5H, m), 1.36(3H, t, J=7.0Hz), 1.50-2.00(6H, m), 2.11(3H, s), 2.10-2.35(1H, s), 2.40-2.60(1H, m), 2.85-3.10(1H, m), 3.10-3.35(2H, m), 3.35-3.60(1H, m), 3.88(3H, s), 4.05(1H, t, J=7Hz), 4.19(1H, d, J=14.4Hz), 4.44(1H, d, J=14.4Hz), 6.90-7.60(5H, m)
(95)NMR(CDCl₃)δ: 1.26(3H, t, J=7Hz), 2.99(2H, q, J=7Hz), 3.80-4.00(2H, m), 4.41(2H, s), 6.40-6.60(1H, m), 7.00-7.70(7H, m), 11.65(1H, brs)
(96)NMR(CDCl₃)δ: 1.32(3H, t, J=7Hz), 1.6-2.0(2H, m), 2.02(3H, s), 2.9-3.1(2H, m), 3.01-3.2(3H, m), 3.86(3H, s), 4.0-4.4(2H, m), 4.45(2H, s), 6.7-7.4(5H, m)
(97)NMR(CDCl₃)δ: 0.60(3H, s), 1.15(3H, s), 1.27(3H, s), 1.20-1.50(3H, m), 2.44(3H, s), 3.10-3.35(4H, m), 3.30(3H, s), 3.58(1H, s), 4.20(1H, d, J=14.4Hz), 4.50(1H, d, J=14.4Hz), 6.90-7.60(6H, m)
(98)NMR(CDCl₃)δ: 0.90-1.10(2H, m), 1.10-1.30(2H, m), 1.70-1.90(1H, m), 2.10-2.30(1H, m), 2.27(6H, s), 2.60-2.80(1H, m), 3.20-3.40(1H, m), 3.50-3.90(4H, m), 4.10-4.60(2H, m), 5.20-5.60(2H, m), 6.00-6.20(1H, m), 7.10-8.00(6H, m), 12.89(1H, brs)
(99)NMR(CDCl₃)δ: 1.72-1.93(1H, m), 2.09-2.40(1H, m), 2.28(6H, s), 2.64(3H, s), 3.20-3.41(1H, m), 3.44-3.77(3H, m), 3.82(1H, t, J=7.8Hz), 4.15 and 4.19(1H, d, J=14.9Hz), 4.50(1H, d, J=14.9Hz), 5.30-5.55(2H, m), 5.98-6.24(1H, m), 7.11(1H, t, J=7.7Hz), 7.29(0.5H, d, J=9.4Hz), 7.38(1H, d, J=7.3Hz), 7.50-7.66(1.5H, m), 7.73-7.90(1H, m), 7.94 and 8.21(1H, brs)

EXAMPLE 157

2-Mercaptobenzimidazole (0.7 g) was dissolved in dimethyl formamide (30 ml). Sodium hydride (60% in oil, 0.19 g) was added thereto under ice-cooling and the mixture was stirred for 30 minutes. Sequentially, a solution of 1,4-dimethyl-8-chloromethyl-1,2-dihydroquinoline (0.8 g) in dimethyl formamide(5 ml) was added dropwise to the reaction mixture and the mixture was stirred for 1 hour under ice-cooling. After distilling off dimethyl formamide, the resulting residue was poured into an ice-cold water and the mixture was extracted with chloroform. The extract was dried over anhydrous magnesium sulfate, then chloroform was distilled off. The resulting residue was purified by silica gel column chromatography [eluent : dichloromethane-methanol (200:1)] to give 1,4-dimethyl-8-(2-benzimidazolyl)thiomethyl-1,2-dihydroquinoline (0.4 g).

NMR (CDCl$_3$) δ: 2.02 (3H, d, J=1.5 Hz), 2.63 (3H, s), 3.50–3.80 (2H, m), 4.30 (2H, s), 5.50–5.70 (1H, m), 6.90–7.70 (7H, m), 12.87 (1H, brs).

EXAMPLE 158

5-Methoxy-2-chlorobenzimidazole (0.55 g), thiourea (0.2 g) and ethanol (10 ml) were refluxed for 2 hours. To the reaction mixture was added a solution of 1-methyl-8-chloromethyl-1,2,3,4-tetrahydroquinoline hydrochloride (0.51 g) and sodium hydroxide (0.3 g) in water (5 ml) and the mixture was refluxed for 5 hours. After completion of the reaction, ethanol was distilled off and water was added to the resulting residue, and the mixture was extracted with chloroform. After drying over anhydrous magnesium sulfate, chloroform was distilled off. The resulting residue was purified by silica gel column chromatography [eluent:n-hexane-ethyl acetate (4:1)] to give 8-(5-methoxy-2-benzimidazolyl)thiomethyl-1-methyl-1,2,3,4-tetrahydroquinoline (0.62 g).

NMR (CDCl$_3$) δ: 1.60–2.00 (2H, m), 2.70 (2H, t, J=7 Hz), 2.73 (3H, s), 2.83–3.23 (2H, m), 3.73 (3H, s), 4.30 (2H, s), 6.67–7.40 (6H, m), 12.50 (1H, br.).

In a manner analogous to Example 158, the same compounds as those obtained in Examples 2 to 157 were produced using appropriate starting materials.

EXAMPLE 159

8-Carboxythiomethyl-1-methyl-1,2,3,4-tetrahydroquinoline hydrochloride (27.9 g) and 5-methoxy-o-phenylenediamine (13.8 g) in 4N hydrochloric acid (100 ml) were refluxed for 40 minutes. The reaction mixture was cooled, neutralized with aqueous ammonia and extracted with chloroform. After drying the extract, the solvent was distilled off under reduced pressure and the resulting residue was purified by silica gel column chromatography [eluent:n-hexane-ethyl acetate (4:1)] to give 8-(5-methoxy-2-benzimidazolyl)thiomethyl-1-methyl-1,2,3,4-tetrahydroquinoline (5.0 g).

NMR (CDCl$_3$) δ: 1.60–2.00 (2H, m), 2.70 (2H, t, J=7Hz), 2.73 (3H, s), 2.83–3.23 (2H, m), 3.73 (3H, s), 4.30 (2H, s), 6.67–7.40 (6H, m), 12.50 (1H, br.).

In a manner analogous to Example 159, by using appropriate starting materials, the compounds prepared in Examples 2 to 157 were produced.

EXAMPLE 160

To a solution of 8-(5-methoxy-2-benzimidazolyl)thiomethyl-1-methyl-1,2,3,4-tetrahydroquinoline (0.80 g) in dichloromethane (30 ml) was added a solution of m-chloroperbenzoic acid (80%, 0.51 g) in dichloromethane (10 ml) by use of a pipet at −60° C. The mixture was stirred for 30 minutes at the same temperature. Aqueous sodium carbonate was added to the reaction mixture and the mixture was extracted with dichloromethane. The extract was dried over anhydrous magnesium sulfate and the solvent was distilled off. The resulting residue was purified by silica gel column chromatography [eluent:ethyl acetate-n-hexane (2:3)] and recrystallized from ethyl acetate to give 8-(5-methoxy-2-benzimidazolyl)sulfinylmethyl-1-methyl-1,2,3,4-tetrahydroquinoline (0.38 g).

Colorless needle crystal
mp: 137°–137.5° C.

In a manner analogous to Example 160, the compounds shown in the table below were produced using appropriate starting materials. In the column of "bond between the 3- and 4-positions of the quinoline skeleton" in the table, the symbol "s" means a single bond and "d" means a double bond.

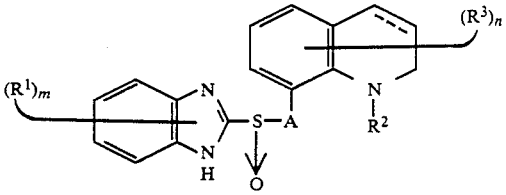

| Example No. | R¹ | m | A | R² | R³ | n | bond between the 3- and 4-positions of the quinoline skeleton | Crystal form (recrystallization solvent) | Melting point (°C.) |
|---|---|---|---|---|---|---|---|---|---|
| 161 | H | 1 | CH₂ | C₂H₅ | H | 1 | s | White powder (diethyl ether-n-hexane) | 125–125.5 |
| 162 | 5-CH₃ | 1 | CH₂ | C₂H₅ | H | 1 | s | Colorless needle crystals (dichloromethane-diethyl ether) | 141 |
| 163 | 5-OCH₃ | 1 | CH₂ | C₂H₅ | H | 1 | s | White powder (diethyl ether-n-hexane) | 115–117 |
| 164 | 5-F | 1 | CH₂ | C₂H₅ | H | 1 | s | White powder (diethyl ether) | 139–139.5 |
| 165 | 5-F 6-F | 2 | CH₂ | C₂H₅ | H | 1 | s | White powder (diethyl ether) | 145–146 |
| 166 | 5-F 6-OCH₃ | 2 | CH₂ | C₂H₅ | H | 1 | s | White powder (diethyl ether) | 129–130.5 |
| 167 | 5-OC₂H₅ 6-F | 2 | CH₂ | C₂H₅ | H | 1 | s | White powder (diethyl ether-n-hexane) | 117–118.5 |
| 168 | 5-Cl | 1 | CH₂ | C₂H₅ | H | 1 | s | White powder (diethyl ether) | 117–119 |
| 169 | 5-COCH₃ | 1 | CH₂ | C₂H₅ | H | 1 | s | Brown colored powder (diethyl ether) | 119–122 |
| 170 | 5-CF₃ | 1 | CH₂ | C₂H₅ | H | 1 | s | White powder (diethyl ether) | 120–121.5 |
| 171 | 4-CH₃ | 1 | CH₂ | C₂H₅ | H | 1 | s | Colorless needle crystals (diethyl ether-n-hexane) | 130.5–131 |
| 172 | 4-CH₃ 6-CH₃ | 2 | CH₂ | C₂H₅ | H | 1 | s | White powder (ethyl acetate-n-hexane) | 139.5–140.5 |
| 173 | 5-CH₃ 6-CH₃ | 2 | CH₂ | C₂H₅ | H | 1 | s | Pale yellow powder (dichloromethane-diethyl ether) | 137–138.5 |
| 174 | H | 1 | CH₂ | CH₃ | H | 1 | s | White powder (diethyl ether-n-hexane) | 112–113 |
| 175 | 5-F | 1 | CH₂ | CH₃ | H | 1 | s | Colorless needle crystals (ethyl acetate-n-hexane) | 132.5–133.5 |
| 176 | 5-CH₃ | 1 | CH₂ | CH₃ | H | 1 | s | Colorless needle crystals (ethyl acetate-n-hexane) | 126–127 |
| 177 | 5-Cl | 1 | CH₂ | CH₃ | H | 1 | s | Colorless needle crystals (chloroform-ethyl acetate-n-hexane) | 135–136.5 |
| 178 | 4-CH₃ | 1 | CH₂ | CH₃ | H | 1 | s | Colorless needle crystals (ethyl acetate-n-hexane) | 131.5–133 |
| 179 | 5-F 6-OCH₃ | 2 | CH₂ | CH₃ | H | 1 | s | White powder (ethyl acetate) | 159.5–160 |
| 180 | H | 1 | CH₂ | CH₂CH=CH₂ | H | 1 | s | White needle crystals (dichloromethane-diethyl ether) | 127.5–123.5 |
| 181 | 5-OCH₃ | 1 | CH₂ | CH₂CH=CH₂ | H | 1 | s | White needle crystals (dichloromethane-diethyl ether) | 122.5–123.5 |
| 182 | 5-F | 1 | CH₂ | CH₂CH=CH₂ | H | 1 | s | White needle crystals | 135.5–136.0 |

-continued

| Example No. | R¹ | m | A | R² | R³ | n | bond between the 3- and 4- positions of the quinoline skeleton | Crystal form (recrystallization solvent) | Melting point (°C.) |
|---|---|---|---|---|---|---|---|---|---|
| 183 | H | 1 | CH₂ | n-C₄H₉ | H | 1 | s | White needle crystals (dichloromethane-diethyl ether) | 118.0–119.0 |
| 184 | 5-CH₃ | 1 | CH₂ | n-C₄H₉ | H | 1 | s | White needle crystals (dichloromethane-diethyl ether) | 121.5–122.0 |
| 185 | 5-OCH₃ | 1 | CH₂ | n-C₄H₉ | H | 1 | s | White needle crystals (dichloromethane-diethyl ether) | 113.0–114.0 |
| 186 | H | 1 | CH₂ | CH₂—C≡CH | H | 1 | s | White needle crystals (dichloromethane-diethyl ether) | 145.0–146.5 |
| 187 | 5-CH₃ | 1 | CH₂ | CH₂—C≡CH | H | 1 | s | White powder (dichloromethane-diethyl ether) | 140.0–141.0 |
| 188 | H | 1 | CH₂ | ⌬—CH₂ | H | 1 | s | White needle crystals (dichloromethane-diethyl ether) | 125.5–126.5 |
| 189 | 5-CH₃ | 1 | CH₂ | ⌬—CH₂ | H | 1 | s | White powder (dichloromethane-diethyl ether) | 145.0–146.5 |
| 190 | H | 1 | CH₂ | CH₃ | 4-CH₃ | 1 | s | White powder (dichloromethane-petroleum ether) | 102.5–103 |
| 191 | 5-F 6-OCH₃ | 2 | CH₂ | CH₃ | 4-CH₃ | 1 | s | White powder (dichloromethane-petroleum ether) | 119.5–120.5 |
| 192 | H | 1 | CH₂ | C₂H₅ | 6-Br | 1 | s | White powder (dichloromethane) | 140–140.5 |
| 193 | 4-CH₃ 6-CH₃ | 2 | CH₂ | CH₃ | H | 1 | s | White powder (ethyl acetate) | 128.5–129 |
| 194 | H | 1 | CH₂ | CH₂C≡CSi(CH₃)₃ | H | 1 | s | White powder (dichloromethane-diethyl ether) | 129.5–130.0 |
| 195 | 5-COCH₃ | 1 | CH₂ | CH₃ | H | 1 | s | Yellow powder (dichloromethane-diethyl ether) | 123–124 |
| 196 | 5-F 6-OCH₃ | 2 | CH₂ | C₂H₅ | 6-Br | 1 | s | White powder (dichloromethane-diethyl ether) | 128–129 |
| 197 | H | 1 | CH₂ | C₂H₅ | 6-OCH₃ | 1 | s | White powder | 135–136 |

-continued

| Example No. | R¹ | m | A | R² | R³ | n | bond between the 3- and 4- positions of the quinoline skeleton | Crystal form (recrystallization solvent) | Melting point (°C.) |
|---|---|---|---|---|---|---|---|---|---|
| 198 | 5-F | 2 | $CH_2$ | $C_2H_5$ | 6-$OCH_3$ | 1 | s | White powder (dichloromethane-diethyl ether) | 144.0–145.0 |
| 199 | 6-$OCH_3$ 5-$CO_2CH_3$ | 1 | $CH_2$ | $CH_3$ | H | 1 | s | Pale brown powder (diethyl ether) | 117–119 (decomposition) |
| 200 | 5-$OC_2H_5$ 6-F | 2 | $CH_2$ | $CH_3$ | H | 1 | s | White powder (ethyl acetate) | 136 |
| 201 | 5-F 6-$CH_3$ | 2 | $CH_2$ | $CH_3$ | H | 1 | s | White powder (dichloromethane-diethyl ether) | 154–155 |
| 202 | 5-F 6-$CH_3$ | 2 | $CH_2$ | $C_2H_5$ | H | 1 | s | White powder (ethyl acetate) | 151–153 |
| 203 | 5-F | 1 | $CH_2$ | $C_2H_5$ | 6-$OCH_3$ | 1 | s | White powder (dichloromethane-diethyl ether) | 144.0–145.0 |
| 204 | 5-F 6-$OCH_3$ | 2 | $CH_2$ | $CH_2CH=CH_2$ | H | 1 | s | Pale yellow needle crystals (ethyl acetate) | 132–135 |
| 205 | 4-$CH_3$ | 1 | $CH_2$ | $CH_2CH=CH_2$ | H | 1 | s | Colorless needle crystals (ethyl acetate) | 140–141 |
| 206 | 4-$CH_3$ 6-$CH_3$ | 2 | $CH_2$ | $CH_2CH=CH_2$ | H | 1 | s | Colorless needle crystals (ethyl acetate-n-hexane) | 143–143.5 |
| 207 | 5-$CH_3$ | 1 | $CH_2$ | $CH_2CH=CH_2$ | H | 1 | s | Colorless needle crystals (ethyl acetate) | 136.5–138.5 |
| 208 | 5-F 6-$OC_2H_5$ | 2 | $CH_2$ | $CH_2CH=CH_2$ | H | 1 | s | White powder (ethyl acetate) | 144–145 |
| 209 | 5-Cl | 1 | $CH_2$ | $CH_2CH=CH_2$ | H | 1 | s | Colorless needle crystals (ethyl acetate) | 135–136 |
| 210 | 5-$COCH_3$ | 1 | $CH_2$ | $CH_2CH=CH_2$ | H | 1 | s | Colorless needle crystals (diethyl ether) | 128–130 |
| 211 | H | 1 | $CH_2$ | $CH_2$–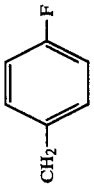 | H | 1 | s | White powder (dichloromethane-diethyl ether) | 146–147 |
| 212 | 5-$CH_3$ | 1 | $CH_2$ | $CH_2$–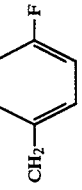 | H | 1 | s | White powder (dichloromethane-diethyl ether) | 168–169 |
| 213 | 5-F 6-$OCH_3$ | 2 | $CH_2$ | $CH_2$–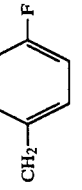 | H | 1 | s | White powder (dichloromethane-diethyl ether) | 151–152 |

-continued

| Example No. | R¹ | m | A | R² | R³ | n | bond between the 3- and 4- positions of the quinoline skeleton | Crystal form (recrystallization solvent) | Melting point (°C.) |
|---|---|---|---|---|---|---|---|---|---|
| 214 | 5-OCH₃ | 1 | CH₂ | CH₂C≡CH | H | 1 | s | White powder (dichloromethane-diethyl ether) | 131–132 |
| 215 | 5-F | 2 | CH₂ | CH₂C≡CH | H | 1 | s | White powder (dichloromethane-diethyl ether) | 138–139 |
| 216 | H | 1 | CH₂ | CH₂CH=CH₂ | 4-CH₃ | 1 | s | White powder | 121.5 |
| 217 | 5-F 6-OCH₃ | 2 | CH₂ | CH₂CH=CH₂ | 4-CH₃ | 1 | s | Colorless needle crystals (diethyl ether) | 133–135 (decomposition) |
| 218 | H | 1 | CH₂ |  | H | 1 | s | White powder (dichloromethane-diethyl ether) | 123–124 (decomposition) |
| 219 | 5-F 6-OCH₃ | 2 | CH₂ |  | H | 1 | s | White powder (dichloromethane-diethyl ether) | 132-14 133.5 (decomposition) |
| 220 | H | 1 | CH₂ | CH₂CF₃ | H | 1 | s | White powder (dichloromethane-diethyl ether) | 150–151 |
| 221 | 5-CH₃ | 1 | CH₂ | CH₃CF₃ | H | 1 | s | White powder (dichloromethane-diethyl ether) | 168.5–169.5 |
| 222 | 5-F 6-OCH₃ | 1 | CH₂ | CH₂CF₃ | H | 1 | s | White powder (dichloromethane-diethyl ether) | 172.5–173.5 |
| 223 | H | 1 | CH₂ | C₂H₅ | 4-CH₃ | 1 | s | Colorless needle crystals (ethyl acetate) | 125–126 |
| 224 | 5-F 6-OCH₃ | 2 | CH₂ | C₂H₅ | 4-CH₃ | 1 | s | Colorless needle crystals (ethyl acetate) | 135–137 |
| 225 | 5-COCH₃ | 1 | CH₂ | C₂H₅ | 4-CH₃ | 1 | s | Colorless needle crystals (ethyl acetate) | 140–141.5 |
| 226 | H | 1 | CH₂ | CH₂CH=CH₂ | 3-CH₃ | 1 | s | Colorless needle crystals (ethyl acetate-diethyl ether) | 124.5–125.5 |
| 227 | 5-CH₃ | 1 | CH₂ | CH₂CH=CH₂ | 3-CH₃ | 1 | s | White powder (diethyl ether) | 137.5–138.5 |
| 228 | 5-OCH₃ | 1 | CH₂ | CH₂CH=CH₂ | 3-CH₃ | 1 | s | White powder (ethyl acetate-diethyl ether) | 124.5–125.5 |
| 229 | 5-F | 1 | CH₂ | CH₂CH=CH₂ | 3-CH₃ | 1 | s | White powder (diethyl ether-n-hexane) | 141–143 |
| 230 | 5-F 6-OCH₃ | 2 | CH₂ | CH₂CH=CH₂ | 3-CH₃ | 1 | s | Colorless needle crystals (diethyl ether) | 145.5–146 |
| 231 | H | 1 | CH₂ | CH₂C≡CH | 4-CH₃ | 1 | s | White powder (dichloromethane-diethyl ether) | 117–119 |

-continued

| Example No. | R[1] | m | A | R[2] | R[3] | n | bond between the 3- and 4- positions of the quinoline skeleton | Crystal form (recrystallization solvent) | Melting point (°C.) |
|---|---|---|---|---|---|---|---|---|---|
| 232 | H | 1 | $CH_2$ | $CH_2CH_2N\begin{smallmatrix}CH_3\\CH_3\end{smallmatrix}$ | H | 1 | s | White powder (dichloromethane-diethyl ether) | 141.5–142.5 (decomposition) |
| 233 | H | 1 | $CH_2$ | $C_2H_5$ | 3-$CH_3$ | 1 | s | Colorless needle crystals (ethanol-ethyl acetate) | 136–137 |
| 234 | 5-F 6-$OCH_3$ | 2 | $CH_2$ | $C_2H_5$ | 3-$CH_3$ | 1 | s | White powder (diethyl ether) | 160.5–161.5 |
| 235 | 5-$CH_3$ | 1 | $CH_2$ | $CH_3$ | 4-$CH_3$ | 1 | d | Pale yellow needle crystals (ethyl acetate) | 148–149 |
| 236 | 5-$OCH_3$ | 1 | $CH_2$ | $CH_3$ | 4-$CH_3$ | 1 | d | Yellow granules (diethyl ether) | 132–133 |
| 237 | 5-F 6-$OCH_3$ | 2 | $CH_2$ | $CH_3$ | 4-$CH_3$ | 1 | d | Pale yellow powder (diethyl ether-dichloromethane-n-hexane) | 157–159 (decomposition) |
| 238 | H | 1 | $CH_2$ | $C_2H_5$ | 4-$CH_3$ | 1 | d | White powder (¼ hydrate) (diethyl ether) | 127–130 (decomposition) |
| 239 | 5-F 6-$OCH_3$ | 2 | $CH_2$ | $C_2H_5$ | 4-$CH_3$ | 1 | d | Pale yellow powder (¼ hydrate) (diethyl ether) | 140–142 (decomposition) |
| 240 | H | 1 | $CH_2$ | $CH_3$ | 3-$CH_3$ 4-$CH_3$ | 2 | d | White powder (diethyl ether) | 148–149.5 (decomposition) |
| 241 | H | 1 | $CH_2$ | $CH_3$ | 4=O | 1 | s | Yellow powder (dichloromethane-diethyl ether) | 153–154 |
| 242 | H | 1 | $CH_2$ | $CH_3$ | 4-OH | 1 | s | White powder (dichloromethane-diethyl ether) | 111–112 (decomposition) |
| 243 | H | 1 | $CH_2$ | $CH_3$ | 4-OH 4-$CH_3$ | 2 | s | White powder dichloromethane-(diethyl ether) | 136–137 |
| 244 | H | 1 | $CH_2$ | $CH_3$ | 4-OH 4-$C_2H_5$ | 2 2 | s s | White powder (dichloromethane-petroleum ether) | 123–124 (decomposition) |
| 245 | H | 1 | $CH_2$ | $CH_3$ | ![4-dioxolane] | 1 | s | NMR[100] | |
| 246 | H | 1 | $CH_2$ | $C_2H_5$ | 4-$OCH_3$ | 1 | s | Pale yellow powder (dichloromethane-diethyl ether) | 118–118.5 (decomposition) |

-continued

| Example No. | R¹ | m | A | R² | R³ | n | bond between the 3- and 4- positions of the quinoline skeleton | Crystal form (recrystallization solvent) | Melting point (°C.) |
|---|---|---|---|---|---|---|---|---|---|
| 247 | H | 1 | CH₂ | C₂H₅ | 4- (phenyl) | 1 | s | Colorless needle crystals (petroleum ether) | 87-89 |
| 248 | 5-CH₃ | 1 | CH₂ | C₂H₅ | 4- (phenyl) | 1 | s | Colorless needle crystals (petroleum ether) | 137-139 |
| 249 | 5-F | 2 | CH₂ | C₂H₅ | 4- (phenyl) | 1 | s | White powder (diethyl ether) | 153-154 |
| 250 | H | 1 | CH₂ | C₂H₅ | 4-OCH₃ | 1 | s | Yellow powder (dichloromethane-diethyl ether) | 118-118.5 (decomposition) |
| 251 | 5-CH₃ | 1 | CH₂ | C₂H₅ | 4-OCH₃ | 1 | s | White powder (dichloromethane-diethyl ether) | 148.5-149.5 |
| 252 | 5-OCH₃ | 1 | CH₂ | C₂H₅ | 4-OCH₃ | 1 | s | White powder (dichloromethane-diethyl ether) | 149-150 |
| 253 | 5-F 6-OCH₃ | 2 | CH₂ | C₂H₅ | 4-OCH₃ | 1 | s | Yellow powder (dichloromethane-diethyl ether) | 131-132 |
| 254 | 5-OC₂H₅ 6-F | 2 | CH₂ | C₂H₅ | 4-OCH₃ | 1 | s (dichloromethane-diethyl ether) | White powder | 135-136 |
| 255 | 5-COCH₃ | 1 | CH₂ | C₂H₅ | 4-OCH₃ | 1 | s | White powder (dichloromethane-diethyl ether) | 149-150.5 |
| 256 | H | 1 | CH₂ | C₂H₅ | 4-N(CH₃)₂ | 1 | s | Yellow needle crystals (dichloromethane-petroleum ether) | 141-142 |
| 257 | 5-F 6-OCH₃ | 2 | CH₂ | C₂H₅ | 4-N(CH₃)₂ | 1 | s | White powder (dichloromethane-diethyl ether) | 162-163 |
| 258 | H | 1 | CH₂ | C₂H₅ | 4-NHCH₃ | 1 | s | White powder (dichloromethane-petroleum ether) | 102-104 |
| 259 | H | 1 | CH₂ | C₂H₅ | 4=NOH | 1 | s | White powder (dichloromethane- | 168-169 |

-continued

| Example No. | R¹ | m | A | R² | R³ | n | bond between the 3- and 4- positions of the quinoline skeleton | Crystal form (recrystallization solvent) | Melting point (°C.) |
|---|---|---|---|---|---|---|---|---|---|
| 260 | H | 1 | $CH_2$ | $C_2H_5$ | 4-$OCH_2CH=CH_2$ | 1 | s | Colorless needle crystals (ethyl acetate-n-hexane) | 128.5–129 |
| 261 | H | 1 | $CH_2$ | $C_2H_5$ | 4=$CH_2$ | 1 | s | White powder (dichloromethane-diethyl ether) | 159.5–160.5 |
| 262 | H | 1 | $CH_2$ | $C_2H_5$ |  | 1 | s | White powder (dichloromethane-diethyl ether) | 141–142 |
| 263 | H | 1 | $CH_2$ | $C_2H_5$ | 3-$COOCH_3$ | 1 | s | White powder (dichloromethane-diethyl ether) | 173–174 |
| 264 | H | 1 | $CH_2$ | $C_2H_5$ | 3-$CH_2OH$ | 1 | s | White powder (chloroform-ethanol-diethyl ether) | 137–138 (decomposition) |
| 265 | H | 1 | $CH_2$ | $C_2H_5$ | 3-CON(CH₃)(CH₃) | 1 | s | White powder (½ hydrate) (dichloromethane-diethyl ether) | 133–135 |
| 266 | H | 1 | $CH_2$ | $C_2H_5$ | 3-$CO_2H$ | 1 | s | Colorless needle crystals (½ hydrate) (methanol) | 162–165 (decomposition) |
| 267 | 5-$OCH_3$ | 1 | $CH_2$ | $C_2H_5$ | 3-$CH_2OH$ | 1 | s | White powder (chloroform-ethanol-diethyl ether) | 147–148 (decomposition) |
| 268 | H | 1 | $CH_2$ | $C_2H_5$ |  | 1 | s | NMR¹⁰¹ | |
| 269 | 5-$CH_3$ | 1 | $CH_2$ | $C_2H_5$ | 4-$OCH_2CH=CH_2$ | 1 | s | White powder (dichloromethane-diethyl ether) | 156–156.5 |
| 270 | 5-$COCH_3$ | 1 | $CH_2$ | $C_2H_5$ | 4-$OCH_2CH=CH_2$ | 1 | s | Colorless needle crystals (dichloromethane-diethyl ether) | 131–133 |
| 271 | H | 1 | $CH_2$ | $C_2H_5$ | 4 = O | 1 | s | Yellow powder (chloroform-diethyl ether) | 168–169 |
| 272 | H | 1 | $CH_2$ | $C_2H_5$ | 4-OH | 1 | s | White powder (dichloromethane-diethyl ether) | 117–118 |

-continued

| Example No. | R$^1$ | m | A | R$^2$ | R$^3$ | n | bond between the 3- and 4- positions of the quinoline skeleton | Crystal form (recrystallization solvent) | Melting point (°C.) |
|---|---|---|---|---|---|---|---|---|---|
| 273 | 5-F | 2 | CH$_2$ | C$_2$H$_5$ | 3-CH$_2$OH | 1 | s | White powder (chloroform-ethanol-diethyl ether) | 149-150 (decomposition) |
| 274 | 5-CH$_3$ | 1 | CH$_2$ | C$_2$H$_5$ | 3-CH$_2$OH | 1 | s | White powder (dichloromethane-diethyl ether) | 143.5-144.5 (decomposition) |
| 275 | 5-COCH$_3$ | 1 | CH$_2$ | CH$_2$CH=CH$_2$ | 4-OCH$_3$ | 1 | s | Colorless needle crystals (dichloromethane-diethyl ether) | 129-130 |
| 276 | 5-COCH$_3$ | 1 | CH$_2$ | C$_2$H$_5$ | 3,3-diCH$_3$ <br> 4=O | 3 | s | Yellow powder (diethyl ether-n-hexane) | 127-129 |
| 277 | 5-F <br> 6-OCH$_3$ | 2 | CH$_2$ | CH$_2$CH=CH$_2$ | 4-N(CH$_3$)CH$_3$ | 1 | s | Pale yellow powder (dichloromethane-petroleum ether) | 124-125 |
| 278 | H | 1 | CH$_2$ | CH$_2$CH=CH$_2$ | 4-N(CH$_3$)CH$_3$ | 1 | s | Pale yellow powder (dichloromethane-petroleum ether) | 152-153 |
| 279 | H | 1 | CH$_2$ | C$_2$H$_5$ | 4-N(CH$_3$)CH$_2$CH$_2$OH | 1 | s | White powder (dichloromethane-diethyl ether) | 138-139 |
| 280 | H | 1 | CH$_2$ | C$_2$H$_5$ | 4-N(CH$_3$)COCH$_3$ | 1 | s | White powder (dichloromethane-Diethyl ether) | 116-118 |
| 281 | 5-F <br> 6-OCH$_3$ | 2 | CH$_2$ | C$_2$H$_5$ | 4-N(CH$_3$)(cyclopropyl) | 1 | s | White powder (diethyl ether-n-hexane) | 141-143 |
| 282 | 5-F <br> 6-OCH$_3$ | 2 | CH$_2$ | H | 4-N(CH$_3$)CH$_2$CH=CH$_2$ | 1 | s | Yellow powder (dichloromethane-petroleum ether) | 92-93 |

-continued

| Example No. | R¹ | m | A | R² | R³ | n | bond between the 3- and 4- positions of the quinoline skeleton | Crystal form (recrystallization solvent) | Melting point (°C.) |
|---|---|---|---|---|---|---|---|---|---|
| 283 | 5-F 6-OCH₃ | 2 | CH₂ | C₂H₅ | 4-N(CH₃)(CH₂-cyclopropyl) | 1 | s | Yellow powder (dichloromethane-petroleum ether) | 116–118 |
| 284 | 5-F 6-OCH₃ | 2 | CH₂ | C₂H₅ | 4-N(CH₃)(CH(OC₂H₅)CF₃) | 1 | s | Yellow powder (dichloromethane-petroleum ether) | 142–143 |
| 285 | 5-F 6-OCH₃ | 2 | CH₂ | C₂H₅ | 4-N-pyrrolidinyl | 1 | s | Yellow powder (dichloromethane-petroleum ether) | 146–148 |
| 286 | 5-F 6-OCH₃ | 2 | CH₂ | C₂H₅ | 4-N(CH₃)((CH₂)₂OH) | 1 | s | White powder (dichloromethane-petroleum ether) | 149–150 |
| 287 | 5-F 6-OCH₃ | 2 | CH₂ | C₂H₅ | 4-N(CH₂CH=CH₂)(COCH₃) | 1 | s | White powder (diethyl ether-n-hexane) | 121–124 |
| 288 | 5-F 6-OCH₃ | 2 | CH₂ | C₂H₅ | 4-N(CH₂CH=CH₂)(CH₂-C₆H₄-4-OCH₃) | 1 | s | White powder (petroleum ether) | 85–89 |
| 289 | 5-F 6-OCH₃ | 2 | CH₂ | C₂H₅ | 4-N(CH₂CH=CH₂)(C₂H₅) | 1 | s | Colorless prisms (diethyl ether-n-hexane) | 110–114 |

-continued

| Example No. | R¹ | m | A | R² | R³ | n | bond between the 3- and 4- positions of the quinoline skeleton | Crystal form (recrystallization solvent) | Melting point (°C.) |
|---|---|---|---|---|---|---|---|---|---|
| 290 | H | 1 | $CH_2$ | $C_2H_5$ | 3-$CH_2N(CH_3)_2$ | 1 | s | White powder (diethyl ether) | 98–101 (decomposition) |
| 291 | H | 1 | $CH_2$ | $C_2H_5$ | 3-CON(morpholine) | 1 | s | White powder (½ hydrate) (dichloromethane-diethyl ether) | 160–162 (decomposition) |
| 292 | 5-F 6-$OCH_3$ | 2 | $CH_2$ | $C_2H_5$ | 3-CON(pyrrolidine) | 1 | s | White powder (½ hydrate) (dichloromethane-diethyl ether) | 180.5–181.5 (decomposition) |
| 293 | H | 1 | $CH_2$ | $C_2H_5$ | 3-CON(piperidine) | 1 | s | White granules (dichloromethane-diethyl ether) | 139–140 (decomposition) |
| 294 | 5-F 6-$OCH_3$ | 2 | $CH_2$ | $C_2H_5$ | 3-$CNH(CH_2)_2$-(3,4-di-$OCH_3$-phenyl), C=O | 1 | s | White powder (hydrate) (dichloromethane-diethyl ether) | 140–142 |
| 295 | 5-$CH_3$ | 1 | $CH_2$ | $C_2H_5$ | 4-N($CH_3$)($CH_2CH=CH_2$) | 1 | s | White powder (petroleum ether) | 109–111 |
| 296 | 5-$COCH_3$ | 1 | $CH_2$ | $C_2H_5$ | 4-N($CH_3$)($CH_2CH=CH_2$) | 1 | s | Pale yellow powder (petroleum ether) | 115–118 |
| 297 | 5-F 6-$OCH_3$ | 2 | $CH_2$ | $C_2H_5$ | 4-N($CH_3$)($CH_2CH=CH_2$) | 1 | s | White powder (petroleum ether) | 111–115 |

-continued

| Example No. | R¹ | m | A | R² | R³ | n | bond between the 3- and 4- positions of the quinoline skeleton | Crystal form (recrystallization solvent) | Melting point (°C.) |
|---|---|---|---|---|---|---|---|---|---|
| 298 | 5-CH₃ | 1 | CH₂ | C₂H₅ | 4-NHCH₂CH=CH₂ | 1 | s | White powder (dichloromethane-diethyl ether) | 162–164 |
| 299 | 5-CH₃ | 1 | CH₂ | C₂H₅ | 4-NH–cyclohexyl | 1 | s | White powder (petroleum ether) | 135–138 |
| 300 | 5-F 6-OCH₃ | 2 | CH₂ | CH₂CH=CH₂ | 4-OCH₃ | 1 | s | White powder (dichloromethane-diethyl ether) | 143–144 |
| 301 | 5-CH₃ | 1 | CH₂ | CH₂CH=CH₂ | 4-OCH₃ | 1 | s | Colorless needle crystals (dichloromethane-diethyl ether) | 129.5–130.5 |
| 302 | 5-COCH₃ | 1 | CH₂ | C₂H₅ | 4-OCH₂OCH₃ | 1 | s | White powder (dichloromethane-diethyl ether) | 132.5–133.5 |
| 303 | 5-F 6-OCH₃ | 2 | CH₂ | C₂H₅ | 4-CH₂OH | 1 | s | White powder (dichloromethane-diethyl ether) | 139–140 |
| 304 | 5-COCH₃ | 1 | CH₂ | C₂H₅ | 4-N(CH₃)(cyclopropyl) | 1 | s | White powder (petroleum ether) | 125–128 |
| 305 | 5-F 6-OCH₃ | 2 | CH₂ | C₂H₅ | 4-N(CHO)(cyclopropyl) | 1 | s | White powder (diethyl ether-n-hexane) | 105–110 |
| 306 | 5-F 6-OCH₃ | 2 | CH₂ | C₂H₅ | 4-N(CH₃)(COCF₃) | 1 | s | White powder (dichloromethane-petroleum ether) | 159–160 |
| 307 | 5-F 6-OCH₃ | 2 | CH₂ | C₂H₅ | 4-N(CH₃)(cyclohexyl) | 1 | s | Colorless needle crystal (½ hydrate) (ethyl acetate-n-hexane) | 164–168 (decomposition) |
| 308 | H | 1 | CH₂ | C₂H₅ | 4-CF₃ | 1 | d | White granules | 142–144 |

-continued

| Example No. | R¹ | m | A | R² | R³ | n | bond between the 3- and 4- positions of the quinoline skeleton | Crystal form (recrystallization solvent) | Melting point (°C.) |
|---|---|---|---|---|---|---|---|---|---|
| 309 | 5-CH₃ | 1 | CH₂ | C₂H₅ | 4-OCH₃ 3,3-diCH₃ | 3 | s | (diethyl ether-n-hexane) White powder (petroleum ether-n-hexane) | 110–112 |
| 310 | 5-CO— | 1 | CH₂ | CH₂CH=CH₂ | 4-N(CH₃)(CH₃) | 1 | s | White powder (diethyl ether-n-hexane) | 154–155 |
| 311 | 5-COCH₃ | 1 | CH₂ | CH₂CH=CH₂ | 4-N(CH₃)(CH₃) | 1 | s | NMR¹⁰² | |

¹⁰⁰NMR(CDCl₃)δ:
2.15–2.27 (2H, m), 2.99 (3H, m), 3.48–3.59 (2H, m), 4.07–4.27 (4H, m), 4.38 (2H, s), 6.88–8.00 (7H, m)
¹⁰¹NMR(CDCl₃)δ:
1.21 and 1.27 (3H, t, J = 7 Hz), 1.32–1.49 (1H, m), 1.58–1.80 (4H, m), 1.80–2.10 (1H, m), 2.28–2.49 (2H, m), 2.49–2.70 (2H, m), 2.70–2.87 (1H, m), 2.87–3.14 (3H, m), 3.35 and 3.50 (1H, t, J = 5 Hz), 4.35 and 4.47 (1H, d, J = 13 Hz), 4.61 and 4.78 (1H, d, J = 13 Hz), 6.78 and 6.84 (1H, t, J = 8 Hz), 7.15–7.38 (4H, m), 7.53–7.70 (2H, m)
¹⁰²NMR(CDCl₃)δ:
1.35–2.02 (2H, m), 2.19 (3H, s), 2.21 (3H, s), 2.48–2.77 (1H, m), 2.68 (3H, s), 2.77–3.02 (1H, m), 3.37–3.83 (3H, m), 4.35–4.85 (2H, m), 5.10–5.50 (2H, m), 5.83–6.17 (1H, m), 6.80–6.96 (1H, m), 7.07–7.22 (1H, m), 7.44–7.69 (2H, m), 7.98 (1H, dd, J = 1.1 Hz, 6.9 Hz), 8.27 (1H, s)

EXAMPLE 312

1,4-Dimethyl-8-(2-benzimidazolyl)thiomethyl-1,2-dihydroquinoline (0.4 g) was dissolved in dichloromethane (30 ml). To this solution was added dropwise a solution of m-chloroperbenzoic acid (0.27 g) in dichloromethane (5 ml) at −40° C. with stirring. After the mixture was stirred for 20 minutes at the same temperature, the reaction mixture was washed with an aqueous solution of sodium carbonate and extracted with dichloromethane. The extract was dried over anhydrous magnesium sulfate and the solvent was distilled off. Diethyl ether was added to the resulting residue to precipitate crystals. The resulting crystals were recrystallized from dichloromethane-diethyl ether to give 1,4-dimethyl-8-(2-benzimidazolyl)sulfinylmethyl-1,2-dihydroquinoline (0.2 g).

Pale brown powder
mp: 159.5°–160.5° C. (decomposition)

EXAMPLE 313

(1-Methyl-1,2,3,4-tetrahydroquinolin-8-yl)methyl lithium (18.3 g) was dissolved in benzene (150 ml). After adding (5-methoxy-2-benzimidazolyl)sulfinyl chloride (20.1 g) thereto, the mixture was refluxed for 2 hours. The resulting lithium chloride was filtered off, and the filtrate was concentrated under reduced pressure. The resulting residue was recrystallized from ethyl acetate to give 8-(5-methoxy-2-benzimidazolyl)sulfinylmethyl-1-methyl-1,2,3,4-tetrahydroquinoline (1.1 g).

Colorless needle crystal
mp: 137°–137.5° C.

In a manner analogous to Example 313, the same compounds as those prepared in Examples 161 to 312 were produced using appropriate starting materials.

EXAMPLE 314

8-(2-Benzimidazolyl)sulfinylmethyl-1,2,3,4-tetrahydroquinoline (14.9 g) was dissolved in dimethyl formamide (150 ml). Sodium hydride (60% in oil, 2.2 g) was added thereto with stirring under ice-cooling, and the mixture was stirred for 30 minutes. Sequentially, methyl iodide (8.5 g) was added dropwise to the reaction mixture and the mixture was stirred for 5 hours at 70° to 80° C. After distilling off the solvent, the residue was poured into water and the mixture was extracted with chloroform. The residue obtained by distilling off the chloroform was purified by silica gel column chromatography and recrystallized from diethyl ether-n-hexane to give 1-methyl-8-(2-benzimidazolyl)sulfinylmethyl-1,2,3,4-tetrahydroquinoline (2.1 g).

White powder
mp: 112°–113° C.

In a manner analogous to Example 314, the same compounds as those prepared in Examples 1 to 173 and 175 to 313 were obtained using appropriate starting materials.

EXAMPLE 315

To a solution of 8-(2-benzimidazolyl)thiomethyl-1-(3-trimethylsilyl-2-propinyl)-1,2,3,4-tetrahydroquinoline (400 mg) in tetrahydrofuran (20 ml) was added 1M solution of tetra-n-butylammonium fluoride with stirring under ice-cooling, and the mixture was stirred for 30 minutes at the same temperature. After distilling off the solvent, the resulting residue was extracted with dichloromethane. The extract was washed with water and dried over anhydrous magnesium sulfate, and the solvent was distilled off. The resulting residue was purified by silica gel column chromatography [eluent:n-hexane-ethyl acetate (5.5:1)], and recrystallized from dichloromethane-diethyl ether to give 8-(2-benzimidazolyl)thiomethyl-1-propargyl-1,2,3,4-tetrahydroquinoline (0.35 g).

White powder
mp: 122°–122.5° C.

In a manner analogous to Example 315, by using appropriate starting materials, the same compounds as those prepared in Examples 28, 56, 57, 73, 186, 187, 214, 215, and 231 were obtained.

EXAMPLE 316

To a solution of 8-(2-benzimidazolyl)thiomethyl-1-methyl-4-oxo-1,2,3,4-tetrahydroquinoline (300 mg) in methanol (10 ml) was added gradually sodium borohydride (35 mg) at 0° C. The reaction mixture was stirred for 40 minutes at room temperature. After distilling off the solvent, the resulting residue was extracted with dichloromethane, washed with water, and dried. Then the solvent was distilled off and the resulting residue was recrystallized from ethyl acetate-n-hexane to give 8-(2-benzimidazolyl)thiomethyl-1-methyl-4-hydroxy-1,2,3,4-tetrahydroquinoline (238 mg).

White powder
mp: 144.5°–145° C.

In a manner analogous to Example 316, the same compound as those prepared in Example 113, 242, and 272 were obtained using appropriate starting materials.

EXAMPLE 317

To a solution of 8-(2-benzimidazolyl)thiomethyl-1-methyl-4-oxo-1,2,3,4-tetrahydroquinoline (300 mg) in tetrahydrofuran (10 ml) was added dropwise methyl lithium (1.5M solution in tetrahydrofuran) (1.33 ml) with stirring at −10° C. Then the mixture was stirred for 30 minutes at the same temperature. After distilling off the solvent, the residue was extracted with dichloromethane, washed with water, and dried, then the solvent was distilled off. The resulting residue was purified by silica gel column chromatography [eluent:n-hexane-ethyl acetate-dichloromethane (10:5:2)], and recrystallized from dichloromethane-diethyl ether to give 8-(2-benzimidazolyl)thiomethyl-4-hydroxy-1,4-dimethyl-1,2,3,4-tetrahydroquinoline (96 mg).

Yellow powder
mp: 156°–157° C.

In a manner analogous to Example 317, by using appropriate starting materials, the same compounds as those prepared in Examples 86, 243, and 244 were obtained.

EXAMPLE 318

8-(2-Benzimidazolyl)thiomethyl-1-ethyl-4-oxo-1,2,3,4-tetrahydroquinoline (1.5 g), hydroxylamine hydrochloride (458 mg) and sodium acetate (1.7 g) were dissolved in a mixed solvent (23 ml) of ethanol-water (20:3), and the solution was refluxed for 3 hours. After completion of the reaction, the solvent was distilled off and the resulting residue was poured into water. The precipitated crystals were collected by filtration and recrystallized from methanol to give 8-(2-benzimidazolyl)thiomethyl-1-ethyl-4-hydroxyimino-1,2,3,4-tetrahydroquinoline (0.94 g).

Colorless columnar crystal
mp: 201°–202° C.

In a manner analogous to Example 318, the same compound as that prepared in Example 259 was obtained using appropriate starting materials.

EXAMPLE 319

8-(2-Benzimidazolyl)thiomethyl-1-ethyl-4-oxo-1,2,3,4-tetrahydroquinoline (1 g) and methylamine (40% methanol solution, 7.4 ml) were dissolved in methanol (15 ml) and the solution was refluxed for 14 hours. After allowing to cool, sodium borohydride (630 mg) was added by portions with stirring at room temperature, and the mixture was stirred for 1 hour at the same temperature. The solvent was distilled off and the resulting residue was extracted with dichloromethane. The extract was washed with water and dried over anhydrous magnesium sulfate, and the solvent was distilled off. The resulting residue was recrystallized from ethyl acetate to give 8-(2-benzimidazolyl)thiomethyl-1-ethyl-4-methylamino-1,2,3,4-tetrahydroquinoline (970 mg).

Yellow powder
mp: 144°–145° C.

In a manner analogous to Example 319, by using appropriate starting materials, the same compounds as those prepared in Examples 97, 98, 107, 118, 119, 121, 123 to 127, 130, 131, 140 to 143, 148, 151, 155, 156, 256 to 258, 268, 277 to 279, 281 to 285, 288, 289, 295 to 299, 304, 307, 310, 311, 328 to 336 and 339 to 345 were obtained.

EXAMPLE 320

To a solution of 1-ethyl-4-methylamino-8-(2-benzimidazolyl)thiomethyl-1,2,3,4-tetrahydroquinoline (900 mg) in methanol (20 ml) was added glyoxal (10 ml) and the mixture was stirred for 3 hours at room temperature. The solvent was distilled off and the resulting residue was dissolved in methanol, and to this mixture was added gradually sodium borohydride (1 g). After stirring the mixture for 1 hour at room temperature, the reaction mixture was concentrated. The resulting residue was extracted with dichloromethane and dried over anhydrous magnesium sulfate. The residue obtained by distilling off the solvent was purified by silica gel column chromatography [eluent:dichloromethane-methanol (99:1)] to give 1-ethyl-4-[N-methyl-N-(2-hydroxyethyl)amino]-8-(2-benzimidazolyl)thiomethyl-1,2,3,4-tetrahydroquinoline (510 mg).

NMR (CDCl$_3$) δ: 1.42 (3H, t, J=7.2 Hz), 1.73–1.96 (1H, m), 2.10–2.33 (1H, m), 2.23 (3H, s), 2.67 (2H, t, J=5.3 Hz), 2.88–3.10 (1H, m), 3.10–3.38 (2H, m), 3.48–3.70 (3H, m), 3.94 (1H, t, J=8.0 Hz), 4.10 (1H, d, J=14.8 Hz), 4.43 (1H, d, J=14.8 Hz), 7.00–7.69 (7H, m).

In a manner analogous to Example 320, the same compounds as those prepared in Examples 279, 286, 334, 335 and 339 were obtained using appropriate starting materials.

EXAMPLE 321

To a solution of 1-ethyl-4-methylamino-8-(2-benzimidazolyl)thiomethyl-1,2,3,4-tetrahydroquinoline (690 mg) in dichloromethane (20 ml) was added a solution of acetic anhydride (15.6 mg) in dichloromethane (2 ml) with stirring. After stirring the mixture for 30 minutes at room temperature, the reaction mixture was washed with a saturated aqueous sodium hydrogen carbonate and dried over anhydrous magnesium sulfate. The solvent was distilled off and the resulting residue was purified by silica gel column chromatography [eluent:dichloromethane-methanol (99:1)] to give 1-ethyl-4-(N-methyl-N-acetylamino)-8-(2-benzimidazolyl)-thiomethyl-1,2,3,4-tetrahydroquinoline (500 mg).

NMR (CDCl$_3$) δ1.29–1.50 (3H, m), 1.81–2.43 (2H, m), 2.23 and 2.27 (3H, s), 2.65 and 2.69 (3H, s), 2.85–3.65 (4H, m), 4.18 and 4.20 (1H, d, J=14.5 Hz), 4.44 and 4.50 (1H, d, J=14.5 Hz), 5.00 and 5.91 (1H, t, J=7.6 Hz and J=8.3 Hz), 6.87–7.22 (4H, m), 7.30–7.56 (3H, m).

In a manner analogous to Example 321, by using appropriate starting materials, the same compounds as those prepared in Examples 128, 129, 149, 150, 280, 287, 305, 306, 337, 338, 346 and 347 were obtained.

EXAMPLE 322

To a solution of 8-(2-benzimidazolyl)thiomethyl-1-ethyl-1,2,3,4-tetrahydroquinoline-3-carboxylic acid (1.3 g) in tetrahydrofuran (50 ml) were added dropwise triethylamine (0.4 g) and ethyl chloroformate (0.4 g) with stirring under ice-cooling and the mixture was stirred for 30 minutes. Moreover morpholine (0.4 g) was added dropwise thereto and the mixture was stirred for 3 hours at room temperature. The solvent was distilled off and the resulting residue was dissolved in chloroform. The solution was washed with a saturated aqueous solution of sodium hydrogencarbonate and dried over anhydrous magnesium sulfate, and the solvent was distilled off. The resulting residue was purified by silica gel column chromatography [eluent:dichloromethane-methanol (200:1)], and recrystallized from ethyl acetate-ethanol to give 8-(2-benzimidazolyl)thiomethyl-3-morpholinocarbonyl-1-ethyl-1,2,3,4-tetrahydroquinoline (0.7 g).

White powder
mp: 193.5°–194.5° C.

In a manner analogous to Example 322, by using appropriate starting materials, the same compounds as those prepared in Examples 106, 137 to 139, 265, and 291 to 294 were produced.

EXAMPLE 323

A solution of 8-(2-benzimidazolyl)thiomethyl-3-dimethylamido-1-ethyl-1,2,3,4-tetrahydroquinoline (2.0 g) in tetrahydrofuran (10 ml) was added dropwise to a suspension of lithium aluminum hydride (0.58 g) in tetrahydrofuran (50 ml) with stirring under ice-cooling. Then, the mixture was refluxed for 5 hours. To the reaction mixture were added water (0.3 ml) and a solution of sodium hydroxide (0.3 g) in water (1.5 ml). After filtering off the precipitate, the filtrate was dried over anhydrous magnesium sulfate. After distilling off tetrahydrofuran, the resulting residue was recrystallized from ethyl acetate-n-hexane to give 8-(2-benzimidazolyl)thiomethyl-3-dimethylaminomethyl-1-ethyl- 1,2,3,4-tetrahydroquinoline (1.3 g).

White powder
mp: 152°–154° C.

In a manner analogous to Example 323, the same compound as that prepared in Example 290 was obtained using appropriate staring materials.

EXAMPLE 324

To a suspension of methyl triphenylphosphonium bromide (2.65 g)in tetrahydrofuran (50 ml) was added dropwise n-butyllithium (2.2 ml) in a nitrogen flow with stirring at −40° C. After raising the temperature to −20° C., a solution of 8-(2-benzimidazolyl)thiomethyl- 1-ethyl-4-oxo-1,2,3,4-tetrahydroquinoline (500 mg) in tetrahydrofuran (5 ml) was added dropwise. The temperature was raised gradually to room temperature, and the mixture was stirred for 3 hours. Water was added to the reaction mixture, and the mixture was extracted with dichloromethane and dried over anhydrous magnesium sulfate. The residue obtained by distilling off the solvent was purified by silica gel column chromatography [eluent:n-hexane-ethyl acetate (3:1)] and recrystallized from diethyl ether-dichloromethane to give 8-(2-benzimidazolyl)thiomethyl-1-ethyl-4-methylene-1,2,3,4-tetrahydroquinoline (390 mg).

White powder mp: 148°–149° C.

In a manner analogous to Example 324, the same compound as that prepared in Example 261 was obtained using appropriate starting materials.

EXAMPLE 325

To a suspension of lithium aluminium hydride (0.3 g) in tetrahydrofuran (50 ml) was added dropwise a solution of 8-(2-benzimidazolyl)thiomethyl-1-ethyl-3-ethoxycarbonyl-1,2,3,4-tetrahydroquinoline (1.0 g) in tetrahydrofuran (10 ml) with stirring under ice-cooling. The mixture was stirred for 3 hours at the same temperature. To the reaction mixture were added water (0.3 ml) and a solution of sodium hydroxide (0.3 g) in water (1.5 ml). After filtering off the precipitate, the filtrate was dried over anhydrous magnesium sulfate. After distilling off tetrahydrofuran, the resulting residue was recrystallized from ethanol to give 8-(2-benzimidazolyl)thiomethyl-1-ethyl-3-hydroxymethyl-1,2,3,4-tetrahydroquinoline (0.7 g).

White powder mp: 175°–177° C.

In a manner analogous to Example 325, by using appropriate starting materials, the same compounds as those prepared in Examples 109, 114, 115, 147, 264, 267, 273, 274 and 303 were obtained.

EXAMPLE 326

To a solution of 8-(5-fluoro-6-methoxy-2-benzimidazolyl)thiomethyl-1-ethyl-4-acetyloxymethyl-1,2,3,4-tetrahydroquinoline (2.55 g) in methanol (20 ml) was added a saturated aqueous solution of potassium carbonate (10 ml) and the mixture was stirred for 1 hour at room temperature. The reaction mixture was extracted with dichloromethane and dried. The solvent was distilled off to give 8-(5-fluoro-6-methoxy-2-benzimidazolyl)thiomethyl-1-ethyl-4-hydroxymethyl-1,2,3,4-tetrahydroquinoline (1.74 g).

NMR (CDCl$_3$) δ: 1.34 (3H, t, J=7 Hz), 1.9–2.2 (2H, m), 2.9–3.1 (2H, m), 3.1–3.4 (2H, m), 3.5–3.7 (1H, m), 3.7–3.9 (2H, m), 3.82 (3H, s), 4.23 (2H, s), 6.8–7.3 (5H, m).

In a manner analogous to Example 326, by using appropriate starting materials, the same compounds as those prepared in Examples 105, 109, 114, 115, 264, 267, 273, 274 and 303 were obtained.

EXAMPLE 327

To a solution of 8-(2-benzimidazolyl)sulfinylmethyl-1-ethyl-3-ethoxycarbonyl-1,2,3,4-tetrahydroquinoline(0.4 g) in methanol (80 ml) was added sodium hydroxide (0.2 g) and the mixture was stirred for 2 hours at room temperature and furthermore refluxed for 3 hours. The solvent was distilled off under reduced pressure The resulting residue was dissolved in water, and the solution was adjusted to acidic with acetic acid. The precipitate was collected by filtration and recrystallized from methanol to give 8-(2-benzimidazolyl)sulfinylmethyl-1-ethyl-1,2,3,4-tetrahydroquinoline-3-carboxylic acid.½ hydrate (0.2 g).

Colorless needle crystal mp: 162°–165° C. (decomposition)

In a manner analogous to Example 327, the same compounds as those prepared in Examples 133 and 136 were obtained using appropriate starting materials.

In a manner analogous to Example 1, 158, 159 and 314, the compounds shown in the table below were obtained using appropriate starting materials.

In the column of "bond between the 3- and 4-positions of the quinoline skeleton" in the table, the symbol "s" means a single bond and "d" means a double bond.

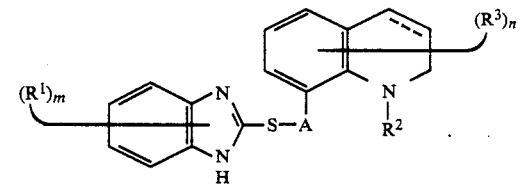

| Example No. | R$^1$ | m | A | R$^2$ | R$^3$ | n | bond between the 3- and 4- positions of the quinoline skeleton | Crystal form (recrystallization solvent) | Melting point (°C.) |
|---|---|---|---|---|---|---|---|---|---|
| 328 | 5-F 6-OCH$_3$ | 2 | CH$_2$ | CH$_2$CH=CH$_2$ | 4-NH$_2$ | 1 | s | NMR$^{(103)}$ | |
| 329 | H | 1 | CH$_2$ | C$_2$H$_5$ | 4-N(CH$_3$)(CH$_2$CH=CH$_2$) | 1 | s | White powder (ethyl acetate-n-hexane) | 145–146.5 |
| 330 | 5-F 6-OCH$_3$ | 2 | CH$_2$ | CH$_2$CH=CH$_2$ | 4-N(CH$_3$)(CH$_2$CH=CH$_2$) | 1 | s | NMR$^{(104)}$ | |

-continued

| Example No. | R¹ | m | A | R² | R³ | n | bond between the 3- and 4- positions of the quinoline skeleton | Crystal form (recrystallization solvent) | Melting point (°C.) |
|---|---|---|---|---|---|---|---|---|---|
| 331 | H | 1 | $CH_2$ | $CH_2CH=CH_2$ | 4-N(CH₃)(C₂H₅) | 1 | s | White powder (diethyl ether-n-hexane) | 145–147.5 |
| 332 | 5-F 6-OCH₃ | 2 | $CH_2$ | $CH_2CH=CH_2$ | 4-N(CH₃)(C₂H₅) | 1 | s | White powder (diethyl ether) | 131–134 |
| 333 | 5-COCH₃ | 1 | $CH_2$ | $CH_2CH=CH_2$ | 4-N(CH₃)(C₂H₅) | 1 | s | White powder (ethyl acetate) | 155–158 |
| 334 | 5-F 6-OCH₃ | 2 | $CH_2$ | $C_2H_5$ | 4-N((CH₂)₂OH)((CH₂)₂OH) | 1 | s | NMR[105] | |
| 335 | 5-F 6-OCH₃ | 2 | $CH_2$ | $C_2H_5$ | 4-N(CH₃)((CH₂)₂OH) | 1 | s | NMR[106] | |
| 336 | 5-CO-cyclopropyl | 1 | $CH_2$ | $C_2H_5$ | 4-N(CH₃)(CH₃) | 1 | s | NMR[107] | |
| 337 | 5-F 6-OCH₃ | 2 | $CH_2$ | $C_2H_5$ | 4-N(CH₃)(COCH₃) | 1 | s | NMR[108] | |
| 338 | 5-COCH₃ | 1 | $CH_2$ | $C_2H_5$ | 4-N(CH₃)(COCH₃) | 1 | s | NMR[109] | |

[103]NMR(CDCl₃)δ:
1.60(2H, brs), 1.70–1.90(1H, m), 2.09–2.32(1H, m), 3.23–3.51(2H, m), 3.66(2H, d, J=6.1Hz), 3.89(3H, s), 4.05(1H, t, J=5.5Hz), 4.26(1H, d, J=14.5Hz), 4.36(1H, d, J=14Hz), 5.30–5.52(2H, m), 5.97–6.23(1H, m), 6.77–7.43(5H, m)

[104]NMR(CDCl₃)δ:
1.60–2.00(1H, m), 2.10–2.30(1H, m), 2.20(3H, s), 2.90–4.20(8H, m), 3.88(3H, s), 5.00–5.50(4H, m), 5.65–6.25(2H, m), 6.75–7.40(4H, m), 7.62(1H, d, J=7.6Hz), 12.00–12.50(1H, br.)

[105]NMR(CDCl₃)δ:
1.42(3H, t, J=7.1Hz), 1.83–2.32(1H, m), 2.47–2.87(5H, m), 2.87–3.11(1H, m), 3.11–3.35(2H, m), 3.49–3.80(5H, m), 3.89 and 3.91(3H, s), 4.05(1H, brs), 4.06(1H, d, J=15Hz), 4.39(1H, d, J=15 Hz), 6.78–7.68(5H, m)

[106]NMR(CDCl₃)δ:
1.42(3H, t, J=7.2Hz), 1.51–198(2H, m),2.24(3H, s), 2.58–2.74(2H, m), 2.87–3.35(4H, m), 3.35–3.73(2H, m), 3.73–4.18(2H, m), 3.88 and 3.91(3H, s), 4.38(1H, d, J=14.9Hz), 6.74–7.61(5H, m)

[107]NMR(CDCl₃)δ:
1.01(2H, br.), 1.23(2H, br.), 1.39(3H, t, J=7.1Hz), 1.65–1.90(1H, m), 2.00–2.40(1H, m), 2.24(6H, s), 2.65–2.80(1H, m), 2.90–3.40(4H, m), 3.50(2H, br.), 3.78(1H, t, J=7.0Hz), 4.45(1H, d, J=14.7Hz), 7.00–7.20(1H, m), 7.30–7.70(3H, m), 7.85–8.40(2H, m), 13.30(1H, br.)

[108]NMR(CDCl₃)δ:
1.35(3H, 5, J=7.0Hz), 1.80–2.40(2H, m), 2.20(3H, s), 2.71(3H, s), 2.85–3.60(4H, m), 3.87(3H, s), 4.23(1H, d, J=14.3Hz), 4.44(1H, d, J=14.3Hz), 5.93(1H, t, J=7.0Hz, 6.85–7.59(5H, m)

[109]NMR(CDCl₃)δ:
1.47(3H, t, J=7.0Hz), 1.80–2.50(2H, m), 2.19(3H, s), 2.65(3H, s), 2.70–3.80(4H, m), 4.10–4.60(2H, m), 5.90(1H, t, J=7.0Hz), 6.90–7.29(2H, m), 7.35–7.60(2H, m), 7.80–8.10(2H, m)

In a manner analogous to Example 160, 313 and 314, the compounds shown in the table below were obtained using appropriate starting materials.

In the column of "bond between the 3- and 4-positions of the quinoline skeleton" in the table, the symbol "s" means a single bond and "d" means a double bond.

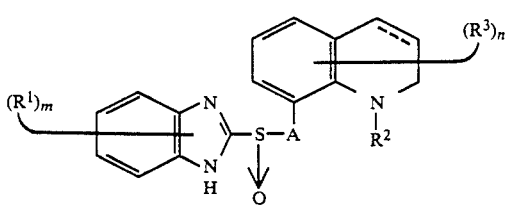

| Example No. | $R^1$ | m | A | $R^2$ | $R^3$ | n | bond between the 3- and 4-positions of the quinoline skeleton | Crystal form (recrystallization solvent) | Melting point (°C.) |
|---|---|---|---|---|---|---|---|---|---|
| 339 | 5-F 6-OCH$_3$ | 2 | CH$_2$ | C$_2$H$_5$ | 4-N(CH$_2$)$_2$OH / (CH$_2$)$_2$OH | 1 | s | Yellow powder (dichloromethane-petroleum ether) | 103–105 |
| 340 | 5-F 6-OCH$_3$ | 2 | CH$_2$ | CH$_2$CH=CH$_2$ | 4-NH$_2$ | 1 | s | Yellow powder (dichloromethane-diethyl ether) | 101–103 |
| 341 | H | 1 | CH$_2$ | C$_2$H$_5$ | 4-N(CH$_3$)(CH$_2$CH=CH$_2$) | 1 | s | Colorless needle crystals (diethyl ether-n-hexane) | 119–123 |
| 342 | 5-F 6-OCH$_3$ | 2 | CH$_2$ | CH$_2$CH=CH$_2$ | 4-N(CH$_3$)(CH$_2$CH=CH$_2$) | 1 | s | Colorless needle crystals (diethyl ether) | 135–137.5 |
| 343 | H | 1 | CH$_2$ | CH$_2$CH=CH$_2$ | 4-N(CH$_3$)(C$_2$H$_5$) | 1 | s | White powder (diethyl ether-n-hexane) | 110–115 |
| 344 | 5-F 6-OCH$_3$ | 2 | CH$_2$ | CH$_2$CH=CH$_2$ | 4-N(CH$_3$)(C$_2$H$_5$) | 1 | s | White powder (diethyl ether-n-hexane) | 145.5–148.5 |
| 345 | 5-CO-cyclopropyl | 1 | CH$_2$ | C$_2$H$_5$ | 4-N(CH$_3$)(CH$_3$) | 1 | s | White powder (diethyl ether-n-hexane) | 105–110 |
| 346 | 5-F 6-OCH$_3$ | 2 | CH$_2$ | C$_2$H$_5$ | 4-N(CH$_3$)(COCH$_3$) | 1 | s | White powder (diethyl ether-n-hexane) | 115–119 |
| 347 | 5-COCH$_3$ | 1 | CH$_2$ | C$_2$H$_5$ | 4-N(CH$_3$)(COCH$_3$) | 1 | s | Pale brown powder (diethyl ether-n-hexane) | 138–142 |

PREPARATION EXAMPLE 1

| Preparation Example 1 | |
|---|---|
| 8-(2-Benzimidazolyl)sulfinylmethyl-1-ethyl-1,2,3,4-tetrahydroquinoline | 150 g |
| Abicel (trademark of Asahi Chemical Industry) | 40 g |
| Corn starch | 30 g |
| Magnesium stearate | 2 g |
| Hydroxypropylmethylcellulose | 10 g |
| Polyethylene glycol-6000 | 3 g |
| Caster oil | 40 g |
| Ethanol | 40 g |

The compound of this invention, Abicel, corn starch and magnesium stearate are milled together and tableted by means of a R 10 mm punch (for sugar-coated tablets). The resulting tablets were coated with a film coating composition consisting of hydroxypropylmethylcellulose, Polyethylene glycol-6000, castor oil and ethanol.

PREPARATION EXAMPLE 2

| Preparation Example 2 | |
|---|---|
| 8-(5-Fluoro-6-methoxy-2-benzimidazolyl)sulfinylmethyl-1-methyl-1,2,3,4-tetrahydroquinoline | 150 g |
| Citric acid | 1.0 g |
| Lactose | 33.5 g |
| Dicalcium phosphate | 70.0 g |
| Pruronic F-68 | 30.0 g |
| Sodium laurylsulfate | 15.0 g |
| Polyvinylpyrrolidone | 15.0 g |
| Polyethyleneglycol (Carbowax 1500) | 4.5 g |
| Polyethyleneglycol (Carbowax 6000) | 45.0 g |
| Corn starch | 30.0 g |
| Dried sodium laurylsulfate | 3.0 g |
| Dried magnesium stearate | 3.0 g |
| Ethanol | Adequate amount |

The compound of this invention, citric acid, lactose, dicalcium phosphate, Pruronic F-68 and sodium lauryl sulfate were mixed The above mixture was sieved with a Screen No. 60 and turned them into wet granules using an alcoholic solution containing polyvinylpyrrolidone, Carbowax 1500 and Carbowax 6000. Alcohol, if necessary, was added to thereto to turn the powder form into a pasty mass, followed by addition of corn starch, and continued mixing until uniform particles were formed. The resulting particles were passed through a Screen No. 10, placed them in a tray and dried for 12 to 14 hours in a 100° C. oven. The dried particles were sieved with a Screen No. 16, dried sodium laurylsulfate and dried magnesium stearate were added thereto and mixed. The mixture was pressed into desired forms with a tableting machine.

The resulting core was treated with a varnish and sprayed talc thereto to prevent moisture absorption. The around of the core was coated with an undercoat layer and varnish coating of sufficient frequency for internal administration. Further, the undercoat layer-coating and a smooth-coating were applied to the coated tablets to obtain perfectly round and smooth tablets, and a color coating was applied thereto until desired color tone was obtained After drying, the resulting coated tablets were polished to obtain the tablets with a uniform luster.

PREPARATION EXAMPLE 3

| Preparation Example 3 | |
|---|---|
| 8-(2-Benzimidazolyl)sulfinylmethyl-1-ethyl-1,2,3,4-tetrahydroquinoline | 5 g |
| Polyethyleneglycol (Molecular weight: 4000) | 0.3 g |
| Sodium chloride | 0.9 g |
| Polyoxyethylene sorbitanmonooleate | 0.4 g |
| Sodium metabisulfite | 0.1 g |
| Methyl-paraben | 0.18 g |
| Propyl-paraben | 0.02 g |
| Distilled water for injection | 10.0 ml |

The above parabens, sodium metabisulfite and sodium chloride were dissolved in about a half of distilled water at 80° C. with stirring. The resulting solution was cooled to 40° C., and in the solution were dissolved the compound of the invention, polyethyleneglycol and polyoxyethylene sorbitanmonooleate. Then, distilled water for injection was added to the solution to adjust the volume to the final one, and the mixture was filtered using a suitable filter paper and sterilized to prepare the injections.

Pharmacological Tests

The results of pharmacological tests on the compounds of this invention are shown below.

Test compounds

No. 1: 1-ethyl-8-(2-benzimidazolyl)sulfinylmethyl-1,2,3,4-tetrahydroquinoline

No. 2: 1-ethyl-8-(5-methyl-2-benzimidazolyl)sulfinylmethyl-1,2,3,4-tetrahydroquinoline No. 3: 1-ethyl-8-(5-methoxy-2-benzimidazolyl)sulfinylmethyl-1,2,3,4-tetrahydroquinoline No. 4: 1-ethyl-8-(5-fluoro-2-benzimidazolyl)sulfinylmethyl-1,2,3,4-tetrahydroquinoline No. 5: 1-ethyl-8-(5,6-difluoro-2-benzimidazolyl)sulfinylmethyl-1,2,3,4-tetrahydroquinoline No. 6: 1-ethyl-8-(5-fluoro-6-methoxy-2-benzimidazolyl)sulfinylmethyl-1,2,3,4-tetrahydroquinoline No. 7: 1-ethyl-8-(5-ethoxy-6-fluoro-2-benzimidazolyl)sulfinylmethyl-1,2,3,4-tetrahydroquinoline No. 8: 1-ethyl-8-(5-chloro-2-benzimidazolyl)sulfinylmethyl-1,2,3,4-tetrahydroquinoline No. 9: 1-ethyl-8-(5-acetyl-2-benzimidazolyl)sulfinylmethyl-1,2,3,4-tetrahydroquinoline No. 10: 1-ethyl-8-(5-trifluoromethyl-2-benzimidazolyl)sulfinylmethyl-1,2,3,4-tetrahydroquinoline No. 11: 1-ethyl-8-(4-methyl-2-benzimidazolyl)sulfinylmethyl-1,2,3,4-tetrahydroquinoline No. 12: 1-ethyl-8-(4,6-dimethyl-2-benzimidazolyl)sulfinylmethyl-1,2,3,4-tetrahydroquinoline No. 13: 1-ethyl-8-(5,6-dimethyl-2-benzimidazolyl)sulfinylmethyl-1,2,3,4-tetrahydroquinoline No. 14: 1-methyl-8-(2-benzimidazolyl)sulfinylmethyl-1,2,3,4-tetrahydroquinoline No. 15: 1-methyl-8-(5-fluoro-2-benzimidazolyl)sulfinylmethyl-1,2,3,4-tetrahydroquinoline No. 16: 1-methyl-8-(5-methoxy-2-benzimidazolyl)sulfinylmethyl-1,2,3,4-tetrahydroquinoline No. 17: 1-methyl-8-(5-methyl-2-benzimidazolyl)sulfinylmethyl-1,2,3,4-tetrahydroquinoline No. 18: 1-methyl-8-(5-chloro-2-benzimidazolyl)sulfinylmethyl-1,2,3,4-tetrahydroquinoline No. 19: 1-methyl-8-(4-methyl-2-benzimidazolyl)sulfinylmethyl-1,2,3,4-tetrahydroquinoline No. 20: 1-methyl-8-(5-fluoro-6-methoxy-2-benzimidazolyl)sulfinylmethyl-1,2,3,4-tetrahydroquinoline No. 21: 1-allyl-8-(2-benzimidazolyl)sulfinylmethyl-1,2,3,4-tetrahydroquinoline No. 22: 1-allyl-8-(5-methoxy-2-benzimidazolyl)sulfinylmethyl-1,2,3,4-tetrahydroquinoline No. 23: 1-allyl-8-(5-fluoro-2-benzimidazolyl)sulfinylmethyl-1,2,3,4-tetrahydroquinoline No. 24: 1-n-butyl-8-(2-benzimidazolyl)sulfinylmethyl-1,2,3,4-tetrahydroquinoline No. 25: 1-n-butyl-8-(5-methyl-2-benzimidazolyl)sulfinylmethyl-1,2,3,4-tetrahydroquinoline No. 26: 1-propargyl-8-(2-benzimidazolyl)sulfinylmethyl-1,2,3,4-tetrahydroquinoline No. 27: 1-benzyl-8-(2-benzimidazolyl)sulfinylmethyl-1,2,3,4-tetrahydroquinoline No. 28: 1-benzyl-8-(5-methyl-2-benzimidazolyl)sulfinylmethyl-1,2,3,4-tetrahydroquinoline No. 29: 1,4-dimethyl-8-(2-benzimidazolyl)sulfinylmethyl-1,2,3,4-tetrahydroquinoline No. 30: 1,4-dimethyl-8-(5-fluoro-6-methyl-2-benzimidazolyl)sulfinylmethyl-1,2,3,4-tetrahydroquinoline No. 31: 1-ethyl-6-bromo-8-(2-benzimidazolyl)sulfinylmethyl-1,2,3,4-tetrahydroquinoline No. 32: 1-ethyl-6-methyl-8-(2-benzimidazolyl)sulfinylmethyl-1,2,3,4-tetrahydroquinoline No. 33: 1-allyl-8-(5-methyl-2-benzimidazolyl)sulfinylmethyl-1,2,3,4-tetrahydroquinoline No. 34: 1-(4-fluorobenzyl)-8-(5-methyl-2-benzimidazolyl)sulfinylmethyl-1,2,3,4-tetrahydroquinoline No. 35: 1-cyclopropylmethyl-8-(2-benzimidazolyl)sulfinylmethyl-1,2,3,4-tetrahydroquinoline No. 36: 1-ethyl-8-(2-benzimidazolyl)sulfinylmethyl-1,2,3,4-tetrahydroquinoline No. 37: 1-ethyl-8-(5-fluoro-6-methoxy-2-benzimidazolyl)sulfinylmethyl-4-methyl-1,2,3,4-tetrahydroquinoline No. 38: 1-allyl-8-(2-benzimidazolyl)sulfinylmethyl-3-methyl-1,2,3,4-tetrahydroquinoline No. 39: 1,4-dimethyl-8-(5-methyl-2-benzimidazolyl)sulfinylmethyl-1,2-dihydroquinoline No. 40: 1,4-dimethyl-8-(5-methoxy-2-benzimidazolyl)sulfinylmethyl-1,2-dihydroquinoline No. 41: 1-ethyl-8-(2-benzimidazolyl)sulfinylmethyl-4-methyl-1,2-dihydroquinoline ½-hydrate No. 42: 1,3,4-trimethyl-8-(2-benzimidazolyl)sulfinylmethyl-1,2-dihydroquinoline No. 43: 1-methyl-8-(2-benzimidazolyl)sulfinylmethyl-4-oxo-1,2,3,4-tetrahydroquinoline No. 44: 1-methyl-8-(2-benzimidazolyl)sulfinylmethyl-4-hydroxy-1,2,3,4-tetrahydroquinoline No. 45: 1,4-dimethyl-8-(2-benzimidazolyl)sulfinylmethyl-4-hydroxy-1,2,3,4-tetrahydroquinoline No. 46: 1-methyl-8-(2-benzimidazolyl)sulfinylmethyl-4-ethyl-4-hydroxy-1,2,3,4-tetrahydroquinoline No. 47: 1-ethyl-8-(5-methyl-2-benzimidazolyl)sulfinylmethyl-4-phenyl-1,2,3,4-tetrahydroquinoline No. 48: 1-ethyl-8-(2-benzimidazolyl)sulfinylmethyl-4-methoxy-1,2,3,4-tetrahydroquinoline No. 49: 1-ethyl-8-(5-fluoro-6-methoxy-2-benzimidazolyl)sulfinylmethyl-4-dimethylamino-1,2,3,4-tetrahydroquinoline No. 50: 1-ethyl-8-(2-benzimidazolyl)sulfinylmethyl-4-hydroxyimino-1,2,3,4-tetrahydroquinoline No. 51: 1-ethyl-8-(2-benzimidazolyl)sulfinylmethyl-4-allyloxy-1,2,3,4-tetrahydroquinoline No. 52: 1-ethyl-8-(2-benzimidazolyl)sulfinylmethyl-4-methylene-1,2,3,4-tetrahydroquinoline No. 53: 1-ethyl-8-(2-benzimidazolyl)sulfinylmethyl-3-methoxycarbonyl-1,2,3,4-tetrahydroquinoline No. 54: 1-ethyl-8-(2-benzimidazolyl)sulfinylmethyl-3-hydroxymethyl-1,2,3,4-tetrahydroquinoline No. 55: 1-ethyl-8-(2-benzimidazolyl)sulfinylmethyl-3-dimethylcarbamoyl-1,2,3,4-tetrahydroquinoline ½-hydrate No. 56: 1-ethyl-8-(2-benzimidazolyl)sulfinylmethyl-3-carboxy-1,2,3,4-tetrahydroquinoline ½hydrate No. 57: 1-ethyl-8-(2-benzimidazolyl)sulfinylmethyl-4-[N-methyl-N-(2-hydroxyethyl)amino]-1,2,3,4-tetrahydroquinoline No. 58: 1-ethyl-8-(2-benzimidazolyl)sulfinylmethyl-3-(1-piperizinyl)carbonyl-1,2,3,4-tetrahydroquinoline No. 59: 1-ethyl-8-(2-benzimidazolyl)sulfinylmethyl-4-(N-methyl-N-acetyl)amino-1,2,3,4-tetrahydroquinoline No. 60: 1-ethyl-8-(5-methyl-2-benzimidazolyl)sulfinylmethylmethyl-4-allylamino-1,2,3,4-tetrahydroquinoline No. 61: 1-ethyl-8-(5-methyl-2-benzimidazolyl)sulfinylmethylmethyl-4-cyclohexylamino-1,2,3,4-tetrahydroquinoline No. 62: 1-allyl-8-(5-methyl-2-benzimidazolyl)sulfinylmethylmethyl-4-methoxy-1,2,3,4-tetrahydroquinoline No. 63: 1-ethyl-8-(5-fluoro-6-methoxy-2-benzimidazolyl)sulfinylmethyl-4-hydroxymethyl-1,2,3,4-tetrahydroquinoline No. 64: 1-ethyl-8-(5-fluoro-6-methoxy-2-benzimidazolyl)sulfinylmethyl-4-(N-methyl-N-cyclopropyl)amino-1,2,3,4-tetrahydroquinoline No. 65: 1-ethyl-8-(5-fluoro-6-methoxy-2-benzimidazolyl)sulfinylmethyl-4-(N-formyl-N-cyclopropyl)amino-1,2,3,4-tetrahydroquinoline No. 66: 1-ethyl-8-(5-methyl-2-benzimidazolyl)sulfinylmethyl-4-methoxy-3,3-dimethyl-1,2,3,4-tetrahydroquinoline No 67: 1-ethyl-8-(5-fluoro-6-methoxy-2-benzimidazolyl)sulfinylmethyl-4-(N-methyl-N-allyl)amino-1,2,3,4tetrahydroquinoline No. 68: 1-ethyl-8-(5-fluoro-6-methoxy-2-benzimidazolyl)sulfinylmethyl-4-(N-methyl-N-cyclopropylmethyl)amino-1,2,3,4-tetrahydroquinoline No. 69: 1-ethyl-8-(5-fluoro-6-methoxy-2-benzimidazolyl)sulfinylmethyl-4-[N-methyl-N-(2,2,2-trifluoro-1ethoxyethyl)]amino-1,2,3,4-tetrahydroquinoline No. 70: 1-ethyl-8-(5-fluoro-6-methoxy-2-benzimidazolyl)sulfinylmethyl-4-[N-allyl-N-(4-methoxybenzyl)]amino1,2,3,4-tetrahydroquinoline No. 71: 8-(5-fluoro-6-methoxy-2-benzimidazolyl)sulfinylmethyl-4-(N-allyl-N-methyl)amino-1,2,3,4-tetrahydroquinoline No. 72: 1-ethyl-8-(2-benzimidazolyl)sulfinylmethyl-4-trifluoromethyl-1,2-dihydroquinoline Pharmacological test 1

$H^+ + K^+$ ATPase (adenosine triphosphatase) (amount of protein: 10 μg) prepared from porcine stomach was added to a Pipes-TRIS [i.e. 2-amino-2-(hydroxymethyl)-1,3-propanediol] buffer solution (pH 6.1) containing 2 mM of piperazine N,N'-bis(2-ethanesulfonic acid), and the mixture was let stand at room temperature. A test compound was dissolved in dimethyl formamide, and the mixture was added to said $H^+ + K^+$ ATPase buffer solution so that the final concentration should be 1% and let stand for reaction for 30 minutes at room temperature. Then a 75 mM Pipes-TRIS buffer (1 ml, pH 7.4) (containing 4 mM $MgCl_2$, 4 mM $Na_2ATP$, and 20 mM KCl) and a 75 mM Pipes-TRIS buffer (1 ml, pH 7.4) (containing 4 mM $MgCl_2$, and 4 mM $Na_2ATP$) were added to the solution individually to make two kinds of samples and these samples were presented for reaction for 30 minutes at 37° C. 40% Trichloroacetic acid (0.3 ml) was added to each sample to stop the reaction. The solution were subjected to centrifugal separation (3000 rpm) for 10 minutes, and the supernatant was taken off, then the formed inorganic phosphoric acid was measured by Fiske and Subbarow's method [J. Biol. Chem. vol. 66, 375 (1925)]. The value of deducting the amount of inorganic phosphoric acid taken from the Pipes-Tris buffer not containing 20 mM KCl from that taken from the Pipes-Tris buffer containing 20 mM KCl was calculated in terms of unit protein and unit hour to be defined as an activity index of enzyme. Inhibition level (%) in doses of administration was estimated by control values and activity indices of enzyme, and from the obtained inhibition level (%), $IC_{50}$ (dose of administration of compounds to inhibit in 50%) was obtained.

The results are shown in the table below.

| Test compound No. | $IC_{50}$ (M) | Test compound No. | $IC_{50}$ (M) |
| --- | --- | --- | --- |
| 1 | $1.9 \times 10^{-7}$ | 16 | $6.9 \times 10^{-7}$ |
| 2 | $1.8 \times 10^{-7}$ | 17 | $5.3 \times 10^{-7}$ |
| 3 | $4.5 \times 10^{-7}$ | 18 | $2.0 \times 10^{-7}$ |
| 4 | $1.0 \times 10^{-6}$ | 19 | $4.1 \times 10^{-7}$ |
| 5 | $4.4 \times 10^{-7}$ | 20 | $3.3 \times 10^{-7}$ |
| 6 | $6.2 \times 10^{-7}$ | 21 | $3.3 \times 10^{-7}$ |
| 7 | $1.6 \times 10^{-6}$ | 22 | $9.6 \times 10^{-7}$ |
| 8 | $2.2 \times 10^{-7}$ | 23 | $4.9 \times 10^{-7}$ |
| 9 | $2.2 \times 10^{-6}$ | 24 | $1.8 \times 10^{-7}$ |
| 10 | $3.7 \times 10^{-7}$ | 25 | $3.3 \times 10^{-7}$ |
| 11 | $5.0 \times 10^{-7}$ | 26 | $1.6 \times 10^{-6}$ |
| 12 | $4.2 \times 10^{-7}$ | 27 | $3.9 \times 10^{-7}$ |
| 13 | $1.7 \times 10^{-7}$ | 28 | $6.5 \times 10^{-7}$ |

-continued

| Test compound No. | IC$_{50}$ (M) | Test compound No. | IC$_{50}$ (M) |
|---|---|---|---|
| 14 | $1.7 \times 10^{-7}$ | 29 | $2.5 \times 10^{-7}$ |
| 15 | $5.3 \times 10^{-7}$ | 30 | $6.1 \times 10^{-7}$ |
| 31 | $6.4 \times 10^{-6}$ | 46 | $1.8 \times 10^{-6}$ |
| 32 | $9.2 \times 10^{-7}$ | 47 | $1.5 \times 10^{-6}$ |
| 33 | $5.8 \times 10^{-7}$ | 48 | $1.1 \times 10^{-6}$ |
| 34 | $2.1 \times 10^{-6}$ | 50 | $4.7 \times 10^{-6}$ |
| 35 | $2.5 \times 10^{-7}$ | 51 | $2.9 \times 10^{-6}$ |
| 36 | $4.5 \times 10^{-7}$ | 52 | $3.9 \times 10^{-6}$ |
| 37 | $8.9 \times 10^{-7}$ | 53 | $4.9 \times 10^{-6}$ |
| 38 | $8.3 \times 10^{-7}$ | 54 | $1.2 \times 10^{-6}$ |
| 39 | $1.3 \times 10^{-7}$ | 55 | $5.1 \times 10^{-6}$ |
| 40 | $5.2 \times 10^{-7}$ | 56 | $1.9 \times 10^{-6}$ |
| 41 | $2.3 \times 10^{-7}$ | 58 | $5.9 \times 10^{-6}$ |
| 42 | $5.5 \times 10^{-7}$ | 59 | $5.7 \times 10^{-6}$ |
| 43 | $6.7 \times 10^{-6}$ | 60 | $3.3 \times 10^{-6}$ |
| 45 | $2.2 \times 10^{-6}$ | 62 | $4.0 \times 10^{-6}$ |
| 63 | $4.5 \times 10^{-6}$ | 69 | $4.9 \times 10^{-6}$ |
| 64 | $4.0 \times 10^{-6}$ | 70 | $3.8 \times 10^{-6}$ |
| 65 | $2.8 \times 10^{-6}$ | 71 | $5.7 \times 10^{-6}$ |
| 66 | $3.3 \times 10^{-7}$ | 72 | $3.3 \times 10^{-6}$ |

Pharmacological test 2

Male Wistar rats (200 to 250 g of body weight) were fasted for 24 hours. A test compound was suspended in 0.5% carboxymethyl cellulose solution and administered to each rat. 30 minutes after administration, 0.6 N hydrochloric acid was orally administered by 1 ml per rat. 1 hour later, the rats were sacrificed and their stomachs were extracted. After fixing the extracted stomach lightly by administering 1% formalin solution (10 ml), the area of lesion generated in stomach was measured to define an ulcer factor.

Inhibition ratio in doses of test compounds was calculated from the control value obtained from a sample administered only a 0.5% solution of carboxymethyl cellulose. The value of ED$_{50}$ was figured out from the obtained inhibition ratio by means of probit method.

Test results are shown in the table below.

| Test Compound No. | ED$_{50}$ (mg/Kg) | Test Compound No. | ED$_{50}$ (mg/Kg) |
|---|---|---|---|
| 2 | 2.5 | 14 | 4.6 |
| 3 | 5.0 | 16 | 3.4 |
| 6 | 7.5 | 19 | 6.8 |
| 9 | 1.6 | 20 | 8.8 |
| 11 | 3.3 | 21 | 6.4 |

Pharmacological test 3

Male Wistar rats weighing 160 to 180 g were presented to the experiment after being fasted for 24 hours. Aspirin was suspended in 0.5% carboxymethyl cellulose and orally administered to the rats at a dose of 200 mg/kg. 5 hours after the administration of aspirin, rats were sacrificed to extract their stomachs. Inner and outer layers of the stomach were fixed by administering 1% formalin solution (10 ml) in the stomach and dipping into a 1% formalin solution for 30 minutes. By resectioning the stomach along the greater curvature, the length of ulcer was measured by stereoscopic microscope (10x), and the sum of the length is defined as ulcer factor. Test compounds were orally administered 30 minutes before the administration of aspirin at doses of 1, 3, 10, and 30 mg/kg. Then from the inhibition ratio (%) of the group of test compound against the control group, the ED$_{50}$ was calculated by means of probit method.

| Test compound No. | ED$_{50}$ (mg/kg) |
|---|---|
| 49 | 3.5 |
| 57 | 6.3 |
| 67 | 5.5 |
| 68 | 5.9 |

What we claim is:

1. A hydroquinoline compound of the formula:

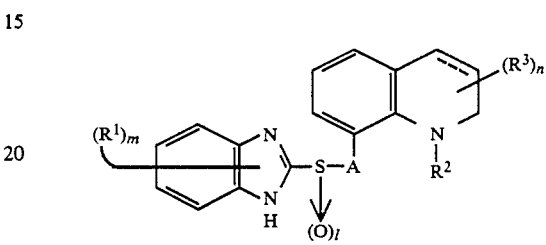

wherein A is a methylene group; $R^1$ is a hydrogen atom, a $C_1$-$C_6$ alkyl group, a $C_1$-$C_6$ alkoxy group, a halogen atom or a $C_1$-$C_6$ alkanoyl group; $R_2$ is a $C_2$-$C_6$ alkenyl group; $R^3$ is a $C_1$-$C_6$ alkyl group, a $C_1$-$C_6$ alkoxy group, or a group of the formula:

wherein $R^4$ and $R^5$ are, the same or different, a hydrogen atom or a $C_1$-$C_6$ alkyl group; m is an integer of 1 or 2; n and l are integers of 1; and the bond between the 3- and 4-positions of the quinoline skeleton is a single bond; or its pharmaceutically acceptable salt.

2. A hydroquinoline compound or its pharmaceutically acceptable salt as claimed in claim 1, wherein $R^3$ is a $C_1$-$C_6$ alkyl group or a $C_1$-$C_6$ alkoxy group.

3. A hydroquinoline compound of the formula:

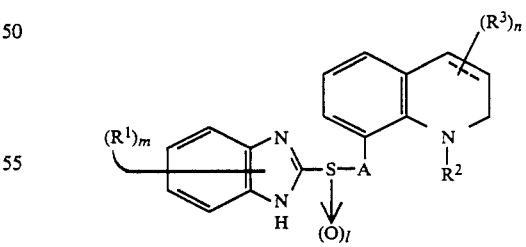

wherein A is a methylene group; n is an integer of 1 or 2; $R^1$ is a hydrogen atom, a $C_1$-$C_6$ alkyl group, a $C_1$-$C_6$ alkoxy group, a halogen atom or a $C_1$-$C_6$ alkanoyl group; $R^2$ is a $C_1$-$C_6$ alkyl group; and when n is 1, $R^3$ is a hydrogen group, a $C_2$-$C_6$ alkenyloxy group, a $C_1$-$C_4$ alkylenedioxy group, a $C_1$-$C_6$ alkylidene group, a hydroxy-substituted $C_1$-$C_6$ alkyl group, or a group of the formula:

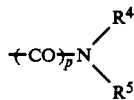

wherein p is an integer of 0 to 1; $R^4$ and $R^5$ are, the same or different, a hydrogen atom, a $C_1-C_6$ alkyl group, a hydroxy-substituted $C_1-C_6$ alkyl group, a $C_3-C_8$ cycloalkyl group, a $C_3-C_8$ cyloalkyl-$C_1-C_6$ alkyl group, a $C_2-C_6$ alkenyl group, a $C_1-C_6$ alkanoyl group, and $R^4$ and $R^5$ together with the bonding nitrogen atom may form a piperidino group or a pyrrolidinyl group, and when n is 2, $R^3$ is a hydroxy group or a $C_1-C_6$ alkyl group; l is an integer of 1; m is an integer of 1 or 2; and the bond between the 3- and 4-positions of the quinoline skeleton is a single bond; provided that $R^4$ and $R^5$ cannot both be a hydrogen atom or both be a $C_1-C_6$ alkyl group or one cannot be a hydrogen atom and the other a $C_1-C_6$ alkyl group or a $C_1-C_6$ alkanoyl group; or its pharmaceutically acceptable salt.

4. A hydroquinoline compound or its pharmaceutically acceptable salt as claimed in claim 3, wherein n is 1 and $R^3$ is a group of the formula:

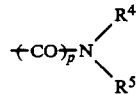

5. A hydroquinoline compound or its pharmaceutically acceptable salt as claimed in claim 3, wherein n is 1 and $R^3$ is a hydroxy group, a $C_2-C_6$ alkenyloxy group, a $C_1-C_4$ alkylenedioxy group, a $C_1-C_6$ akylidene group, or a hydroxy-substituted $C_1-C_6$ alkyl group.

6. A hydroquinoline compound of its pharmaceutically acceptable salt as claimed in claim 5, wherein $R^3$ is attached to the quinoline skeleton at the 4-position thereof.

7. A hydroquinoline compound or its pharmaceutically acceptable salt as claimed in claim 3, wherein n is 2.

8. A hydroquinoline compound or its pharmaceutically acceptable salt as claimed in claim 7, wherein $R^2$ is a $C_1-C_2$ alkyl group, and at least one $R^3$ is attached to the hydroquinoline skeleton at the 4-position thereof.

9. A hydroquinoline compound or its pharmaceutically acceptable salt as claimed in claim 3, wherein p is an integer of 0.

10. A hydroquinoline compound or its pharmaceutically acceptable salt as claimed in claim 9, wherein $R^4$ and $R^5$ together with the bonding nitrogen atom form a pyrrolidinyl group, or a piperidino group.

11. A hydroquinoline compound or its pharmaceutically acceptable salt as claimed in claim 9, wherein $R^4$ is a $C_1-C_6$ alkyl group and $R^5$ is a $C_1-C_6$ alkanoyl group, a hydroxy-substituted $C_1-C_6$ alkyl group, a $C_3-C_8$-cycloalkyl group, or a $C_2-C_6$ alkenyl group.

12. A hydroquinoline compound or its pharmaceutically acceptable salt as claimed in claim 9, wherein $R^3$ is attached to the quinoline skeleton at the 4-position thereof.

13. A hydroquinoline compound or its pharmaceutically acceptable salt as claimed in claim 3, wherein p is an integer of 1.

14. 8-(5-Fluoro-6-methoxy-2-benzimidazolyl)sulfinylmethyl-1-ethyl-4-(N-methyl-N-allyl)amino-1,2,3,4-tetrahydroquinoline.

15. 8-(5-Acetyl-2-benzimidazolyl)sulfinylmethyl-1-allyl-4-dimethylamino-1,2,3,4-tetrahydroquinoline.

16. 8-(5-fluoro-6-methoxy-2-benzimidazolyl)sulfinylmethyl-1-ethyl-4-(N-methyl-N-cyclopropyl)amino-1,2,3,4-tetrahydroquinoline.

17. 8-(5-fluoro-6-methoxy-2-benzimidazolyl)sulfinylmethyl-1-allyl-4-dimethylamino-1,2,3,4-tetrahydroquinoline.

18. 8-(2-benzimidazolyl)-sulfinylmethyl-1-allyl-4-dimethylamino-1,2,3,4-tetrahydroquinoline.

19. A pharmaceutical composition for use as an antiulcer agent comprising a therapeutically effective amount of a hydroquinoline compound of claim 1, or pharmaceutically acceptable salt thereof, and a pharmaceutically acceptable carrier.

20. A pharmaceutical composition for use as an antiulcer agent comprising a therapeutically effective amount of a hydroquinoline compound of claim 3, or pharmaceutically acceptable salt thereof, and a pharmaceutically acceptable carrier.

* * * * *

UNITED STATES PATENT AND TRADEMARK OFFICE
CERTIFICATE OF CORRECTION

PATENT NO. : 4,963,566
DATED : October 16, 1990
INVENTOR(S) : Minoru Uchida et al.

It is certified that error appears in the above-identified patent and that said Letters Patent is hereby corrected as shown below:

Claim 1, column 140, line 40, "1" (first occurrence) should be --$l$--.

Claim 3, column 140, line 64, "hydrogen" should be --hydroxy--; and column 141, line 15, "1" (first occurence) should be --$l$--.

Title page, item [57]
ABSTRACT

Second line (first below formula), "1" should be --$l$--.

Signed and Sealed this

Thirtieth Day of November, 1993

Attest:

BRUCE LEHMAN

Attesting Officer

Commissioner of Patents and Trademarks